US008148069B2

(12) United States Patent  
Croce et al.

(10) Patent No.: US 8,148,069 B2
(45) Date of Patent: Apr. 3, 2012

(54) MICRORNA-BASED METHODS AND COMPOSITIONS FOR THE DIAGNOSIS, PROGNOSIS AND TREATMENT OF SOLID CANCERS

(75) Inventors: Carlo M. Croce, Columbus, OH (US); George A. Calin, Pearland, TX (US); Stefano Volinia, Ferrara (IT)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 12/160,061

(22) PCT Filed: Jan. 3, 2007

(86) PCT No.: PCT/US2007/000159
§ 371 (c)(1),
(2), (4) Date: Jul. 3, 2008

(87) PCT Pub. No.: WO2007/081740
PCT Pub. Date: Jul. 19, 2007

(65) Prior Publication Data
US 2008/0306006 A1 Dec. 11, 2008

Related U.S. Application Data

(60) Provisional application No. 60/756,585, filed on Jan. 5, 2006.

(51) Int. Cl.
C12Q 1/68 (2006.01)
(52) U.S. Cl. ....................................................... 435/6.1
(58) Field of Classification Search .................... None
See application file for complete search history.

(56) References Cited

U.S. PATENT DOCUMENTS

| | | |
|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 * | 3/2010 | Croce et al. ...................... 436/6 |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |

(Continued)

FOREIGN PATENT DOCUMENTS

CA   2587189   12/2006

(Continued)

OTHER PUBLICATIONS

Tockman et al (Cancer Res., 1992, 52:2711s-2718s).*

(Continued)

*Primary Examiner* — Sean Aeder
(74) *Attorney, Agent, or Firm* — MacMillan, Sobanski & Todd, LLC

(57) ABSTRACT

The present invention provides novel methods and compositions for the diagnosis and treatment of solid cancers. The invention also provide methods of identifying inhibitors of tumorigenesis.

3 Claims, 9 Drawing Sheets

U.S. PATENT DOCUMENTS

| | | |
|---|---|---|
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1* | 7/2007 | Brown et al. ............. 435/6 |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1* | 7/2009 | Brown et al. ............. 514/44 |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| FR | 2877350 | 5/2006 |
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/10343 COR | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 0076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | WO 03/078662 A1 * | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005/020795 | 3/2005 |
| WO | 2005060661 | 7/2005 |
| WO | 2005/078139 | 8/2005 |
| WO | WO2005/078139 A2 | 8/2005 |
| WO | WO 2005/078139 A2 * | 8/2005 |
| WO | 2005/080601 | 9/2005 |
| WO | 2005/118806 | 12/2005 |
| WO | WO2005118806 A2 | 12/2005 |
| WO | 2006/105486 | 10/2006 |
| WO | 2006/108718 | 10/2006 |
| WO | 2006108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | WO2007016548 A2 | 2/2007 |
| WO | 2007/033023 | 3/2007 |
| WO | WO2007033023 A2 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007/127190 | 11/2007 |
| WO | 2008/008430 | 1/2008 |
| WO | 2008/036776 | 3/2008 |
| WO | 2008/054828 | 5/2008 |

| | | |
|---|---|---|
| WO | 2008/054828 C | 5/2008 |
| WO | 2008/070082 | 6/2008 |
| WO | 2008/073920 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Chan et al (Cancer Research, 2005, 65(14): 6029-6033).*
Xi et al (Biomarker Insights, 2006, 1: 113-121).*
Iorio et al (Cancer Research, 2005, 65(16): 7065-7070).*
Michael et al (Molecular Cancer Research, Oct. 2003, 1:882-891).*
International Search Report, International Application No. PCT/US07/00159 filed Jan. 3, 2007.
Chan et al., MicroRNA-21 is an Antiapoptotic Factor in Human Glioblastoma Cells, Cancer Res. 2005; 65: (14), Jul. 15, 2005, pp. 6029-6033. Supplemental Data 1. List of miRNAs analyzed by the miRNA arrays.
Cheng et al., Antisense inhibition of human miRNAs and indications for an involvement of miRNA in cell growth and apoptosis, Nucleic Acids Research, 2005, vol. 33, No. 4, pp. 1290-1297.
Iorio et al., MicroRNA Gene Expression Deregulation in Human Breast Cancer, Cancer Res. 2005; 65: (16), Aug. 15, 2005, pp. 7065-7070.
Liu et al., An oligonucleotide microchip for genome-wide microRNA profiling in human and mouse tissues, PNAS, Jun. 29, 2004, vol. 101, No. 26, pp. 9740-9744.
Michael et al., Reduced Accumulation of Specific MicroRNAs in Colorectal Neoplasia, Molecular Cancer Research, vol. 1, Oct. 2003, pp. 882-891.
Takamizawa et al., Reduced Expression of the let-7 MicroRNAs in Human Lung Cancers in Association with Shortened Postoperative Survival, Cancer Research 64, Jun. 1, 2004, pp. 3753-3756.
Thomson et al., A custom microarray platform for analysis of microRNA gene expression, Nature Methods, vol. 1, No. 1, Oct. 2004, pp. 1-7.
Volinia et al., A microRNA expression signature of human solid tumors defines cancer gene targets, PNAS, Feb. 14, 2006, vol. 103, No. 7, pp. 2257-2261.
European Patent Office Communication and Notification, PCT/US2007000159, dated Oct. 23, 2009 and Nov. 10, 2009.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bartel, D. P., "MicroRNAs: Target Recognition and Regulatory Functions," Cell, Jan. 2009, pp. 215-233, vol. 136.
Bednarek, A. K. et al., "WWOX, The FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G.A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Dalmay, T. et al., "MicroRNAs and the Hallmarks of Cancer," Oncogene, 2006, pp. 6170-6175, vol. 25.
Davies, F. E. et al., "Insights into the Multistep Transformation of MGUS to Myeloma Using Microarray Expression Analysis," Blood, Dec. 2003, pp. 4504-4511, vol. 102, No. 13.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, et al., "FHIT," Atlas of Genetics and Cytogenetics in Oncology and Haematology, 2007, pp. 171-178, vol. 2.
Eis, P. S. et al., "Accumulation of miR-155 and BIC RNA in Human B Cell Lymphomas," PNAS, Mar. 2005, pp. 3627-3632, vol. 102, No. 10.
European Patent Application, EP 1795203 A2, Croce et al., Application No. 06010581.4, filed Feb. 7, 1997, published Jun. 13, 2007.
European Search Report, Application No. 06800599.0 dated Oct. 19, 2009.
European Search Report, Application No. 06814375.9 dated Oct. 8, 2009.
European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep. 14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 08796821.0 dated Aug. 4, 2010.
European Search Report, Application No. 08841700.1 dated Jun. 2, 2010.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth In Vitro and In Vivo," PNAS, Oct. 2005, pp. 15611-15616, vol. 102, No. 43.
Fong, Y. et al., "Muir-Torre-Like Syndrome in FHIT-Deficient Mice," PNAS, Apr. 2000, pp. 4742-4747, vol. 97, No. 9.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.

Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM, May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.

McManus, M. T., "MicroRNAs and Cancer," Seminars in Cancer Biology, 2003, pp. 253-258, vol. 13.

Megraw, M. et al., "miRGen: A Database for the Study of Animal MicroRNA Genomic Organization and Function," Nucleic Acids Research, 2007, pp. D149-D155, vol. 35.

Meng, F. et al., "Involvement of Human MicroRNA in Growth and Response to Chemotherapy in Human Cholangiocarcinoma Cell Lines," Gastroenterology, 2006, pp. 2113-2129, vol. 130.

Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.

Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.

Mitchell, P. S. et al., "Circulating MicroRNAs as Stable Blood-Based Markers for Cancer Detection," PNAS, Jul. 2008, pp. 10513-10518, vol. 105, No. 30.

Mitrovic, T. et al., "Cancer Gene Therapy," Arch. Oncology, 2005, pp. 23-26, vol. 13, No. 1.

Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.

Negrini, M. et al., "MicroRNAs in Human Cancer: From Research to Therapy," Journal of Cell Science, Apr. 2007, pp. 1833-1840, vol. 120.

Notice of Allowance and Fees Due in U.S. Appl. No. 12/160,064, filed Jul. 3, 2008, mailing date Nov. 20, 2009.

Notice of Allowance and Fees Due in U.S. Appl. No. 12/298,221, filed Nov. 10, 2008, mailing date Nov. 30, 2009.

Office Action issued in U.S. Appl. No. 12/083,067, filed Jun. 20, 2008, mailing date Jul. 8, 2010.

Office Action issued in U.S. Appl. No. 12/160,034, filed Jul. 3, 2008, mailing date Jun. 7, 2010.

Office Action issued in U.S. Appl. No. 12/160,061, filed Jul. 3, 2008, mailing date Mar. 12, 2010.

Office Action issued in U.S. Appl. No. 12/160,061, filed Jul. 3, 2008, mailing date Apr. 24, 2009.

Office Action issued in U.S. Appl. No. 12/160,061, filed Jul. 3, 2008, mailing date Oct. 30, 2009.

Office Action issued in U.S. Appl. No. 12/160,064, filed Jul. 3, 2008, mailing date Aug. 10, 2009.

Office Action issued in U.S. Appl. No. 12/293,471, filed Oct. 9, 2008, mailing date Jun. 8, 2010.

Office Action issued in U.S. Appl. No. 12/373,358, filed Feb. 11, 2009, mailing date Aug. 20, 2010.

Office Action issued in U.S. Appl. No. 12/442,018, filed Mar. 27, 2009, mailing date Apr. 15, 2010.

Palamarchuk, A. et al., "Akt Phosphorylates Tcl1 Oncoprotein and Inhibits Its Repressor Activity," Cancer Research, Jun. 2005, pp. 4515-4519, vol. 65, No. 11.

Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US2007/023660 filed Nov. 1, 2007, dated May 5, 2009.
PCT International Preliminary Report on Patentability, PCT/US2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.

Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.

Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.

Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Thomson, J. M. et al., "A Custom Microarray Platform for Analysis of MicroRNA Gene Expression," Nature Methods, Oct. 2004, pp. 1-7, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Valeri, N. et al., "Epigenetics, miRNAs, and Human Cancer: A New Chapter in Human Gene Regulation," Mamm Genome, Aug. 2009, pp. 573-580, vol. 20.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. Pages ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

Chinese Office Action, Application No. 200780040146.7 dated May 25, 2011.

European Communication Pursuant to Article 94(3) EPC, Application No. 07867402.5, dated Jan. 5, 2011, European Communication Pursuant to Article 94(3) EPC, Application No. 08767439.9, dated Mar. 15, 2011, PCT International Preliminary Report on Patentability, PCT/US2009/065072 filed Nov. 19, 2009, dated Jun. 3, 2011.

European Communication Pursuant to Article 94(3) EPC, Application No. 08768266.2, dated Apr. 18, 2011.

European Communication Pursuant to Article 94(3) EPC, Application No. 07810382.7, dated Dec. 8, 2010.

European Supplementary Search Report, Application No. 09715064.3 dated May 24, 2011.

PCT Internatioanl Preliminary Report on Patentability, PCT/US2009/038214 filed Mar. 25, 2009, dated Jun. 16, 2011.

Chinese Office Action, Application No. 200680036598.3 dated Feb. 24, 2011.

Canadian Intellectual Property Office, Requisition by the Examiner, Application No. 2,635,616, Dated Feb. 21, 2011.

Chinese Office Action, Application No. 200780005821.2 dated Jan. 26, 2011.

European Search Report, Application No. 08798444.9-2402, PCT/US2008/073964, dated Dec. 16, 2010.
European Search Report, Application No. 08799295.4-2402, PCT/US2008/075565, dated Nov. 9, 2010.
EP Search Report, Application No. 08782609.5 dated Oct. 28, 2010, 57-29302.
Canadian Office Action, Application No. 2,617,581, dated Feb. 1, 2011.
European Search Report, Application No. 08841700.1, dated Jan. 4, 2011.
Canadian Office Action, Application No. 2,621,441, dated Feb. 1, 2011.
Ambros, V. et al., "A Uniform System for MicroRNA Annotation," RNA, 2003, pp. 277-279, vol. 9.
Baira, E. et al., "Ultraconserved Elements: Genomics, Function and Disease," RNA Biology, Jul. 2008, pp. 132-134, vol. 5, No. 3.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Caldas, C. et al., "Sizing Up miRNAs as Cancer Genes," Nature Medicine, Jul. 2005, pp. 712-714, vol. 11, No. 7.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chim, S.S.C. et al., "Detection and Characterization of Placental MicroRNAs in Maternal Plasma," Clinical Chemistry, 2008, pp. 482-490, vol. 54, No. 3.
Cui, S. et al., "MicroRNAs that Underlie Ovarian Cancer Development and Response to Chemotherapy," 98th AACR Annual Meeting, Apr. 14-18, 2007, Los Angeles, CA.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Esquela-Kerscher, A. et al., "Oncomirs—MicroRNAs with a Role in Cancer," Nature Reviews:Cancer, Apr. 2006, pp. 259-269, vol. 6.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Feng, G. et al., "Elevated Serum-Circulating RNA in Patients with Conventional Renal Cell Cancer," Anticancer Research, 2008, pp. 321-326, vol. 28.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Ford, L.P., "A MicroRNA Expression Signature of Human Solid Tumors Defines Cancer Gene Targets," Leukemia Research, 2006, pp. 511-513, vol. 30.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.

He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.
Kozomara, A. et al., "miRBase: Integrating MicroRNA Annotation and Deep-Sequencing Data," Nucleic Acids Research, 2011, pp. D152-D157, vol. 39.
Lagos-Quintana, M. et al., "Identification of Tissue-Specific MicroRNAs from Mouse," Current Biology, Apr. 2002, pp. 735-739, vol. 12.
Landgraf, P. et al., "A Mammalian MicroRNA Expression Atlas Based on Small RNA Library Sequencing," Cell, Jun. 2007, pp. 1401-1414, vol. 129.
Lanza, G. et al., "mRNA/microRNA Gene Expression Profile in Microsatellite Unstable Colorectal Cancer," Molecular Cancer, 2007, pp. 1-11, vol. 6, No. 54.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, S.-C. et al., "Bioinformatic Discovery of MicroRNA Precursors from Human ESTs and Introns," BMC Genomics, 2006, vol. 7.
Lujambio, A. et al., "A MicroRNA DNA Methylation Signature for Human Cancer Metastasis," PNAS, Sep. 2008, pp. 13556-13561, vol. 105, No. 36.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Mendell, J.T., "miRiad Roles for the miR-17-92 Cluster in Development and Disease," Cell, 2008, pp. 217-.
Mendell, J.T., "miRiad Roles for the miR-17-92 Cluster in Development and Disease," Cell, 2008, pp. 217-222, vol. 133.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nam, E.J. et al., "MicroRNA Expression Profiles in Serous Ovarian Carcinoma," Clinical Cancer Research, 2008, pp. 2690-2695, vol. 14, No. 9.
Nicoloso, M.S. et al., "MicroRNAs—The Micro Steering Wheel of Tumour Metastases," Nature Reviews: Cancer, Apr. 2009, pp. 293-302, vol. 9.
Nurden, A.T., "Qualitative Disorders of Platelets and Megakaryocytes," Journal of Thrombosis and Haemostasis, 2005, vol. 3, pp. 1773-1782.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Saini, H. K. et al., "Annotation of Mammalian Primary MicroRNAs," BMC Genomics, 2008, vol. 9.

Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Sigma1-Based Attachment Protein," Molecular Therapy, May 2006, pp. 997-1005, vol. 13, No. 5.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Slack, F.J., "Big Roles for Small RNAs," Nature, Feb. 2010, p. 616, vol. 463.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Tilt, E. et al., "Expression and Function of Micro RNAs in Immune Cells During Normal or Disease State," International Journa of Medicine Sciences, 2008, pp. 73-79, vol. 5, No. 2.

Tumour-Related MicroRNAs Functions in Caenorhabditis Elegans, Oncogene, 2006, pp. 6197-6201, vol. 25.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Valeri, N. et al., "Modulation of Mismatch Repair and Genomic Stability by miR-155," PNAS, Apr. 2010, pp. 6982-6987, vol. 107, No. 15.

Wijermans, P.W., "Low Dose Azanucleosidesfor High Risk (s) MDS and AML," Haematologica Reports,Nov. 2006, pp. 74-76. vol. 2, Issue, 15.

Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.

European Seach Report, Application No. 11151769-4, dated Feb. 8, 2011.

European Search Report, Application No. 11151771-0, dated Feb. 8, 2011.

European Search Report, Application No. 11151772-8, dated Feb. 8, 2011.

European Search Report, Application No. 08713330.2, dated Jul. 22, 2011.

Chinese Office Action, Application No. 200680039776.8 dated Jun. 30, 2011.

Australian Office Action, Application No. 2006291165 dated Aug. 23, 2011.

European Search Report, Application No. 11151749.6, dated Feb. 8, 2011.

Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.

Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.

Meng, F. et al., "MicroRNA-21 Regulates Expression of the PTEN Tumor Suppressor Gene in Human Hepatocellular Cancer," Gastroenterology, 2007, pp. 647-658, vol. 133.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.

Verschuur, A.C., "Acute Megakaryoblastic Leukemia," May 2004, pp. 1-5, Retrieved from the Internet: URL: http://www.orpga.net/data/patho/GB/uk-AMLM7.pdf.

\* cited by examiner

FIG. 8

```
                       SEQUENCE LISTING

<160> NUMBER OF SEQ ID NOS: 498

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuagggguc acacccacca cugggagaua     60
acuauacaau cuacugucuu uccuaacgug                                       90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu     60
ccuagcuuuc cu                                                          72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acuauacaau     60
cuacugucuu uccu                                                        74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag     60
auaacuguac agccuccuag cuuuccuugg gucuugcacu aaacaac                   107
```

```
<210> SEQ ID NO 5
<211> LENGTH: 85
<212> TYPE: RNA
<213> ORGANISM: Homo sapiens

<400> SEQUENCE: 5
ggcgggguga gguaguaggu ugugugguuu cagggcagug auguugcccc ucggaagaua     60
acuauacaac cuacugccuu cccug                                           85

<210> SEQ ID NO 6
<211> LENGTH: 84
<212> TYPE: RNA
<213> ORGANISM: Homo sapiens

<400> SEQUENCE: 6
gcauccgggu ugagguagua gguuguaugg uuuagaguua cacccuggga guuaacugua     60
caaccuucua gcuuuccuug gagc                                            84

<210> SEQ ID NO 7
<211> LENGTH: 87
<212> TYPE: RNA
<213> ORGANISM: Homo sapiens

<400> SEQUENCE: 7
ccuaggaaga gguaguaggu ugcauaguuu uagggcaggg auuuugccca caaggaggua     60
acuauacgac cugcugccuu ucuuagg                                         87

<210> SEQ ID NO 8
<211> LENGTH: 85
<212> TYPE: RNA
<213> ORGANISM: Homo sapiens

<400> SEQUENCE: 8
cuaggaagag guaguaguuu gcauaguuuu agggcaaaga uuuugccac aaguaguuag      60 cuauacgacc ugcagccuuu uguag                                           85

<210> SEQ ID NO 9
<211> LENGTH: 85
<212> TYPE: RNA
<213> ORGANISM: Homo sapiens

<400> SEQUENCE: 9
cuggcugagg uaguaguuug ugcuguuggu cggguuguga cauugcccgc uguggagaua     60
acugcgcaag cuacugccuu gcuag                                           85

<210> SEQ ID NO 10
<211> LENGTH: 79
<212> TYPE: RNA
<213> ORGANISM: Homo sapiens

<400> SEQUENCE: 10
cccgggcuga gguaggaggu uguauaguug aggaggacac ccaaggagau cacuauacgg     60
ccuccuagcu uucccagg                                                   79

<210> SEQ ID NO 11
<211> LENGTH: 87
<212> TYPE: RNA
<213> ORGANISM: Homo sapiens

<400> SEQUENCE: 11
ucagagugag guaguagauu guauaguugu ggguaguga uuuuacccug uucaggagau      60
```
aacuauacaa ucuauugccu ucccuga         87

<210> SEQ ID NO 12
<211> LENGTH: 89
<212> TYPE: RNA
<213> ORGANISM: Homo sapiens

<400> SEQUENCE: 12
cugugggaug agguaguaga uuguauaguu guggggaugu gauuuuaccc uguucaggag    60
auaacuauac aaucuauugc cucccuga         89

<210> SEQ ID NO 13
<211> LENGTH: 85
<212> TYPE: RNA
<213> ORGANISM: Homo sapiens

<400> SEQUENCE: 13
cugugggaug agguaguaga uuguauaguu uuagggucau accccaucuu ggagauaacu    60
auacagucua cugucuuucc cacgg            85

<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg    60
guacaggaga uaacuguaca ggccacugcc uugccaggaa cagcgcgc               108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cggguuguga cauugcccgc uguggagaua    60
acugcgcaag cuacugccuu gcuag             85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu    60
aaagaaguau guauuuuugg uaggc             85

<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauugaac    60 auacaaugcu auggaaugua aagaaguaug uauuuuggu aggcaauua               108

<210> SEQ ID NO 18
<211> LENGTH: 85
<212> TYPE: RNA
<213> ORGANISM: Homo sapiens

```
<400> SEQUENCE: 18
gccugcuugg gaaacauacu ucuuuauaug cccauaugga ccugcuaagc uauggaaugu      60
aaagaaguau guaucucagg ccggg                                            85

<210> SEQ ID NO 19
<211> LENGTH: 71
<212> TYPE: RNA
<213> ORGANISM: Homo sapiens

<400> SEQUENCE: 19
ugggaaacau acuucuuuau augcccauau ggaccugcua agcuauggaa uguaaagaag      60
uauguaucuc a                                                           71

<210> SEQ ID NO 20
<211> LENGTH: 85
<212> TYPE: RNA
<213> ORGANISM: Homo sapiens

<400> SEQUENCE: 20
accuacucag aguacauacu ucuuuaugua cccauaugaa cauacaaugc uauggaaugu      60
aaagaaguau guauuuuugg uaggc                                            85

<210> SEQ ID NO 21
<211> LENGTH: 108
<212> TYPE: RNA
<213> ORGANISM: Homo sapiens

<400> SEQUENCE: 21
uggauguugg ccaguucug uguggaagac uagugauuuu guuguuuuua gauaacuaaa       60
ucgacaacaa aucacagucu gccauauggc acaggccaug ccucuaca                  108

<210> SEQ ID NO 22
<211> LENGTH: 110
<212> TYPE: RNA
<213> ORGANISM: Homo sapiens

<400> SEQUENCE: 22
uuggauguug gccuaguucu guguggaaga cuagugauuu uguuguuuuu agauaacuaa      60
aucgacaaca aaucacaguc ugccauaugg cacaggccau gccucuacag               110

<210> SEQ ID NO 23
<211> LENGTH: 110
<212> TYPE: RNA
<213> ORGANISM: Homo sapiens

<400> SEQUENCE: 23
cuggauacag aguggaccgg cuggccccau cuggaagacu agugauuug uuguugcuu        60 acugcgcuca acaacaaauc ccagucuacc uaauggugcc agccaucgca               110

<210> SEQ ID NO 24
<211> LENGTH: 110
<212> TYPE: RNA
<213> ORGANISM: Homo sapiens

<400> SEQUENCE: 24
agauuagagu ggcuguggu uagugcugug uggaagacua gugauuuugu uguucugaug       60
uacuacgaca caagucaca gccggccuca uagcgcagac ucccuucgac                110
```

```
<210> SEQ ID NO 25
<211> LENGTH: 89
<212> TYPE: RNA
<213> ORGANISM: Homo sapiens

<400> SEQUENCE: 25
cgggguuggu uguuaucuuu gguuaucuag cuguaugagu ggugugagu cuucauaaag      60 cuagauaacc gaaaguaaaa auaacccca                                      89

<210> SEQ ID NO 26
<211> LENGTH: 87
<212> TYPE: RNA
<213> ORGANISM: Homo sapiens

<400> SEQUENCE: 26
ggaagcgagu uguuaucuuu gguuaucuag cuguaugagu guauuggucu ucauaaagcu    60
agauaaccga aaguaaaaac uccuuca                                        87

<210> SEQ ID NO 27
<211> LENGTH: 90
<212> TYPE: RNA
<213> ORGANISM: Homo sapiens

<400> SEQUENCE: 27
ggaggcccgu uucucucuuu gguuaucuag cuguaugagu gccacagagc cgucauaaag    60
cuagauaacc gaaaguagaa augauucuca                                     90

<210> SEQ ID NO 28
<211> LENGTH: 110
<212> TYPE: RNA
<213> ORGANISM: Homo sapiens

<400> SEQUENCE: 28
gaucugucug ucuucuguau uacccugua gauccgaauu uguguaagga auuuuguggu     60
cacaaauucg uaucuagggg aauauguagu ugacauaaac acuccgcucu              110

<210> SEQ ID NO 29
<211> LENGTH: 110
<212> TYPE: RNA
<213> ORGANISM: Homo sapiens

<400> SEQUENCE: 29
ccagagguug uaacguuguc uauauauacc cuguagaacc gaauuugugu gguauccgua    60
uagucacaga uucgauucua ggggaauaua uggucgaugc aaaaacuuca              110

<210> SEQ ID NO 30
<211> LENGTH: 108
<212> TYPE: RNA
<213> ORGANISM: Homo sapiens

<400> SEQUENCE: 30
gcgcgaaugu guguuuaaaa aaauaaaac cuggaguaa aguagcagca cauaaugguu     60 ugggauuuu gaaaaggugc aggccauauu gugcugccuc aaaaauac                108

<210> SEQ ID NO 31
<211> LENGTH: 83
<212> TYPE: RNA
<213> ORGANISM: Homo sapiens

<400> SEQUENCE: 31
ccuuggagua aaguagcagc acauaauggu uuguggauuu ugaaaaggug caggccauau    60
```

```
ugugcugccu caaaaauaca agg                                             83

<210> SEQ ID NO 32
<211> LENGTH: 64
<212> TYPE: RNA
<213> ORGANISM: Homo sapiens

<400> SEQUENCE: 32
cuguagcagc acaucauggu uuacaugcua cagucaagau gcgaaucauu auuugcugcu    60
cuag                                                                  64

<210> SEQ ID NO 33
<211> LENGTH: 98
<212> TYPE: RNA
<213> ORGANISM: Homo sapiens

<400> SEQUENCE: 33
uugaggccuu aaaguacugu agcagcacau cauggnuuac augcuacagu caagaugcga    60
aucauuauuu gcugcucuag aaauuuaagg aaauucau                             98

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu    60
auuaacugug cugcugaagu aagguugac                                       89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauauuaaa caccaauauu    60 acugcugc uuuaguguga c                                                 81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuagauuc uaaaauuauc uccaguauua    60 acugcugc ugaaguaagg u                                                 81

<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga    60
aggcacuugu agcauuaugg ugac                                            84

<210> SEQ ID NO 38
<211> LENGTH: 71
<212> TYPE: RNA
<213> ORGANISM: Homo sapiens
```

```
<400> SEQUENCE: 38
uguucuaagg ugcaucuagu gcagauagug aaguagauua gcaucuacug cccuaagugc    60
uccuucuggc a                                                        71

<210> SEQ ID NO 39
<211> LENGTH: 81
<212> TYPE: RNA
<213> ORGANISM: Homo sapiens

<400> SEQUENCE: 39
uuuuuguucu aaggugcauc uagugcagau agugaaguag auuagcaucu acugcccuaa    60
gugcuccuuc uggcauaaga a                                             81

<210> SEQ ID NO 40
<211> LENGTH: 82
<212> TYPE: RNA
<213> ORGANISM: Homo sapiens

<400> SEQUENCE: 40
gcaguccucu guuaguuuug cauaguugca cuacaagaag aauguaguug ugcaaaucua    60
ugcaaaacug augguggccu gc                                            82

<210> SEQ ID NO 41
<211> LENGTH: 80
<212> TYPE: RNA
<213> ORGANISM: Homo sapiens

<400> SEQUENCE: 41
caguccucug uuaguuuugc auaguugcac uacaagaaga auguaguugu gcaaaucuau    60
gcaaaacuga ugguggccug                                               80

<210> SEQ ID NO 42
<211> LENGTH: 87
<212> TYPE: RNA
<213> ORGANISM: Homo sapiens

<400> SEQUENCE: 42 cacuguucua igguuaguuu ugcagguuug cauccagcug ugugauauuc ugcugugcaa    60
auccaugcaa aacugacugu gguagug                                       87

<210> SEQ ID NO 43
<211> LENGTH: 96
<212> TYPE: RNA
<213> ORGANISM: Homo sapiens

<400> SEQUENCE: 43
acauugcuac uuacaauuag uuuugcaggu uugcauuuca gcguauauau guauaugugg    60
cugugcaaau ccaugcaaaa cugauuguga uaaugu                             96

<210> SEQ ID NO 44
<211> LENGTH: 80
<212> TYPE: RNA
<213> ORGANISM: Homo sapiens

<400> SEQUENCE: 44
uucuaugguu aguuuugcag guuugcaucc agcuguguga uauucugcug ugcaaaucca    60
ugcaaaacug acuguggag                                                80
```

-continued

```
<210> SEQ ID NO 45
<211> LENGTH: 81
<212> TYPE: RNA
<213> ORGANISM: Homo sapiens

<400> SEQUENCE: 45
uuacaauuag uuuugcaggu uugcauuuca gcguauauau guauaugugg cugugcaaau    60
ccaugcaaaa cugauuguga u                                              81

<210> SEQ ID NO 46
<211> LENGTH: 71
<212> TYPE: RNA
<213> ORGANISM: Homo sapiens

<400> SEQUENCE: 46
guagcacuaa agugcuuaua gugcaggguag uguuuaguua ucuacugcau uaugagcacu    60
uaaaguacug c                                                         71

<210> SEQ ID NO 47
<211> LENGTH: 72
<212> TYPE: RNA
<213> ORGANISM: Homo sapiens

<400> SEQUENCE: 47
ugucggguag cuuaucagac ugauguugac uguugaaucu cauggcaaca ccagucgaug    60
ggcugucuga ca                                                        72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc    60
gaugggcugu cugacauuuu g                                              81

<210> SEQ ID NO 49
<211> LENGTH: 85
<212> TYPE: RNA
<213> ORGANISM: Homo sapiens

<400> SEQUENCE: 49
ggcugagccg caguaguucu ucagugggcaa gcuuuauguc cugacccagc uaaagcugcc    60
aguugaagaa cuguugcccu cugcc                                          85

<210> SEQ ID NO 50
<211> LENGTH: 73
<212> TYPE: RNA
<213> ORGANISM: Homo sapiens

<400> SEQUENCE: 50
ggccggcugg gguuccuggg gauggauuu gcuccuguc acaaaucaca uugccaggga    60
uuuccaaccg acc                                                       73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugugacuuaa gauuaaaauc    60
```

-continued

```
acauugccag ggauuaccac gcaaccacga ccuuggc                                    97

<210> SEQ ID NO 52
<211> LENGTH: 81
<212> TYPE: RNA
<213> ORGANISM: Homo sapiens

<400> SEQUENCE: 52
ccacggccgg cugggguucc uggggauggg auuugcuucc ugucacaaau cacauugcca           60
gggauuucca accgacccug a                                                    81

<210> SEQ ID NO 53
<211> LENGTH: 68
<212> TYPE: RNA
<213> ORGANISM: Homo sapiens

<400> SEQUENCE: 53
cuccggugcc uacugagcug auaucaguuc ucauuuuaca cacuggcuca guucagcagg           60
aacaggag                                                                   68

<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc           60
agcaggaaca ggg                                                             73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guugguuugu guacacuggc           60
ucaguucagc aggaacaggg g                                                    81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca           60
ggaacagcau c                                                               71

<210> SEQ ID NO 57
<211> LENGTH: 84
<212> TYPE: RNA
<213> ORGANISM: Homo sapiens

<400> SEQUENCE: 57
ggccaguguu gagaggcgga gacuugggca auugcuggac gcugcccugg gcauugcacu           60
ugucucgguc ugacagugcc ggcc                                                 84

<210> SEQ ID NO 58
<211> LENGTH: 86
<212> TYPE: RNA
<213> ORGANISM: Homo sapiens
```

```
<400> SEQUENCE: 58
aggccguggc cucguucaag uaauccagga uaggcugugc aggucccaau ggccuaucuu    60
gguuacuugc acgggacgc gggccu                                          86

<210> SEQ ID NO 59
<211> LENGTH: 77
<212> TYPE: RNA
<213> ORGANISM: Homo sapiens

<400> SEQUENCE: 59
guggccucgu ucaaguaauc caggauaggc ugugcagguc ccaaugggcc uauucuuggu    60
uacuugcacg gggacgc                                                   77

<210> SEQ ID NO 60
<211> LENGTH: 84
<212> TYPE: RNA
<213> ORGANISM: Homo sapiens

<400> SEQUENCE: 60
ggcuguggcu ggauucaagu aauccaggau aggcuguuuc caucugugag gccuauucuu    60
gauuacuugu uucuggaggc agcu                                           84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua    60
cuuggcucgg ggaccgg                                                   77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc agggucaaca ccaagucgug uucacagugg    60
cuaaguuccg cccccccag                                                 78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauugguuu ccgcuuuguu cacaguggcu    60
aaguucugca ccu                                                       73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uuccgcuuug    60
uucacagugg cuaaguucug caccugaaga gaaggug                             97
```

```
<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag caggguccac accaagucgu guucacagug      60
gcuaaguucc gccccccagg                                                  80

<210> SEQ ID NO 66
<211> LENGTH: 86
<212> TYPE: RNA
<213> ORGANISM: Homo sapiens

<400> SEQUENCE: 66
gguccuugcc cucaaggagc ucacagucua uugaguuacc uuucugacuu ucccacuaga      60
uugugagcuc cuggagggca ggcacu                                           86

<210> SEQ ID NO 67
<211> LENGTH: 108
<212> TYPE: RNA
<213> ORGANISM: Homo sapiens

<400> SEQUENCE: 67
ccuucuguga ccccuuagag gaugacugau uucuuuggu guucagaguc aauauaauuu       60
ucuagcacca ucugaaaucg guuauaauga uggggaaga gcaccaug                   108

<210> SEQ ID NO 68
<211> LENGTH: 64
<212> TYPE: RNA
<213> ORGANISM: Homo sapiens

<400> SEQUENCE: 68
augacugauu ucuuuggug uucagaguca auauaauuuu cuagcaccau cugaaaucgg       60
uuau                                                                   64

<210> SEQ ID NO 69
<211> LENGTH: 81
<212> TYPE: RNA
<213> ORGANISM: Homo sapiens

<400> SEQUENCE: 69
cuucaggaag cugguuucau auggugguuu agauuuaaau agugauugc uagcaccauu       60 ugaaaucagu guucuugggg g                                                81

<210> SEQ ID NO 70
<211> LENGTH: 81
<212> TYPE: RNA
<213> ORGANISM: Homo sapiens

<400> SEQUENCE: 70
cuucuggaag cugguuucac auggugggcuu agauuuuccc aucuuuguau cuagcaccau      60
uugaaaucag uguuuuagga g                                                81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc ugguguucag agucuguuuu      60
```
ugucuagcac cauuugaaau cgguuaugau guagggggaa aagcagcagc                        110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug            60
uuugcagcug c                                                                71

<210> SEQ ID NO 73
<211> LENGTH: 60
<212> TYPE: RNA
<213> ORGANISM: Homo sapiens

<400> SEQUENCE: 73
auguaaacau ccuacacuca gcuguaauac auggauuggc ugggaggugg auguuuacgu            60

<210> SEQ ID NO 74
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga           60 ggugugauguu uacuucagcu gacuugga                                              88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug           60
uuuacucuuu cu                                                               72

<210> SEQ ID NO 76
<211> LENGTH: 70
<212> TYPE: RNA
<213> ORGANISM: Homo sapiens

<400> SEQUENCE: 76
guuguuguaa acaucccga cuggaagcug uaagacacag cuaagcuuuc agucagaugu            60
uugcugcuac                                                                  70

<210> SEQ ID NO 77
<211> LENGTH: 64
<212> TYPE: RNA
<213> ORGANISM: Homo sapiens

<400> SEQUENCE: 77
cuguaaacau ccuugacugg aagcuguaag guguucagag gagcuuucag ucggauguuu           60
acag                                                                        64

<210> SEQ ID NO 78
<211> LENGTH: 71
<212> TYPE: RNA
<213> ORGANISM: Homo sapiens

<400> SEQUENCE: 78

```
ggagaggagg caagaugcug gcauagcugu ugaacuggga accugcuaug ccaacauauu    60
gccaucuuuc c                                                        71

<210> SEQ ID NO 79
<211> LENGTH: 70
<212> TYPE: RNA
<213> ORGANISM: Homo sapiens

<400> SEQUENCE: 79
ggagauauug cacauuacua aguugcaugu ugucacggcc ucaaugcaau uuagugugug    60
ugauauuuuc                                                          70

<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag    60
gcgggugcag ugccucggca gugcagcccg gagccggccc cuggcaccac              110

<210> SEQ ID NO 81
<211> LENGTH: 88
<212> TYPE: RNA
<213> ORGANISM: Homo sapiens

<400> SEQUENCE: 81
accaaguuuc aguucaugua aacaccuac acucagcugu aauacaugga uuggcuggga    60
gguggauguu uacuucagcu gacuugga                                      88

<210> SEQ ID NO 82
<211> LENGTH: 69
<212> TYPE: RNA
<213> ORGANISM: Homo sapiens

<400> SEQUENCE: 82
cuguggugca uuguaguugc auugcauguu cuggugguac ccaugcaaug uuccacagu    60 gcaucacag                                                           69

<210> SEQ ID NO 83
<211> LENGTH: 110
<212> TYPE: RNA
<213> ORGANISM: Homo sapiens

<400> SEQUENCE: 83
ggccagcugu gaguguuucu uuggcagugu cuuagcuggu uguugagc aauaguaagg     60 aagcaaucag caaguauacu gcccuagaag ugcugcacgu uguggggccc              110

<210> SEQ ID NO 84
<211> LENGTH: 84
<212> TYPE: RNA
<213> ORGANISM: Homo sapiens

<400> SEQUENCE: 84
gugcucgguu uguaggcagu gucauuagcu gauugacug uggugguuac aaucacuaac    60
uccacugcca ucaaaacaag gcac                                          84

<210> SEQ ID NO 85
<211> LENGTH: 77
```

```
<212> TYPE: RNA
<213> ORGANISM: Homo sapiens

<400> SEQUENCE: 85
agucuaguua cuaggcagug uaguuagcug auugcuaaua guaccaauca cuaaccacac    60
ggccagguaa aaagauu                                                    77

<210> SEQ ID NO 86
<211> LENGTH: 82
<212> TYPE: RNA
<213> ORGANISM: Homo sapiens

<400> SEQUENCE: 86
ucagaauaau gucaaagugc uuacagugca gguagugaua ugugcaucua cugcagugaa    60
ggcacuugua gcauuauggu ga                                              82

<210> SEQ ID NO 87
<211> LENGTH: 78
<212> TYPE: RNA
<213> ORGANISM: Homo sapiens

<400> SEQUENCE: 87
cuuucuacac agguugggau cgguugcaau gcuguguuuc uguaugguau ugcacuuguc    60
ccggccuguu gaguuugg                                                   78

<210> SEQ ID NO 88
<211> LENGTH: 75
<212> TYPE: RNA
<213> ORGANISM: Homo sapiens

<400> SEQUENCE: 88
ucaucccugg gugggauuu guugcauuac uuguguucua uauaaaguau ugcacuuguc     60
ccggccugug gaaga                                                      75

<210> SEQ ID NO 89
<211> LENGTH: 80
<212> TYPE: RNA
<213> ORGANISM: Homo sapiens

<400> SEQUENCE: 89
cugggggcuc caaagugcug uucgugcagg uagugugauu acccaaccua cugcugagcu    60
agcacuuccc gagccccgg                                                  80

<210> SEQ ID NO 90
<211> LENGTH: 81
<212> TYPE: RNA
<213> ORGANISM: Homo sapiens

<400> SEQUENCE: 90
aacacagugg gcacucaaua aaugucuguu gaauugaaau gcguuacauu caacggguau    60
uuauugagca cccacucugu g                                               81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuugc uugugucucu ccgcucugag caaucaugug     60
cagugccaau augggaaa                                                   78
```

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg    60
gauguuugca gcugccuacu                                                80

<210> SEQ ID NO 93
<211> LENGTH: 80
<212> TYPE: RNA
<213> ORGANISM: Homo sapiens

<400> SEQUENCE: 93
gugagguagu aaguuguauu guugugggu agggauauua ggcccaauu agaagauaac       60 uauacaacuu acuacuuucc                                                80

<210> SEQ ID NO 94
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgugucugug    60
gguccguguc                                                           70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu guggugaag uggaccgcac aagcucgcuu     60
cuaugggucu gugucagugu g                                              81

<210> SEQ ID NO 96
<211> LENGTH: 108
<212> TYPE: RNA
<213> ORGANISM: Homo sapiens

<400> SEQUENCE: 96
aagagagaag auauugaggc cguugccac aaacccguag auccgaacuu gugguauuag     60
uccgcacaag cuuguaucua uagguaugug ucguuaggc aaucucac                  108

<210> SEQ ID NO 97
<211> LENGTH: 80
<212> TYPE: RNA
<213> ORGANISM: Homo sapiens

<400> SEQUENCE: 97
ccuguugcca caaacccgua gauccgaacu ugugguauua guccgcacaa gcuguaucu     60 auagguaugu gucuguuagg                                                80

<210> SEQ ID NO 98
<211> LENGTH: 110
<212> TYPE: RNA
<213> ORGANISM: Homo sapiens

<400> SEQUENCE: 98

```
aggcugcccu ggcucaguua ucacagugcu gaugcugucu auucuaaagg uacaguacug    60
ugauaacuga aggauggcag ccaucuuacc uuccaucaga ggagccucac               110

<210> SEQ ID NO 99
<211> LENGTH: 57
<212> TYPE: RNA
<213> ORGANISM: Homo sapiens

<400> SEQUENCE: 99
ucaguuauca cagugcugau gcguccauu cuaaagguac aguacuguga uaacuga        57

<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugugau    60
aacugaagga uggca                                                     75

<210> SEQ ID NO 101
<211> LENGTH: 79
<212> TYPE: RNA
<213> ORGANISM: Homo sapiens

<400> SEQUENCE: 101
acugaccuuu uucgguuauc augguaccga ugcuguauau cugaaaggua caguacugug    60
auaacugaag aaugguggu                                                 79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau    60
aacugaagaa uggug                                                     75

<210> SEQ ID NO 103
<211> LENGTH: 81
<212> TYPE: RNA
<213> ORGANISM: Homo sapiens

<400> SEQUENCE: 103
cuucuggaag cugguuucac augguggcuu agauuuuucc aucuuuguau cuagcaccau    60
uugaaaucag uguuuuagga g                                              81

<210> SEQ ID NO 104
<211> LENGTH: 81
<212> TYPE: RNA
<213> ORGANISM: Homo sapiens

<400> SEQUENCE: 104
cuucaggaag cugguuucau augguggu uu agauuuaaau agugauugcu agcaccauu    60 ugaaaucagu guucuggggg g                                              81

<210> SEQ ID NO 105
<211> LENGTH: 78
<212> TYPE: RNA
<213> ORGANISM: Homo sapiens
```

```
<400> SEQUENCE: 105
uugugcuuuc agcuucuuua cagugcugcc uuguagcauu caggucaagc aacauuguac    60
agggcuauga aagaacca                                                  78

<210> SEQ ID NO 106
<211> LENGTH: 78
<212> TYPE: RNA
<213> ORGANISM: Homo sapiens

<400> SEQUENCE: 106
uacugcccuc ggcuucuuua cagugcugcc uuguugcaua uggaucaagc agcauuguac    60
agggcuauga aggcauug                                                  78

<210> SEQ ID NO 107
<211> LENGTH: 78
<212> TYPE: RNA
<213> ORGANISM: Homo sapiens

<400> SEQUENCE: 107
aaaugucaga cagcccaucg acuguguug ccaugagauu caacagucaa caucagucug     60
auaagcuacc cgacaagg                                                  78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu gugguggcug cucaugcacc acggauguuu    60
gagcaugugc uacggugucu a                                              81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu gugguggcug cuuaugcacc acggauguuu    60
gagcaugugc uauggugucu a                                              81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa    60
gcacuucuua cauuaccaug g                                              81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaugguggcc ucccgugcu accgcacugu   60 gggguacuugc ugcuccagca gg                                            82
```

```
<210> SEQ ID NO 112
<211> LENGTH: 81
<212> TYPE: RNA
<213> ORGANISM: Homo sapiens

<400> SEQUENCE: 112
cucucugcuu ucagcuucuu uacaguguug ccuuguggca uggaguucaa gcagcauugu      60
acagggcuau caaagcacag a                                               81

<210> SEQ ID NO 113
<211> LENGTH: 90
<212> TYPE: RNA
<213> ORGANISM: Homo sapiens

<400> SEQUENCE: 113
acacugcaag aacaauaagg auuuuuaggg gcauuaugac ugagucagaa aacacagcug      60
ccccugaaag ucccucauuu uucuugcugu                                      90

<210> SEQ ID NO 114
<211> LENGTH: 80
<212> TYPE: RNA
<213> ORGANISM: Homo sapiens

<400> SEQUENCE: 114
acugcaagag caauaaggau uuuuaggggc auuaugauag uggaauggaa acacaucugc      60
ccccaaaagu cccucauuuu                                                 80

<210> SEQ ID NO 115
<211> LENGTH: 85
<212> TYPE: RNA
<213> ORGANISM: Homo sapiens

<400> SEQUENCE: 115
ccuuagcaga gcuguggagu ugacaaugg uguuuguguc uaaacuauca aacgccauua       60
ucacacuaaa uagcuacugc uaggc                                           85

<210> SEQ ID NO 116
<211> LENGTH: 66
<212> TYPE: RNA
<213> ORGANISM: Homo sapiens

<400> SEQUENCE: 116
agcuguggag ugugacaaug uguuugugu ccaaacuauc aaacgccauu aucacacuaa       60
auagcu                                                                66

<210> SEQ ID NO 117
<211> LENGTH: 61
<212> TYPE: RNA
<213> ORGANISM: Homo sapiens

<400> SEQUENCE: 117
acauuauuac uuuugguacg cgcugugaca cuucaaacuc guaccgugag uaauaaugcg      60
c                                                                     61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac      60
```

```
gcggugaaug ccaagaaugg ggcug                                          85

<210> SEQ ID NO 119
<211> LENGTH: 110
<212> TYPE: RNA
<213> ORGANISM: Homo sapiens

<400> SEQUENCE: 119
aucaagauua gaggcucugc ucuccguguu cacagcggac cuugauuuaa ugucauacaa    60
uuaaggcacg cggugaaugc caagagcgga gccuacggcu gcacugaag              110

<210> SEQ ID NO 120
<211> LENGTH: 87
<212> TYPE: RNA
<213> ORGANISM: Homo sapiens

<400> SEQUENCE: 120
ugagggcccc ucugcguguu cacagcggac cuugauuuaa ugucuauaca auuaaggcac    60
gcggugaaug ccaagagagg cgccucc                                        87

<210> SEQ ID NO 121
<211> LENGTH: 68
<212> TYPE: RNA
<213> ORGANISM: Homo sapiens

<400> SEQUENCE: 121
cucugcgugu ucacagcgga ccuugauuua augucuauac aauuaaggca cgcggugaau    60
gccaagag                                                             68

<210> SEQ ID NO 122
<211> LENGTH: 67
<212> TYPE: RNA
<213> ORGANISM: Homo sapiens

<400> SEQUENCE: 122
cucuccgugu ucacagcgga ccuugauuua augucauaca auuaaggcac gcggugaaug    60
ccaagag                                                              67

<210> SEQ ID NO 123
<211> LENGTH: 86
<212> TYPE: RNA
<213> ORGANISM: Homo sapiens

<400> SEQUENCE: 123
ugccagucuc uaggucccug agacccuuua accugugagg acauccaggg ucacagguga    60
gguucuuggg agccuggcgu cuggcc                                         86

<210> SEQ ID NO 124
<211> LENGTH: 65
<212> TYPE: RNA
<213> ORGANISM: Homo sapiens

<400> SEQUENCE: 124
ggucccugag acccuuuaac cugugaggac auccaggguc acaggugagg uucuugggag    60
ccugg                                                                65

<210> SEQ ID NO 125
<211> LENGTH: 88
<212> TYPE: RNA
<213> ORGANISM: Homo sapiens
```

```
<400> SEQUENCE: 125
ugcgcuccuc ucaguccug agacccuaac uugugauguu uaccguuuaa auccacgggu      60
uaggcucuug ggagcugcga gucgugcu                                        88

<210> SEQ ID NO 126
<211> LENGTH: 89
<212> TYPE: RNA
<213> ORGANISM: Homo sapiens

<400> SEQUENCE: 126
accagacuuu uccuaguccc ugagacccua acuugugagg uauuuuagua acaucacaag      60
ucaggcucuu gggaccuagg cggagggga                                       89

<210> SEQ ID NO 127
<211> LENGTH: 85
<212> TYPE: RNA
<213> ORGANISM: Homo sapiens

<400> SEQUENCE: 127
cgcuggcgac gggacauuau uacuuuuggu acgcgcugug acacuucaaa cucguaccgu      60
gaguaauaau gcgccgucca cggca                                           85

<210> SEQ ID NO 128
<211> LENGTH: 61
<212> TYPE: RNA
<213> ORGANISM: Homo sapiens

<400> SEQUENCE: 128
acauuauuac uuuugguacg cgcugugaca cuucaaacuc guaccgugag uaauaaugcg      60
c                                                                     61

<210> SEQ ID NO 129
<211> LENGTH: 97
<212> TYPE: RNA
<213> ORGANISM: Homo sapiens

<400> SEQUENCE: 129
ugugaucacu gucccagcc ugcugaagcu cagagggcuc ugauucagaa agaucaucgg       60
auccgucuga gcuuggcugg ucggaagucu caucauc                              97

<210> SEQ ID NO 130
<211> LENGTH: 70
<212> TYPE: RNA
<213> ORGANISM: Homo sapiens

<400> SEQUENCE: 130
ccagccugcu gaagcucaga gggcucugau ucagaaagau caucggaucc gucugagcuu      60
ggcuggucgg                                                            70

<210> SEQ ID NO 131
<211> LENGTH: 82
<212> TYPE: RNA
<213> ORGANISM: Homo sapiens

<400> SEQUENCE: 131
ugagcuguug gauucggggc cguagcacug ucgagaggu uuacauuucu cacagugaac       60
cggucucuuu uucagcugcu uc                                              82
```

```
<210> SEQ ID NO 132
<211> LENGTH: 110
<212> TYPE: RNA
<213> ORGANISM: Homo sapiens

<400> SEQUENCE: 132
gcccggcagc cacugugcag ugggaagggg ggccgauaca cuguacgaga gugaguagca      60
ggucucacag ugaaccgguc ucuucccua cugugucaca cuccuaaugg               110

<210> SEQ ID NO 133
<211> LENGTH: 70
<212> TYPE: RNA
<213> ORGANISM: Homo sapiens

<400> SEQUENCE: 133
guuggauucg gggccguagc acugucugag agguuuacau uucucacagu gaaccggucu      60
cuuuuucagc                                                            70

<210> SEQ ID NO 134
<211> LENGTH: 74
<212> TYPE: RNA
<213> ORGANISM: Homo sapiens

<400> SEQUENCE: 134
uggaucuuuu ugcggucugg gcuugcuguu ccucucaaca guagucagga agcccuuacc      60
ccaaaaagua ucua                                                       74

<210> SEQ ID NO 135
<211> LENGTH: 90
<212> TYPE: RNA
<213> ORGANISM: Homo sapiens

<400> SEQUENCE: 135
ugcccuucgc gaaucuuuuu gcggucuggg cuugcuguac auaacucaau agccggaagc      60
ccuuacccca aaaagcauuu gcggagggcg                                      90

<210> SEQ ID NO 136
<211> LENGTH: 89
<212> TYPE: RNA
<213> ORGANISM: Homo sapiens

<400> SEQUENCE: 136
ugcugcuggc cagagcucuu uucacauugu gcuacugucu gcaccuguca cuagcagugc      60
aauguuaaaa gggcauuggc cguguagug                                       89

<210> SEQ ID NO 137
<211> LENGTH: 110
<212> TYPE: RNA
<213> ORGANISM: Homo sapiens

<400> SEQUENCE: 137
gccaggaggc ggguugguu guuaucuuug guuaucuagc uguaugagug guguggaguc      60
uucauaaagc uagauaaccg aaaguaaaaa uaaccccaua cacugcgcag              110

<210> SEQ ID NO 138
<211> LENGTH: 110
<212> TYPE: RNA
<213> ORGANISM: Homo sapiens

<400> SEQUENCE: 138
cacggcgcgg cagcggcacu ggcuaaggga ggcccguuuc ucucuuuggu uaucuagcug      60
```

```
<210> SEQ ID NO 139
<211> LENGTH: 72
<212> TYPE: RNA
<213> ORGANISM: Homo sapiens

<400> SEQUENCE: 139
guuguuaucu uugguuaucu agcuguauga guguauuggu cuucauaaag cuagauaacc      60
gaaaguaaaa ac                                                         72

<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu acuguggga acuggaggua      60 acagcuaca gccauggucg ccccgcagca cgcccacgcg c                         101

<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug ggaacuggag guaacagucu acagccaugg      60
ucgccc                                                                66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc      60
ccuucaacca gcuguagcua ugcauuga                                        88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu      60 uggucccuu caaccagcug uagcugugca uugauggcgc cg                        102

<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca      60
gcuguagc                                                              68

<210> SEQ ID NO 145
<211> LENGTH: 119
<212> TYPE: RNA
<213> ORGANISM: Homo sapiens
```

```
<400> SEQUENCE: 145
ccucagaaga aagaugcccc cugcucuggc uggucaaacg gaaccaaguc cgucuuccug    60
agagguuugg uccccuucaa ccagcuacag cagggcuggc aaugcccagu ccuuggaga    119

<210> SEQ ID NO 146
<211> LENGTH: 80
<212> TYPE: RNA
<213> ORGANISM: Homo sapiens

<400> SEQUENCE: 146
gcccccugcu cuggcuggcuc aaacggaacc aaguccgucu ccugagagg uuuggucccc    60 uucaaccagc uacagcaggg                                              80

<210> SEQ ID NO 147
<211> LENGTH: 73
<212> TYPE: RNA
<213> ORGANISM: Homo sapiens

<400> SEQUENCE: 147
cagggugugu gacugguuga ccagagggc augcacugug uucacccugu gggccaccua    60
gucaccaacc cuc                                                     73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu cacccugug gccaccuag    60 ucaccaaccc u                                                       71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuuauu ccuaugugau ucuacugcuc acucauauag    60
ggauuggagc cguggcgcac ggcggggaca                                   90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagcucu    60
auguagggau ggaagccaug aaauacauug ugaaaaauca                        100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca auagggauu ggagccgugg    60

<210> SEQ ID NO 152
<211> LENGTH: 97
```

```
<212> TYPE: RNA
<213> ORGANISM: Homo sapiens

<400> SEQUENCE: 152
cacucugcug uggccuaugg cuuuucauuc cuaugugauu gcugucccaa acucauguag    60
ggcuaaaagc caugggcuac agugaggggc gagcucc                            97

<210> SEQ ID NO 153
<211> LENGTH: 82
<212> TYPE: RNA
<213> ORGANISM: Homo sapiens

<400> SEQUENCE: 153
ugagcccucg gaggacucca uuuguuuuga ugauggauuc uuaugcucca ucaucgucuc    60
aaaugagucu ucagaggguu cu                                            82

<210> SEQ ID NO 154
<211> LENGTH: 62
<212> TYPE: RNA
<213> ORGANISM: Homo sapiens

<400> SEQUENCE: 154
gaggacucca uuuguuuuga ugauggauuc uuaugcucca ucaucgucuc aaaugagucu    60
uc                                                                  62

<210> SEQ ID NO 155
<211> LENGTH: 73
<212> TYPE: RNA
<213> ORGANISM: Homo sapiens

<400> SEQUENCE: 155
cuucggugac ggguauucuu ggguggauaa uacggauuac guuguuauug cuuaagaaua    60
cgcguagucg agg                                                      73

<210> SEQ ID NO 156
<211> LENGTH: 99
<212> TYPE: RNA
<213> ORGANISM: Homo sapiens

<400> SEQUENCE: 156
cccuggcaug gugguggggg gcagcuggug uugugaauca ggccguugcc aaucagagaa    60
cggcuacuuc acaacaccag ggccacacca cacuacagg                          99

<210> SEQ ID NO 157
<211> LENGTH: 84
<212> TYPE: RNA
<213> ORGANISM: Homo sapiens

<400> SEQUENCE: 157
cguugcugca gcugguguug ugaaucaggc cgacgagcag cgcauccucu acccggcua    60 uuucacgaca ccaggguugc auca                                          84

<210> SEQ ID NO 158
<211> LENGTH: 71
<212> TYPE: RNA
<213> ORGANISM: Homo sapiens

<400> SEQUENCE: 158
cagcuggugu ugugaaucag gccgacgagc agcgcauccu cuuacccggc uauuucacga    60
caccaggguu g                                                        71
```

<210> SEQ ID NO 159
<211> LENGTH: 68
<212> TYPE: RNA
<213> ORGANISM: Homo sapiens

<400> SEQUENCE: 159
guguauucua cagugcacgu gucuccagug uggcucggag gcuggagacg cggcccuguu    60
ggaguaac                                                             68

<210> SEQ ID NO 160
<211> LENGTH: 100
<212> TYPE: RNA
<213> ORGANISM: Homo sapiens

<400> SEQUENCE: 160 ugugcucuc ucugugnccu gccagugguu uuacccuaug guagguuacg ucaugcuguu     60
cuaccacagg guagaaccac ggacaggaua ccggggcacc                         100

<210> SEQ ID NO 161
<211> LENGTH: 72
<212> TYPE: RNA
<213> ORGANISM: Homo sapiens

<400> SEQUENCE: 161
uccugccagu gguuuacccc uaugguaggu uacgucaugc uguucuacca caggguagaa    60
ccacggacag ga                                                        72

<210> SEQ ID NO 162
<211> LENGTH: 70
<212> TYPE: RNA
<213> ORGANISM: Homo sapiens

<400> SEQUENCE: 162
ccugccagug guuuuacccu augguagguu acgucaugcu guucuaccac aggguagaac    60
cacggacagg                                                           70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcuccua    60
acacugucug guaaagaugg cucccgggug gguuc                               95

<210> SEQ ID NO 164
<211> LENGTH: 72
<212> TYPE: RNA
<213> ORGANISM: Homo sapiens

<400> SEQUENCE: 164
ggguccaucu uccaguacag uguuggaugg ucuaauugug aagcuccuaa cacugucugg    60
uaaagauggc cc                                                        72

<210> SEQ ID NO 165
<211> LENGTH: 64
<212> TYPE: RNA
<213> ORGANISM: Homo sapiens

<400> SEQUENCE: 165

```
acccauaaag uagaaagcac uacuaacagc acuggagggu guaguguuuc cuacuuuaug      60
gaug                                                                  64

<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucuggca guugggaguc       60 ugagaugaag cacguagcu caggaagaga gaaguuguuc ugcagc                    106

<210> SEQ ID NO 167
<211> LENGTH: 63
<212> TYPE: RNA
<213> ORGANISM: Homo sapiens

<400> SEQUENCE: 167
ccugaggugc agugcugcau cucggucag uuggagucu gagaugaagc acguagcuc        60 agg                                                                   63

<210> SEQ ID NO 168
<211> LENGTH: 86
<212> TYPE: RNA
<213> ORGANISM: Homo sapiens

<400> SEQUENCE: 168
uggggcccug gcuggauau caucauauac guaaguuug cgaugagaca cuacaguaua       60
gaugauguac uaguccgggc accccc                                          86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua    60
cuaguc                                                                66

<210> SEQ ID NO 170
<211> LENGTH: 88
<212> TYPE: RNA
<213> ORGANISM: Homo sapiens

<400> SEQUENCE: 170
caccuugucc ucacggucca guuucccag gaaucccuua gaugcuaaga uggggauucc      60
uggaaauacu guucuugagg ucauggu                                         88

<210> SEQ ID NO 171
<211> LENGTH: 70
<212> TYPE: RNA
<213> ORGANISM: Homo sapiens

<400> SEQUENCE: 171
cucacggucc aguuucccca ggaaucccuu agaugcuaag auggggauuc cuggaaauac     60
uguucuugag                                                            70

<210> SEQ ID NO 172
<211> LENGTH: 99
```

```
<212> TYPE: RNA
<213> ORGANISM: Homo sapiens

<400> SEQUENCE: 172
ccgaugugua uccucagcuu ugagaacuga auuccauggg uugugucagu gucagaccuc    60
ugaaauucag uucuucagcu gggauaucuc ugucaucgu                          99

<210> SEQ ID NO 173
<211> LENGTH: 65
<212> TYPE: RNA
<213> ORGANISM: Homo sapiens

<400> SEQUENCE: 173
agcuuugaga acugaauucc auggguugug ucagugucag accugugaaa uucaguucuu    60
cagcu                                                                65

<210> SEQ ID NO 174
<211> LENGTH: 72
<212> TYPE: RNA
<213> ORGANISM: Homo sapiens

<400> SEQUENCE: 174
aaucuaaaga caacauuucu gcacacacac cagacuaugg aagccagugu guggaaaugc    60
uucugcuaga uu                                                        72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac    60
uuugucuc                                                             68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa    60
agucagugca ucacagaacu uugcucgaa agcuuucua                            99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau                                                           70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacucccgug cuugucgag gaggaggga      60 gggacggggg cugugcuggg gcagcugga                                      89
```

<210> SEQ ID NO 179
<211> LENGTH: 53
<212> TYPE: RNA
<213> ORGANISM: Homo sapiens

<400> SEQUENCE: 179
gcucuggcuc cgucucuuca cucccgugcu uguccgagga gggagggagg gac            53

<210> SEQ ID NO 180
<211> LENGTH: 84
<212> TYPE: RNA
<213> ORGANISM: Homo sapiens

<400> SEQUENCE: 180 cucccccaugg cccugucucc caacccuugu accagugcug ggcucagacc cugguacagg    60 ccuggggac agggaccugg ggac                                            84

<210> SEQ ID NO 181
<211> LENGTH: 64
<212> TYPE: RNA
<213> ORGANISM: Homo sapiens

<400> SEQUENCE: 181
cccugucucc caacccuugu accagugcug ggcucagacc cugguacagg ccuggggac     60 aggg                                                                 64

<210> SEQ ID NO 182
<211> LENGTH: 72
<212> TYPE: RNA
<213> ORGANISM: Homo sapiens

<400> SEQUENCE: 182
uuuccugccc ucgaggagcu cacagucuag uaugucucau ccccuacuag acugaagcuc    60
cuugaggaca gg                                                        72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc    60
gagggcagg                                                            69

<210> SEQ ID NO 184
<211> LENGTH: 87
<212> TYPE: RNA
<213> ORGANISM: Homo sapiens

<400> SEQUENCE: 184
uguccccccc ggcccagguu cugugauaca cuccgacucg ggcucuggag cagucagugc    60
augacagaac uugggcccgg aaggacc                                        87

<210> SEQ ID NO 185
<211> LENGTH: 71
<212> TYPE: RNA
<213> ORGANISM: Homo sapiens

<400> SEQUENCE: 185
ggcccagguu cugugauaca cuccgacucg ggcucuggag cagucagugc augacagaac    60

```
uugggccccg g                                                         71

<210> SEQ ID NO 186
<211> LENGTH: 90
<212> TYPE: RNA
<213> ORGANISM: Homo sapiens

<400> SEQUENCE: 186
cucacagcug ccagugucau uuuugugauc ugcagcuagu auucacacuc caguugcaua    60
gucacaaaag ugaucauugg caggugugge                                    90

<210> SEQ ID NO 187
<211> LENGTH: 71
<212> TYPE: RNA
<213> ORGANISM: Homo sapiens

<400> SEQUENCE: 187
ucucucucuc ccucacagcu gccaguguca uugucacaaa agugaucauu ggcaggugug    60
gcugcugcau g                                                        71

<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc aguugcauag    60
ucacaaaagu gaucauugga aacugug                                       87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag    60
ugaucauug                                                           69

<210> SEQ ID NO 190
<211> LENGTH: 84
<212> TYPE: RNA
<213> ORGANISM: Homo sapiens

<400> SEQUENCE: 190
gugguacuug aagauagguu auccguguug ccuucgcuuu auuugugacg aaucauacac    60
gguugaccua uuuuucagua ccaa                                          84

<210> SEQ ID NO 191
<211> LENGTH: 66
<212> TYPE: RNA
<213> ORGANISM: Homo sapiens

<400> SEQUENCE: 191
gaagauaggu uaccguguu gccuucgcuu uauuugugac gaaucauaca cgguugaccu     60
auuuuu                                                              66

<210> SEQ ID NO 192
<211> LENGTH: 65
<212> TYPE: RNA
<213> ORGANISM: Homo sapiens
```

```
<400> SEQUENCE: 192
cuguuaaugc uaaucgugau aggggguuuuu gccuccaacu gacuccuaca uauuagcauu    60
aacag                                                                65

<210> SEQ ID NO 193
<211> LENGTH: 82
<212> TYPE: RNA
<213> ORGANISM: Homo sapiens

<400> SEQUENCE: 193
ccuaacacug ucugguaaag auggcucccg ggugggauucu cucggcagua accuucaggg    60
agcccugaag accauggagg ac                                             82

<210> SEQ ID NO 194
<211> LENGTH: 110
<212> TYPE: RNA
<213> ORGANISM: Homo sapiens

<400> SEQUENCE: 194
gccgagaccg agugcacagg gcucugaccu augaauugac agccagugcu cucgucuccc    60
cucuggcugc caauuccaua ggucacaggu auguucgccu caaugccagc                110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cgguuccag ugggcugcu      60 guuaucuggg gcgagggcca                                                80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucugggcuac gcuaugcugc    60
ggcgcucggg                                                           70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgagucccca cccggggauaa agaaaggccg  60 aauu                                                                 64

<210> SEQ ID NO 198
<211> LENGTH: 70
<212> TYPE: RNA
<213> ORGANISM: Homo sapiens

<400> SEQUENCE: 198
ccuaagccag ggauugugggg uucgagucccc accuggggua gaggugaaag uuccuuuuac  60
ggaauuuuuu                                                           70
```

```
<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc      60
caguauuaac ugugcugcug aaguaagguu gaccauacuc uacaguug                 108

<210> SEQ ID NO 200
<211> LENGTH: 81
<212> TYPE: RNA
<213> ORGANISM: Homo sapiens

<400> SEQUENCE: 200
gggcuuucaa gucacuagug guuccguuua guagaugauu ugcauuguu ucaaaauggu      60 gcccuaguga cuacaaagcc c                                              81

<210> SEQ ID NO 201
<211> LENGTH: 70
<212> TYPE: RNA
<213> ORGANISM: Homo sapiens

<400> SEQUENCE: 201
acgcaagugu ccuaagguga gcucagggag cacagaaacc uccaguggaa cagaagggca      60
aaagcucauu                                                           70

<210> SEQ ID NO 202
<211> LENGTH: 70
<212> TYPE: RNA
<213> ORGANISM: Homo sapiens

<400> SEQUENCE: 202
caugugucac uuucaggugg aguuucaaga gucccuuccu gguucaccgu cuccuuugcu      60
cuuccacaac                                                           70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag      60
uuugggauuu gaaaaaacca cugaccguug acuguaccuu ggggguccuua              110

<210> SEQ ID NO 204
<211> LENGTH: 110
<212> TYPE: RNA
<213> ORGANISM: Homo sapiens

<400> SEQUENCE: 204
ccugugcaga gauuauuuuu uaaaagguca caaucaacau ucauugcugu cgguggguug      60 aacuguguugg acaagcucac ugaacaauga augcaacugu ggccccgcuu              110

<210> SEQ ID NO 205
<211> LENGTH: 89
<212> TYPE: RNA
<213> ORGANISM: Homo sapiens

<400> SEQUENCE: 205
cugauggcug cacucaacau ucauugcugu cgguggguuu gagucugaau caacucacug      60
```
aucaaugaau gcaaacugcg gaccaaaca                                              89

<210> SEQ ID NO 206
<211> LENGTH: 110
<212> TYPE: RNA
<213> ORGANISM: Homo sapiens

<400> SEQUENCE: 206
cggaaaauuu gccaaggguu uggggaaca uucaaccugu cggugaguuu gggcagcuca             60
ggcaaaccau cgaccguuga guggacccug aggccuggaa uugccauccu                      110

<210> SEQ ID NO 207
<211> LENGTH: 110
<212> TYPE: RNA
<213> ORGANISM: Homo sapiens

<400> SEQUENCE: 207
gagcugcuug ccuccccccg uuuuuggcaa ugguagaacu cacacuggug agguaacagg            60
auccgguggu ucuagacuug ccaacuaugg ggcgaggacu cagccggcac                      110

<210> SEQ ID NO 208
<211> LENGTH: 70
<212> TYPE: RNA
<213> ORGANISM: Homo sapiens

<400> SEQUENCE: 208
uuuuuggcaa ugguagaacu cacacuggug agguaacagg auccgguggu ucuagacuug            60
ccaacuaugg                                                                  70

<210> SEQ ID NO 209
<211> LENGTH: 110
<212> TYPE: RNA
<213> ORGANISM: Homo sapiens

<400> SEQUENCE: 209
ccgcagagug ugacuccugu ucuguguaug gcacugguag aauucacugu gaacagucuc            60
agucagugaa uuaccgaagg gccauaaaca gagcagagac agauccacga                      110

<210> SEQ ID NO 210
<211> LENGTH: 84
<212> TYPE: RNA
<213> ORGANISM: Homo sapiens

<400> SEQUENCE: 210
ccagucacgu ccccuuauca cuuuuccagc ccagcuuugu gacuguaagu guuggacgga            60
gaacugauaa ggguagguga uuga                                                  84

<210> SEQ ID NO 211
<211> LENGTH: 65
<212> TYPE: RNA
<213> ORGANISM: Homo sapiens

<400> SEQUENCE: 211
ccuuaucacu uuuccagccc agcuuuguga cuguaagugu uggacggaga acugauaagg            60
guagg                                                                       65

<210> SEQ ID NO 212
<211> LENGTH: 82
<212> TYPE: RNA
<213> ORGANISM: Homo sapiens

```
<400> SEQUENCE: 212 aggggggcgag ggauuggaga gaaaggcagu uccugauggu ccccuccccca ggggcuggcu    60 uuccucuggu ccuucccucc ca                                              82

<210> SEQ ID NO 213
<211> LENGTH: 66
<212> TYPE: RNA
<213> ORGANISM: Homo sapiens

<400> SEQUENCE: 213
agggauugga gagaaaggca guuccugaug gucccccuccc caggggcugg cuuuccucug    60
guccuu                                                                66

<210> SEQ ID NO 214
<211> LENGTH: 86
<212> TYPE: RNA
<213> ORGANISM: Homo sapiens

<400> SEQUENCE: 214
ugcuuguaac uuccaaaga auucuccuuu ugggcuuucu gguuuauuu uaagcccaaa        60 ggugaauuuu uugggaaguu ugagcu                                          86

<210> SEQ ID NO 215
<211> LENGTH: 71
<212> TYPE: RNA
<213> ORGANISM: Homo sapiens

<400> SEQUENCE: 215
acuuuccaaa gaauucuccu uugggcuuu cugguuuuau uuuaagccca aaggugaauu      60
uuuugggaag u                                                          71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug     60 cucugaccccc ucgugucuug uguugcagcc ggagggacgc agguccgca                109

<210> SEQ ID NO 217
<211> LENGTH: 86
<212> TYPE: RNA
<213> ORGANISM: Homo sapiens

<400> SEQUENCE: 217
ugcucccucu cucacauccc uugcauggug gagggugagc uuucugaaaa ccccucccac     60 augcagggu ugcaggaugg cgagcc                                           86

<210> SEQ ID NO 218
<211> LENGTH: 68
<212> TYPE: RNA
<213> ORGANISM: Homo sapiens

<400> SEQUENCE: 218
ucucacaucc cuugcauggu ggagggugag cuuucugaaa accccuccca caugcagggu    60
uugcagga                                                              68
```

```
<210> SEQ ID NO 219
<211> LENGTH: 102
<212> TYPE: RNA
<213> ORGANISM: Homo sapiens

<400> SEQUENCE: 219
cugucgauug dacccgcccu ccggugccua cugagcugau aucaguucuc auuuuacaca      60
cuggcucagu ucagcaggaa caggagucga gcccuugagc aa                       102

<210> SEQ ID NO 220
<211> LENGTH: 68
<212> TYPE: RNA
<213> ORGANISM: Homo sapiens

<400> SEQUENCE: 220
cuccggugcc uacugagcug auaucaguuc ucauuuuaca cacuggcuca guucagcagg      60
aacaggag                                                              68

<210> SEQ ID NO 221
<211> LENGTH: 85
<212> TYPE: RNA
<213> ORGANISM: Homo sapiens

<400> SEQUENCE: 221
ugcaggccuc ugugugauau guuugauaua uuagguuguu auuuaaucca acuauauauc      60
aaacauauuc cuacaguguc uugcc                                           85

<210> SEQ ID NO 222
<211> LENGTH: 67
<212> TYPE: RNA
<213> ORGANISM: Homo sapiens

<400> SEQUENCE: 222
cugugugaua uguuugauau auuagguugu uauuuaaucc aacuauauau caaacauauu      60
ccuacag                                                               67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucccagag cauuccagcu       60 gcgcuuggau uucgucccu gcucuccugc cu                                    92

<210> SEQ ID NO 224
<211> LENGTH: 74
<212> TYPE: RNA
<213> ORGANISM: Homo sapiens

<400> SEQUENCE: 224
agcgggcaac ggaaucccaa aagcagcugu ugucccaga gcauuccagc ugcgcuugga       60
uuucgucccc ugcu                                                       74

<210> SEQ ID NO 225
<211> LENGTH: 108
<212> TYPE: RNA
<213> ORGANISM: Homo sapiens

<400> SEQUENCE: 225
ccgagaccga gugcacaggg cucugaccua ugaauugaca gccagugcuc ucgucucccc      60
```

```
ucuggcugcc aauuccauag gucacaggua uguucgccuc aaugccag              108

<210> SEQ ID NO 226
<211> LENGTH: 110
<212> TYPE: RNA
<213> ORGANISM: Homo sapiens

<400> SEQUENCE: 226
gccgagaccg agugcacagg gcucugaccu augaauugac agccagugcu cucgucuccc   60
cucuggcugc caauuccaua ggucacaggu auguucgccu caaugccagc            110

<210> SEQ ID NO 227
<211> LENGTH: 88
<212> TYPE: RNA
<213> ORGANISM: Homo sapiens

<400> SEQUENCE: 227
cgaggauggg agcugagggc ugggucuuug cgggcgagau gagggugucg gaucaacugg   60
ccuacaaagu cccaguucuc ggcccccg                                    88

<210> SEQ ID NO 228
<211> LENGTH: 58
<212> TYPE: RNA
<213> ORGANISM: Homo sapiens

<400> SEQUENCE: 228
gcugggucuu ugcgggcgag augagggugu cggaucaacu ggccuacaaa gucccagu     58

<210> SEQ ID NO 229
<211> LENGTH: 85
<212> TYPE: RNA
<213> ORGANISM: Homo sapiens

<400> SEQUENCE: 229
augguguuau caaguguaac agcaacucca ugggacugu guaccaauuu ccaguggaga    60
ugcuguuacu uuugaugguu accaa                                       85

<210> SEQ ID NO 230
<211> LENGTH: 63
<212> TYPE: RNA
<213> ORGANISM: Homo sapiens

<400> SEQUENCE: 230
guguaacagc aacuccaugu ggacugugua ccaauuucca guggaugc uguuacuuuu     60 gau                                                               63

<210> SEQ ID NO 231
<211> LENGTH: 87
<212> TYPE: RNA
<213> ORGANISM: Homo sapiens

<400> SEQUENCE: 231
agcuucccug gcucuagcag cacagaaaua uuggcacagg aagcgaguc ugccaauauu    60 ggcugugcug uccaggcag gguggug                                      87

<210> SEQ ID NO 232
<211> LENGTH: 58
<212> TYPE: RNA
<213> ORGANISM: Homo sapiens

<400> SEQUENCE: 232
```

```
uagcagcaca gaaauauugg cacagggaag cgagucugcc aauauuggcu gugcugcu        58
```

<210> SEQ ID NO 233
<211> LENGTH: 110
<212> TYPE: RNA
<213> ORGANISM: Homo sapiens

<400> SEQUENCE: 233

```
cuagagcuug aauuggaacu gcugagugaa uuagguaguu cauguuguu gggccugggu       60 uucugaacac aacaacauua aaccacccga uucacggcag uuacugcucc                110
```

<210> SEQ ID NO 234
<211> LENGTH: 70
<212> TYPE: RNA
<213> ORGANISM: Homo sapiens

<400> SEQUENCE: 234

```
gugaauuagg uaguucaug uuguugggcc uggguuucug aacacaacaa cauuaaacca       60
cccgauucac                                                            70
```

<210> SEQ ID NO 235
<211> LENGTH: 110
<212> TYPE: RNA
<213> ORGANISM: Homo sapiens

<400> SEQUENCE: 235

```
ugcucgcuca gcugaucugu ggcuuaggua guucauguu guugggauug aguuuugaac       60
ucggcaacaa gaaacugccu gaguuacauc agucgguuuu cgucgagggc               110
```

<210> SEQ ID NO 236
<211> LENGTH: 70
<212> TYPE: RNA
<213> ORGANISM: Homo sapiens

<400> SEQUENCE: 236

```
gugaauuagg uaguucaug uuguugggcc uggguuucug aacacaacaa cauuaaacca       60
cccgauucac                                                            70
```

<210> SEQ ID NO 237
<211> LENGTH: 84
<212> TYPE: RNA
<213> ORGANISM: Homo sapiens

<400> SEQUENCE: 237

```
acuggucggu gauuuaggua guuuccuguu guugggaucc accuuucucu cgacagcacg      60
acacugccuu cauuacuuca guug                                            84
```

<210> SEQ ID NO 238
<211> LENGTH: 75
<212> TYPE: RNA
<213> ORGANISM: Homo sapiens

<400> SEQUENCE: 238

```
ggcugugccg gguagagagg gcaguggag guaagagcuc uucacccuuc accaccuucu       60
ccacccagca uggcc                                                      75
```

<210> SEQ ID NO 239
<211> LENGTH: 60
<212> TYPE: RNA
<213> ORGANISM: Homo sapiens

```
<400> SEQUENCE: 239
gugcaugugu auguaugugu gcaugugcau guguaugugu augagugcau gcgugugugc    60

<210> SEQ ID NO 240
<211> LENGTH: 62
<212> TYPE: RNA
<213> ORGANISM: Homo sapiens

<400> SEQUENCE: 240
ucauuggucc agagggggaga uagguuccug ugauuuucc uucuucucua uagaauaaau    60
ga                                                                   62

<210> SEQ ID NO 241
<211> LENGTH: 71
<212> TYPE: RNA
<213> ORGANISM: Homo sapiens

<400> SEQUENCE: 241
gccaacccag uguucagacu accuguucag gaggcucuca auguguacag uagucugcac    60
auugguuagg c                                                         71

<210> SEQ ID NO 242
<211> LENGTH: 110
<212> TYPE: RNA
<213> ORGANISM: Homo sapiens

<400> SEQUENCE: 242
aggaagcuuc uggagauccu gcuccgucgc cccaguguuc agacuaccug uucaggacaa    60
ugccguugua caguagucug cacauugguu agacugggca agggagagca              110

<210> SEQ ID NO 243
<211> LENGTH: 110
<212> TYPE: RNA
<213> ORGANISM: Homo sapiens

<400> SEQUENCE: 243
ccagaggaca ccuccacucc gucuacccag uguuuagacu aucuguucag gacucccaaa    60
uuguacagua gucugcacau ugguuaggcu gggcuggguu agacccucgg              110

<210> SEQ ID NO 244
<211> LENGTH: 71
<212> TYPE: RNA
<213> ORGANISM: Homo sapiens

<400> SEQUENCE: 244
gccaacccag uguucagacu accuguucag gaggcucuca auguguacag uagucugcac    60
auugguuagg c                                                         71

<210> SEQ ID NO 245
<211> LENGTH: 70
<212> TYPE: RNA
<213> ORGANISM: Homo sapiens

<400> SEQUENCE: 245
gccguggcca cuuacugggg cagcauugga uggagucagg ucucuaauac ugccgguaa     60 ugaugacggc                                                           70

<210> SEQ ID NO 246
<211> LENGTH: 95
```

<212> TYPE: RNA
<213> ORGANISM: Homo sapiens

<400> SEQUENCE: 246
ccagcucggg cagccguggc caucuuacug ggcagcauug gauggaguca ggucucuaau    60
acugccuggu aaugaugacg gcggagcccu gcacg                              95

<210> SEQ ID NO 247
<211> LENGTH: 68
<212> TYPE: RNA
<213> ORGANISM: Homo sapiens

<400> SEQUENCE: 247
cccucgucuu acccagcagu guuuggguge gguuggagu cucuaauacu gccggguaau    60
gauggagg                                                           68

<210> SEQ ID NO 248
<211> LENGTH: 72
<212> TYPE: RNA
<213> ORGANISM: Homo sapiens

<400> SEQUENCE: 248
guuccuuuuu ccuaugcaua uacuucuuug aggaucuggc cuaaagaggu auagggcaug    60
ggaagaugga gc                                                      72

<210> SEQ ID NO 249
<211> LENGTH: 110
<212> TYPE: RNA
<213> ORGANISM: Homo sapiens

<400> SEQUENCE: 249 guguuggga cucgcgcgcu ggguccagug guucuuaaca guucaacagu ucuguagcgc    60
aauugugaaa uguuuaggac cacuagaccc ggcgggcgcg gcgacagcga              110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuucccuuu gucauccuau gccugagaau    60
auaugaagga ggcuggggaag gcaaagggac guucaauugu caucacuggc             110

<210> SEQ ID NO 251
<211> LENGTH: 110
<212> TYPE: RNA
<213> ORGANISM: Homo sapiens

<400> SEQUENCE: 251
aaagauccuc agacaaucca ugugcuucuc uugccuuca uuccaccgga gucugucuca    60
uacccaacca gauuucagug gagugaaguu caggaggcau ggagcugaca              110

<210> SEQ ID NO 252
<211> LENGTH: 86
<212> TYPE: RNA
<213> ORGANISM: Homo sapiens

<400> SEQUENCE: 252
ugcuucccga ggccacaugc uucuuuauau cccauaugg auuacuuugc uauggaaugu    60
aaggaagugu gugguuucgg caagug                                       86

<210> SEQ ID NO 253
<211> LENGTH: 69
<212> TYPE: RNA
<213> ORGANISM: Homo sapiens

<400> SEQUENCE: 253
aggccacaug cuucuuuaua uccccauaug gauuacuuug cuauggaaug uaaggaagug    60
ugugguuuu                                                           69

<210> SEQ ID NO 254
<211> LENGTH: 71
<212> TYPE: RNA
<213> ORGANISM: Homo sapiens

<400> SEQUENCE: 254
ugacgggcga gcuuuggcc cggguuauac cugaugcuca cguauaagac gagcaaaaag    60
cuuguugguc a                                                        71

<210> SEQ ID NO 255
<211> LENGTH: 110
<212> TYPE: RNA
<213> ORGANISM: Homo sapiens

<400> SEQUENCE: 255
acccggcagu gccuccaggc gcagggcagc cccugcccac cgcacacugc gcugcccag     60 acccacugug cgugugacag cggcugaucu gugccugggc agcgcgaccc              110

<210> SEQ ID NO 256
<211> LENGTH: 110
<212> TYPE: RNA
<213> ORGANISM: Homo sapiens

<400> SEQUENCE: 256
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 257
<211> LENGTH: 110
<212> TYPE: RNA
<213> ORGANISM: Homo sapiens

<400> SEQUENCE: 257
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 258
<211> LENGTH: 110
<212> TYPE: RNA
<213> ORGANISM: Homo sapiens

<400> SEQUENCE: 258
ccugugcaga gauuauuuuu uaaaagguca caaucaacau ucauugcugu cggugggguug   60 aacugugugg acaagcucac ugaacaauga augcaacugu ggccccgcuu              110

<210> SEQ ID NO 259
<211> LENGTH: 108
<212> TYPE: RNA
<213> ORGANISM: Homo sapiens

<400> SEQUENCE: 259

```
gaguuuugag guugcuucag ugaacauuca acgcugucgg ugaguuugga auuaaaauca      60
aaaccaucga ccguugauug uacccuaugg cuaaccauca ucuacucc                  108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc      60
gcucaccugu acagcaggca cagacaggca gucacaugac aacccagccu                110

<210> SEQ ID NO 261
<211> LENGTH: 110
<212> TYPE: RNA
<213> ORGANISM: Homo sapiens

<400> SEQUENCE: 261
aucauucaga aauggauauac aggaaaauga ccuaugaauu gacagacaau auagcugagu     60
uugucuguca uuucuuuagg ccaauauucu guaugacugu gcuacuucaa                110

<210> SEQ ID NO 262
<211> LENGTH: 110
<212> TYPE: RNA
<213> ORGANISM: Homo sapiens

<400> SEQUENCE: 262
gauggcugug aguuggcuua aucucagcug gcaacuguga gauguucaua caaucccuca      60 cagugguccuc ugggauuaug cuaaacagag caauuuccua gcccucacga              110

<210> SEQ ID NO 263
<211> LENGTH: 110
<212> TYPE: RNA
<213> ORGANISM: Homo sapiens

<400> SEQUENCE: 263
aguauaauua uuacauaguu uuugaugucg cagauacugc aucaggaacu gauuggauaa      60
gaaucaguca ccaucaguuc cuaaugcauu gccuucagca ucuaaacaag                110

<210> SEQ ID NO 264
<211> LENGTH: 110
<212> TYPE: RNA
<213> ORGANISM: Homo sapiens

<400> SEQUENCE: 264
gugauaaugu agcgagauuu ucuguugugc uugaucuaac cauggguug cgagguauga       60 guaaaacaug guuccgucaa gcaccaugga acgucacgca gcuuucuaca                110

<210> SEQ ID NO 265
<211> LENGTH: 110
<212> TYPE: RNA
<213> ORGANISM: Homo sapiens

<400> SEQUENCE: 265
gaccagucgc ugcggggcuu uccuuugugc uugaucuaac cauggguggg aacgauggaa      60
acggaacaug guucugucaa gcaccgcgga aagcaccgug cucuccugca                110

<210> SEQ ID NO 266
<211> LENGTH: 110
```

```
<212> TYPE: RNA
<213> ORGANISM: Homo sapiens

<400> SEQUENCE: 266
ccgccccggg ccgcggcucc ugauugucca aacgcaauuc ucgagucuau ggcuccggcc      60
gagaguugag ucuggacguc ccgagccgcc gcccccaaac cucgagcggg                110

<210> SEQ ID NO 267
<211> LENGTH: 110
<212> TYPE: RNA
<213> ORGANISM: Homo sapiens

<400> SEQUENCE: 267
ccgccccggg ccgcggcucc ugauugucca aacgcaauuc ucgagucuau ggcuccggcc      60
gagaguugag ucuggacguc ccgagccgcc gcccccaaac cucgagcggg                110

<210> SEQ ID NO 268
<211> LENGTH: 97
<212> TYPE: RNA
<213> ORGANISM: Homo sapiens

<400> SEQUENCE: 268
acucaggggc uucgccacug auuguccaaa cgcaauucuu guacgagucu gcggccaacc      60
gagaauugug gcuggacauc uguggcugag cuccggg                              97

<210> SEQ ID NO 269
<211> LENGTH: 110
<212> TYPE: RNA
<213> ORGANISM: Homo sapiens

<400> SEQUENCE: 269
gacagugugg cauuguaggg cuccacaccg uaucugacac uuugggcgag ggcaccaugc      60
ugaaggucuu caugaugcgg ucugggaacu ccucacggau cuuacugaug              110

<210> SEQ ID NO 270
<211> LENGTH: 110
<212> TYPE: RNA
<213> ORGANISM: Homo sapiens

<400> SEQUENCE: 270
ugaacaucca ggucuggggc augaaccugg cauacaaugu agauuucugu guucguuagg      60
caacagcuac auugucugcu ggguuucagg cuaccuggaa acauguucuc              110

<210> SEQ ID NO 271
<211> LENGTH: 110
<212> TYPE: RNA
<213> ORGANISM: Homo sapiens

<400> SEQUENCE: 271
gcugcuggaa gguguaggua ccccucaaugg cucaguagcc aguguagauc cugucuuucg     60
uaaucagcag cuacaucugg cuacgggguc ucgauggca ucuucuagcu                110

<210> SEQ ID NO 272
<211> LENGTH: 110
<212> TYPE: RNA
<213> ORGANISM: Homo sapiens

<400> SEQUENCE: 272
ccuggccucc ugcagugcca cgcuccgugu auuugacaag cugaguugga cacuccaugu      60
gguagagugu caguuuguca aauaccccaa gugcggcaca ugcuuaccag                110
```

<210> SEQ ID NO 273
<211> LENGTH: 81
<212> TYPE: RNA
<213> ORGANISM: Homo sapiens

<400> SEQUENCE: 273
gggcuuucaa gucacuagug guuccguuua guagaugauu gugcauuguu ucaaaauggu    60
gcccuaguga cuacaaagcc c                                             81

<210> SEQ ID NO 274
<211> LENGTH: 60
<212> TYPE: RNA
<213> ORGANISM: Homo sapiens

<400> SEQUENCE: 274
caaucuuccu uuaucauggu auugauuuuu cagugcuucc cuuuugugug agagaagaua    60

<210> SEQ ID NO 275
<211> LENGTH: 80
<212> TYPE: RNA
<213> ORGANISM: Homo sapiens

<400> SEQUENCE: 275
aggacccuuc cagagggccc ccccucaauc cuguugugcc uaauucagag gguuggugg    60 aggcucuccu gaagggcucu                                               80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua gugggaugg uaaaccgcuu     60 cuu                                                                 63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua    60
guauugucaa agcaucugaa agcagg                                        86

<210> SEQ ID NO 278
<211> LENGTH: 69
<212> TYPE: RNA
<213> ORGANISM: Homo sapiens

<400> SEQUENCE: 278
ccaccacuua aacguggaug uacuugcuuu gaaacuaaag aaguaagugc uuccauguuu    60
uggugaugg                                                           69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucugugacuu uaaaaguaag ugcuuccaug    60

-continued

```
<210> SEQ ID NO 280
<211> LENGTH: 68
<212> TYPE: RNA
<213> ORGANISM: Homo sapiens

<400> SEQUENCE: 280
ccuuugcuuu aacauggggg uaccugcugu gugaaacaaa aguaagugcu uccauguuuc      60
aguggagg                                                              68

<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu      60
gagugugg                                                              68

<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcuggguug      60
agagggcgaa aaaggaugag gu                                              82

<210> SEQ ID NO 283
<211> LENGTH: 59
<212> TYPE: RNA
<213> ORGANISM: Homo sapiens

<400> SEQUENCE: 283
uuggccuccu aagccaggga uuguggguuc gagucccacc cgggguaaag aaaggccga      59

<210> SEQ ID NO 284
<211> LENGTH: 86
<212> TYPE: RNA
<213> ORGANISM: Homo sapiens

<400> SEQUENCE: 284
uugguacuug gagagaggug guccguggcg cguucgcuuu auuuauggcg cacauuacac      60
ggucgaccuc uuugcaguau cuaauc                                          86

<210> SEQ ID NO 285
<211> LENGTH: 83
<212> TYPE: RNA
<213> ORGANISM: Homo sapiens

<400> SEQUENCE: 285
cugacuaugc cuccccgcau ccccuagggc auugguguaa agcuggagac ccacugcccc      60
aggugcugcu ggggguugua guc                                             83

<210> SEQ ID NO 286
<211> LENGTH: 98
<212> TYPE: RNA
<213> ORGANISM: Homo sapiens

<400> SEQUENCE: 286
```
uuuuaguagg agu    73

```
auacagugcu ugguuccuag uaggugucca guaaguguuu gugacauaau uuguuuauug    60
aggaccuccu aucaaucaag cacugugcua ggcucugg                           98

<210> SEQ ID NO 287
<211> LENGTH: 95
<212> TYPE: RNA
<213> ORGANISM: Homo sapiens

<400> SEQUENCE: 287
cucaucuguc uguugggcug gaggcagggc cuuugugaag gcgggugguc ucagaucgc    60 cucugggccc uuccuccagc cccgaggcgg auuca                             95

<210> SEQ ID NO 288
<211> LENGTH: 75
<212> TYPE: RNA
<213> ORGANISM: Homo sapiens

<400> SEQUENCE: 288
uggagugggg gggcaggagg ggcucaggga gaaagugcau acagccccug gcccucucug    60
cccuuccguc cccug                                                   75

<210> SEQ ID NO 289
<211> LENGTH: 94
<212> TYPE: RNA
<213> ORGANISM: Homo sapiens

<400> SEQUENCE: 289
cuuuggcgau cacugccucu cugggccugu gcuuaggcu cugcaagauc aaccgagcaa    60
agcacacggc cugcagagag gcagcgcucu gccc                              94

<210> SEQ ID NO 290
<211> LENGTH: 94
<212> TYPE: RNA
<213> ORGANISM: Homo sapiens

<400> SEQUENCE: 290
gaguuugguu uuguuugggu uuguucuagg uauggucccc gggaucccag aucaaaccag    60
gccccugggc cuauccuaga accaaccuaa gcuc                              94

<210> SEQ ID NO 291
<211> LENGTH: 94
<212> TYPE: RNA
<213> ORGANISM: Homo sapiens

<400> SEQUENCE: 291 uguuugagc gggggucaag agcaauaacg aaaaauguuu gucauaaacc guuuucauu    60 auugcuccug accuccucuc auuugcuaua uuca                              94

<210> SEQ ID NO 292
<211> LENGTH: 93
<212> TYPE: RNA
<213> ORGANISM: Homo sapiens

<400> SEQUENCE: 292
guagucagua guugggggu gggaacggcu ucauacagga guugaugcac aguuauccag    60
cuccuauaug augccuuucu ucaucccuu caa                                93

<210> SEQ ID NO 293
<211> LENGTH: 67
```

```
<212> TYPE: RNA
<213> ORGANISM: Homo sapiens

<400> SEQUENCE: 293
ucuccaacaa uauccuggug cugagugaug acucaggcga cuccagcauc agugauuuug    60
uugaaga                                                              67

<210> SEQ ID NO 294
<211> LENGTH: 94
<212> TYPE: RNA
<213> ORGANISM: Homo sapiens

<400> SEQUENCE: 294
cggggcggcc gcucucccug uccuccagga gcucacgugu gccugccugu gagcgccucg    60
acgacagagc cggcgccugc cccagugucu gcgc                                94

<210> SEQ ID NO 295
<211> LENGTH: 95
<212> TYPE: RNA
<213> ORGANISM: Homo sapiens

<400> SEQUENCE: 295
uuguaccugg ugugauuaua aagcaaugag acugauuguc auaugucguu ugugggaucc    60
gucucaguua cuuuauagcc auaccuggua ucuua                               95

<210> SEQ ID NO 296
<211> LENGTH: 99
<212> TYPE: RNA
<213> ORGANISM: Homo sapiens

<400> SEQUENCE: 296
gaaacugggc ucaaggugag gggugcuauc ugugauugag ggacaugguu aauggaauug    60
ucucacacag aaaucgcacc cgucaccuug gccuacuua                           99

<210> SEQ ID NO 297
<211> LENGTH: 98
<212> TYPE: RNA
<213> ORGANISM: Homo sapiens

<400> SEQUENCE: 297
acccaaaccc uaggucugcu gacuccuagu ccagggcucg ugauggcugg ugggcccuga    60 acgaggqquc uggaggccug gguuugaaua ucgacagc                            98

<210> SEQ ID NO 298
<211> LENGTH: 86
<212> TYPE: RNA
<213> ORGANISM: Homo sapiens

<400> SEQUENCE: 298 gucgucugc ccgcaugccu gcccucugu ugcucugaag gaggcagggg cugggccugc      60
agcugccugg gcagagcggc uccugc                                         86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau    60
ggugaugg                                                             68
```

<210> SEQ ID NO 300
<211> LENGTH: 66
<212> TYPE: RNA
<213> ORGANISM: Homo sapiens

<400> SEQUENCE: 300
aaaaggugga uauuccuucu auguuuaugu uauuuauggu uaaacauaga ggaaauucca    60
cguuuu    66

<210> SEQ ID NO 301
<211> LENGTH: 70
<212> TYPE: RNA
<213> ORGANISM: Homo sapiens

<400> SEQUENCE: 301
uugaagggag aucgaccgug uuauauucgc uuuauugacu ucgaauaaua caugguugau    60
cuuuucucag    70

<210> SEQ ID NO 302
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug    60
gaaccugguc ugucu    75

<210> SEQ ID NO 303
<211> LENGTH: 67
<212> TYPE: RNA
<213> ORGANISM: Homo sapiens

<400> SEQUENCE: 303
guggcacuca aacugugggg gcacuuucug cucucuggug aaagugccgc caucuuuuga    60
guguuac    67

<210> SEQ ID NO 304
<211> LENGTH: 67
<212> TYPE: RNA
<213> ORGANISM: Homo sapiens

<400> SEQUENCE: 304
gugggccuca aauguggagc acuauucuga uguccaagug gaaagugcug cgacauuuga    60
gcgucac    67

<210> SEQ ID NO 305
<211> LENGTH: 69
<212> TYPE: RNA
<213> ORGANISM: Homo sapiens

<400> SEQUENCE: 305
gggauacuca aaauggggggc gcuuuccuuu uugucuguac ugggaagugc uucgauuuug    60
ggguguccc    69

<210> SEQ ID NO 306
<211> LENGTH: 72
<212> TYPE: RNA
<213> ORGANISM: Homo sapiens

<400> SEQUENCE: 306

```
uacaucggcc auuauaauac aaccugauaa guguuauagc acuuaucaga uuguauugua        60
auugucugug ua                                                           72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucgaug uccaagugga         60 aagugcugcg acauugagc gucaccggug acgcccauau ca                          102

<210> SEQ ID NO 308
<211> LENGTH: 101
<212> TYPE: RNA
<213> ORGANISM: Homo sapiens

<400> SEQUENCE: 308
gcauccccuc agccugugge acucaaacug uggggggcacu uucugcucuc uggugaaagu      60
gccgccaucu uuugaguguu accgcuugag aagacucaac c                          101

<210> SEQ ID NO 309
<211> LENGTH: 102
<212> TYPE: RNA
<213> ORGANISM: Homo sapiens

<400> SEQUENCE: 309
cgaggagcuc auacugggau acucaaaaug ggggcgcuuu ccuuuuuguc uguuacuggg       60
aagugcuucg auuuugggu gucccuguuu gaguagggca uc                          102

<210> SEQ ID NO 310
<211> LENGTH: 22
<212> TYPE: RNA
<213> ORGANISM: Homo sapiens

<400> SEQUENCE: 310
ugagguagua gguuguauag uu                                                22

<210> SEQ ID NO 311
<211> LENGTH: 22
<212> TYPE: RNA
<213> ORGANISM: Homo sapiens

<400> SEQUENCE: 311
ugagguagua gguugugugg uu                                                22

<210> SEQ ID NO 312
<211> LENGTH: 22
<212> TYPE: RNA
<213> ORGANISM: Homo sapiens

<400> SEQUENCE: 312
ugagguagua gguuguaugg uu                                                22

<210> SEQ ID NO 313
<211> LENGTH: 21
<212> TYPE: RNA
<213> ORGANISM: Homo sapiens

<400> SEQUENCE: 313
agagguagua gguugcauag u                                                 21
```

<210> SEQ ID NO 314
<211> LENGTH: 21
<212> TYPE: RNA
<213> ORGANISM: Homo sapiens

<400> SEQUENCE: 314
ugagguagga gguuguauag u                                              21

<210> SEQ ID NO 315
<211> LENGTH: 22
<212> TYPE: RNA
<213> ORGANISM: Homo sapiens

<400> SEQUENCE: 315
ugagguagua gauuguauag uu                                             22

<210> SEQ ID NO 316
<211> LENGTH: 21
<212> TYPE: RNA
<213> ORGANISM: Homo sapiens

<400> SEQUENCE: 316
ugagguagua guuuguacag u                                              21

<210> SEQ ID NO 317
<211> LENGTH: 19
<212> TYPE: RNA
<213> ORGANISM: Homo sapiens

<400> SEQUENCE: 317
ugagguagua guuugugcu                                                 19

<210> SEQ ID NO 318
<211> LENGTH: 21
<212> TYPE: RNA
<213> ORGANISM: Homo sapiens

<400> SEQUENCE: 318
uggaauguaa agaaguaugu a                                              21

<210> SEQ ID NO 319
<211> LENGTH: 21
<212> TYPE: RNA
<213> ORGANISM: Homo sapiens

<400> SEQUENCE: 319
uggaagacua gugauuuugu u                                              21

<210> SEQ ID NO 320
<211> LENGTH: 23
<212> TYPE: RNA
<213> ORGANISM: Homo sapiens

<400> SEQUENCE: 320
ucuuugguua ucuagcugua uga                                            23

<210> SEQ ID NO 321
<211> LENGTH: 21
<212> TYPE: RNA
<213> ORGANISM: Homo sapiens

<400> SEQUENCE: 321
uaaagcuaga uaaccgaaag u                                              21

-continued

```
<210> SEQ ID NO 322
<211> LENGTH: 23
<212> TYPE: RNA
<213> ORGANISM: Homo sapiens

<400> SEQUENCE: 322
uacccuguag auccgaauuu gug                                          23

<210> SEQ ID NO 323
<211> LENGTH: 22
<212> TYPE: RNA
<213> ORGANISM: Homo sapiens

<400> SEQUENCE: 323
uacccuguag aaccgaauuu gu                                           22

<210> SEQ ID NO 324
<211> LENGTH: 22
<212> TYPE: RNA
<213> ORGANISM: Homo sapiens

<400> SEQUENCE: 324
uagcagcaca uaaugguuug ug                                           22

<210> SEQ ID NO 325
<211> LENGTH: 22
<212> TYPE: RNA
<213> ORGANISM: Homo sapiens

<400> SEQUENCE: 325
uagcagcaca ucaugguuua ca                                           22

<210> SEQ ID NO 326
<211> LENGTH: 22
<212> TYPE: RNA
<213> ORGANISM: Homo sapiens

<400> SEQUENCE: 326
uagcagcacg uaaauauugg cg                                           22

<210> SEQ ID NO 327
<211> LENGTH: 24
<212> TYPE: RNA
<213> ORGANISM: Homo sapiens

<400> SEQUENCE: 327
caaagugcuu acagugcagg uagu                                         24

<210> SEQ ID NO 328
<211> LENGTH: 20
<212> TYPE: RNA
<213> ORGANISM: Homo sapiens

<400> SEQUENCE: 328
acugcaguga aggcacuugu                                              20

<210> SEQ ID NO 329
<211> LENGTH: 22
<212> TYPE: RNA
<213> ORGANISM: Homo sapiens

<400> SEQUENCE: 329
uaaggugcau cuagugcaga ua                                           22
```

-continued

<210> SEQ ID NO 330
<211> LENGTH: 23
<212> TYPE: RNA
<213> ORGANISM: Homo sapiens

<400> SEQUENCE: 330
ugugcaaauc uaugcaaaac uga                                    23

<210> SEQ ID NO 331
<211> LENGTH: 23
<212> TYPE: RNA
<213> ORGANISM: Homo sapiens

<400> SEQUENCE: 331
ugugcaaauc caugcaaaac uga                                    23

<210> SEQ ID NO 332
<211> LENGTH: 22
<212> TYPE: RNA
<213> ORGANISM: Homo sapiens

<400> SEQUENCE: 332
uaaagugcuu auagugcagg ua                                     22

<210> SEQ ID NO 333
<211> LENGTH: 22
<212> TYPE: RNA
<213> ORGANISM: Homo sapiens

<400> SEQUENCE: 333
uagcuuauca gacugauguu ga                                     22

<210> SEQ ID NO 334
<211> LENGTH: 22
<212> TYPE: RNA
<213> ORGANISM: Homo sapiens

<400> SEQUENCE: 334
aagcugccag uugaagaacu gu                                     22

<210> SEQ ID NO 335
<211> LENGTH: 21
<212> TYPE: RNA
<213> ORGANISM: Homo sapiens

<400> SEQUENCE: 335
aucacauugc cagggauuuc c                                      21

<210> SEQ ID NO 336
<211> LENGTH: 23
<212> TYPE: RNA
<213> ORGANISM: Homo sapiens

<400> SEQUENCE: 336
aucacauugc cagggauuac cac                                    23

<210> SEQ ID NO 337
<211> LENGTH: 22
<212> TYPE: RNA
<213> ORGANISM: Homo sapiens

<400> SEQUENCE: 337
uggcucaguu cagcaggaac ag                                     22

```
<210> SEQ ID NO 338
<211> LENGTH: 22
<212> TYPE: RNA
<213> ORGANISM: Homo sapiens

<400> SEQUENCE: 338
cauugcacuu gucucggucu ga                                          22

<210> SEQ ID NO 339
<211> LENGTH: 22
<212> TYPE: RNA
<213> ORGANISM: Homo sapiens

<400> SEQUENCE: 339
uucaaguaau ccaggauagg cu                                          22

<210> SEQ ID NO 340
<211> LENGTH: 21
<212> TYPE: RNA
<213> ORGANISM: Homo sapiens

<400> SEQUENCE: 340
uucaaguaau ucaggauagg u                                           21

<210> SEQ ID NO 341
<211> LENGTH: 22
<212> TYPE: RNA
<213> ORGANISM: Homo sapiens

<400> SEQUENCE: 341
uucacagugg cuaaguuccg cc                                          22

<210> SEQ ID NO 342
<211> LENGTH: 20
<212> TYPE: RNA
<213> ORGANISM: Homo sapiens

<400> SEQUENCE: 342
uucacagugg cuaaguucug                                             20

<210> SEQ ID NO 343
<211> LENGTH: 22
<212> TYPE: RNA
<213> ORGANISM: Homo sapiens

<400> SEQUENCE: 343
aaggagcuca cagucuauug ag                                          22

<210> SEQ ID NO 344
<211> LENGTH: 22
<212> TYPE: RNA
<213> ORGANISM: Homo sapiens

<400> SEQUENCE: 344
cuagcaccau cugaaaucgg uu                                          22

<210> SEQ ID NO 345
<211> LENGTH: 20
<212> TYPE: RNA
<213> ORGANISM: Homo sapiens

<400> SEQUENCE: 345
uagcaccauu ugaaaucagu                                             20
```

```
<210> SEQ ID NO 346
<211> LENGTH: 22
<212> TYPE: RNA
<213> ORGANISM: Homo sapiens

<400> SEQUENCE: 346
uagcaccauu ugaaaucggu ua                                              22

<210> SEQ ID NO 347
<211> LENGTH: 23
<212> TYPE: RNA
<213> ORGANISM: Homo sapiens

<400> SEQUENCE: 347
uguaaacauc cucgacugga agc                                             23

<210> SEQ ID NO 348
<211> LENGTH: 22
<212> TYPE: RNA
<213> ORGANISM: Homo sapiens

<400> SEQUENCE: 348
cuuucagucg gauguuugca gc                                              22

<210> SEQ ID NO 349
<211> LENGTH: 21
<212> TYPE: RNA
<213> ORGANISM: Homo sapiens

<400> SEQUENCE: 349
uguaaacauc cuacacucag c                                               21

<210> SEQ ID NO 350
<211> LENGTH: 23
<212> TYPE: RNA
<213> ORGANISM: Homo sapiens

<400> SEQUENCE: 350
uguaaacauc cuacacucuc agc                                             23

<210> SEQ ID NO 351
<211> LENGTH: 22
<212> TYPE: RNA
<213> ORGANISM: Homo sapiens

<400> SEQUENCE: 351
uguaaacauc cccgacugga ag                                              22

<210> SEQ ID NO 352
<211> LENGTH: 20
<212> TYPE: RNA
<213> ORGANISM: Homo sapiens

<400> SEQUENCE: 352
uguaaacauc cuugacugga                                                 20

<210> SEQ ID NO 353
<211> LENGTH: 21
<212> TYPE: RNA
<213> ORGANISM: Homo sapiens

<400> SEQUENCE: 353
ggcaagaugc uggcauagcu g                                               21
```

<210> SEQ ID NO 354
<211> LENGTH: 21
<212> TYPE: RNA
<213> ORGANISM: Homo sapiens

<400> SEQUENCE: 354
uauugcacau uacuaaguug c                                     21

<210> SEQ ID NO 355
<211> LENGTH: 19
<212> TYPE: RNA
<213> ORGANISM: Homo sapiens

<400> SEQUENCE: 355
gugcauugua guugcauug                                        19

<210> SEQ ID NO 356
<211> LENGTH: 22
<212> TYPE: RNA
<213> ORGANISM: Homo sapiens

<400> SEQUENCE: 356
uggcaguguc uuagcugguu gu                                    22

<210> SEQ ID NO 357
<211> LENGTH: 22
<212> TYPE: RNA
<213> ORGANISM: Homo sapiens

<400> SEQUENCE: 357
aggcaguguc auuagcugau ug                                    22

<210> SEQ ID NO 358
<211> LENGTH: 22
<212> TYPE: RNA
<213> ORGANISM: Homo sapiens

<400> SEQUENCE: 358
aggcagugua guuagcugau ug                                    22

<210> SEQ ID NO 359
<211> LENGTH: 22
<212> TYPE: RNA
<213> ORGANISM: Homo sapiens

<400> SEQUENCE: 359
uauugcacuu gucccggccu gu                                    22

<210> SEQ ID NO 360
<211> LENGTH: 22
<212> TYPE: RNA
<213> ORGANISM: Homo sapiens

<400> SEQUENCE: 360
aaagugcugu ucgugcaggu ag                                    22

<210> SEQ ID NO 361
<211> LENGTH: 22
<212> TYPE: RNA
<213> ORGANISM: Homo sapiens

<400> SEQUENCE: 361
uucaacgggu auuuauugag ca                                    22

-continued

<210> SEQ ID NO 362
<211> LENGTH: 22
<212> TYPE: RNA
<213> ORGANISM: Homo sapiens

<400> SEQUENCE: 362
uuuggcacua gcacauuuuu gc                                               22

<210> SEQ ID NO 363
<211> LENGTH: 22
<212> TYPE: RNA
<213> ORGANISM: Homo sapiens

<400> SEQUENCE: 363
ugagguagua aguuguauug uu                                               22

<210> SEQ ID NO 364
<211> LENGTH: 22
<212> TYPE: RNA
<213> ORGANISM: Homo sapiens

<400> SEQUENCE: 364
aacccguaga uccgaucuug ug                                               22

<210> SEQ ID NO 365
<211> LENGTH: 22
<212> TYPE: RNA
<213> ORGANISM: Homo sapiens

<400> SEQUENCE: 365
cacccguaga accgaccuug cg                                               22

<210> SEQ ID NO 366
<211> LENGTH: 22
<212> TYPE: RNA
<213> ORGANISM: Homo sapiens

<400> SEQUENCE: 366
uacaguacug ugauaacuga ag                                               22

<210> SEQ ID NO 367
<211> LENGTH: 22
<212> TYPE: RNA
<213> ORGANISM: Homo sapiens

<400> SEQUENCE: 367
uacaguacug ugauaacuga ag                                               22

<210> SEQ ID NO 368
<211> LENGTH: 23
<212> TYPE: RNA
<213> ORGANISM: Homo sapiens

<400> SEQUENCE: 368
agcagcauug uacagggcua uga                                              23

<210> SEQ ID NO 369
<211> LENGTH: 20
<212> TYPE: RNA
<213> ORGANISM: Homo sapiens

<400> SEQUENCE: 369
ucaaaugcuc agacuccugu                                                  20

```
<210> SEQ ID NO 370
<211> LENGTH: 24
<212> TYPE: RNA
<213> ORGANISM: Homo sapiens

<400> SEQUENCE: 370
aaaagugcuu acagugcagg uagc                                              24

<210> SEQ ID NO 371
<211> LENGTH: 21
<212> TYPE: RNA
<213> ORGANISM: Homo sapiens

<400> SEQUENCE: 371
uaaagugcug acagugcaga u                                                 21

<210> SEQ ID NO 372
<211> LENGTH: 23
<212> TYPE: RNA
<213> ORGANISM: Homo sapiens

<400> SEQUENCE: 372
agcagcauug uacagggcua uca                                               23

<210> SEQ ID NO 373
<211> LENGTH: 23
<212> TYPE: RNA
<213> ORGANISM: Homo sapiens

<400> SEQUENCE: 373
uggaguguga caaugguguu ugu                                               23

<210> SEQ ID NO 374
<211> LENGTH: 22
<212> TYPE: RNA
<213> ORGANISM: Homo sapiens

<400> SEQUENCE: 374
uuaaggcacg cggugaaugc ca                                                22

<210> SEQ ID NO 375
<211> LENGTH: 23
<212> TYPE: RNA
<213> ORGANISM: Homo sapiens

<400> SEQUENCE: 375
ucccugagac ccuuuaaccu gug                                               23

<210> SEQ ID NO 376
<211> LENGTH: 22
<212> TYPE: RNA
<213> ORGANISM: Homo sapiens

<400> SEQUENCE: 376
ucccugagac ccuaacuugu ga                                                22

<210> SEQ ID NO 377
<211> LENGTH: 21
<212> TYPE: RNA
<213> ORGANISM: Homo sapiens

<400> SEQUENCE: 377
cauuauuacu uuugguacgc g                                                 21
```

<210> SEQ ID NO 378
<211> LENGTH: 21
<212> TYPE: RNA
<213> ORGANISM: Homo sapiens

<400> SEQUENCE: 378
ucguaccgug aguaauaaug c                                          21

<210> SEQ ID NO 379
<211> LENGTH: 22
<212> TYPE: RNA
<213> ORGANISM: Homo sapiens

<400> SEQUENCE: 379
ucggauccgu cugagcuugg cu                                         22

<210> SEQ ID NO 380
<211> LENGTH: 22
<212> TYPE: RNA
<213> ORGANISM: Homo sapiens

<400> SEQUENCE: 380
ucacagugaa ccggucucuu uu                                         22

<210> SEQ ID NO 381
<211> LENGTH: 22
<212> TYPE: RNA
<213> ORGANISM: Homo sapiens

<400> SEQUENCE: 381
ucacagugaa ccggucucuu uc                                         22

<210> SEQ ID NO 382
<211> LENGTH: 21
<212> TYPE: RNA
<213> ORGANISM: Homo sapiens

<400> SEQUENCE: 382
cuuuuugcgg ucugggcuug c                                          21

<210> SEQ ID NO 383
<211> LENGTH: 20
<212> TYPE: RNA
<213> ORGANISM: Homo sapiens

<400> SEQUENCE: 383
cagugcaaug uuaaaagggc                                            20

<210> SEQ ID NO 384
<211> LENGTH: 22
<212> TYPE: RNA
<213> ORGANISM: Homo sapiens

<400> SEQUENCE: 384
cagugcaaug augaaagggc au                                         22

<210> SEQ ID NO 385
<211> LENGTH: 22
<212> TYPE: RNA
<213> ORGANISM: Homo sapiens

<400> SEQUENCE: 385
uaacagucua cagccauggu cg                                         22

```
<210> SEQ ID NO 386
<211> LENGTH: 22
<212> TYPE: RNA
<213> ORGANISM: Homo sapiens

<400> SEQUENCE: 386
uugguccccu ucaaccagcu gu                                            22

<210> SEQ ID NO 387
<211> LENGTH: 21
<212> TYPE: RNA
<213> ORGANISM: Homo sapiens

<400> SEQUENCE: 387
uugguccccu ucaaccagcu a                                             21

<210> SEQ ID NO 388
<211> LENGTH: 21
<212> TYPE: RNA
<213> ORGANISM: Homo sapiens

<400> SEQUENCE: 388
ugugacuggu ugaccagagg g                                             21

<210> SEQ ID NO 389
<211> LENGTH: 23
<212> TYPE: RNA
<213> ORGANISM: Homo sapiens

<400> SEQUENCE: 389
uauggcuuuu uauuccuaug uga                                           23

<210> SEQ ID NO 390
<211> LENGTH: 22
<212> TYPE: RNA
<213> ORGANISM: Homo sapiens

<400> SEQUENCE: 390
uauggcuuuu cauuccuaug ug                                            22

<210> SEQ ID NO 391
<211> LENGTH: 23
<212> TYPE: RNA
<213> ORGANISM: Homo sapiens

<400> SEQUENCE: 391
acuccauuug uuuugaugau gga                                           23

<210> SEQ ID NO 392
<211> LENGTH: 22
<212> TYPE: RNA
<213> ORGANISM: Homo sapiens

<400> SEQUENCE: 392
uauugcuuaa gaauacgcgu ag                                            22

<210> SEQ ID NO 393
<211> LENGTH: 17
<212> TYPE: RNA
<213> ORGANISM: Homo sapiens

<400> SEQUENCE: 393
agcugguguu gugaauc                                                  17
```

```
<210> SEQ ID NO 394
<211> LENGTH: 18
<212> TYPE: RNA
<213> ORGANISM: Homo sapiens

<400> SEQUENCE: 394
ucuacagugc acgugucu                                                   18

<210> SEQ ID NO 395
<211> LENGTH: 21
<212> TYPE: RNA
<213> ORGANISM: Homo sapiens

<400> SEQUENCE: 395
agugguuuua cccuauggua g                                               21

<210> SEQ ID NO 396
<211> LENGTH: 21
<212> TYPE: RNA
<213> ORGANISM: Homo sapiens

<400> SEQUENCE: 396
aacacugucu gguaaagaug g                                               21

<210> SEQ ID NO 397
<211> LENGTH: 23
<212> TYPE: RNA
<213> ORGANISM: Homo sapiens

<400> SEQUENCE: 397
uguaguguuu ccuacuuuau gga                                             23

<210> SEQ ID NO 398
<211> LENGTH: 20
<212> TYPE: RNA
<213> ORGANISM: Homo sapiens

<400> SEQUENCE: 398
cauaaaguag aaagcacuac                                                 20

<210> SEQ ID NO 399
<211> LENGTH: 22
<212> TYPE: RNA
<213> ORGANISM: Homo sapiens

<400> SEQUENCE: 399
ugagaugaag cacuguagcu ca                                              22

<210> SEQ ID NO 400
<211> LENGTH: 22
<212> TYPE: RNA
<213> ORGANISM: Homo sapiens

<400> SEQUENCE: 400
uacaguauag augauguacu ag                                              22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu                                            24
```

-continued

```
<210> SEQ ID NO 402
<211> LENGTH: 22
<212> TYPE: RNA
<213> ORGANISM: Homo sapiens

<400> SEQUENCE: 402
ugagaacuga auccaugggu uu                                              22

<210> SEQ ID NO 403
<211> LENGTH: 20
<212> TYPE: RNA
<213> ORGANISM: Homo sapiens

<400> SEQUENCE: 403
guguguggaa augcuucugc                                                 20

<210> SEQ ID NO 404
<211> LENGTH: 22
<212> TYPE: RNA
<213> ORGANISM: Homo sapiens

<400> SEQUENCE: 404
ucagugcacu acagaacuuu gu                                              22

<210> SEQ ID NO 405
<211> LENGTH: 22
<212> TYPE: RNA
<213> ORGANISM: Homo sapiens

<400> SEQUENCE: 405
ucagugcauc acagaacuuu gu                                              22

<210> SEQ ID NO 406
<211> LENGTH: 22
<212> TYPE: RNA
<213> ORGANISM: Homo sapiens

<400> SEQUENCE: 406
ucuggcuccg ugucuucacu cc                                              22

<210> SEQ ID NO 407
<211> LENGTH: 22
<212> TYPE: RNA
<213> ORGANISM: Homo sapiens

<400> SEQUENCE: 407
ucucccaacc cuuguaccag ug                                              22

<210> SEQ ID NO 408
<211> LENGTH: 22
<212> TYPE: RNA
<213> ORGANISM: Homo sapiens

<400> SEQUENCE: 408
acuagacuga agcuccuuga gg                                              22

<210> SEQ ID NO 409
<211> LENGTH: 21
<212> TYPE: RNA
<213> ORGANISM: Homo sapiens

<400> SEQUENCE: 409
ucagugcaug acagaacuug g                                               21
```

```
<210> SEQ ID NO 410
<211> LENGTH: 20
<212> TYPE: RNA
<213> ORGANISM: Homo sapiens

<400> SEQUENCE: 410
uugcauaguc acaaaaguga                                                   20

<210> SEQ ID NO 411
<211> LENGTH: 22
<212> TYPE: RNA
<213> ORGANISM: Homo sapiens

<400> SEQUENCE: 411
uagguuaucc guguugccuu cg                                                22

<210> SEQ ID NO 412
<211> LENGTH: 22
<212> TYPE: RNA
<213> ORGANISM: Homo sapiens

<400> SEQUENCE: 412
aaucauacac gguugaccua uu                                                22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg                                                22

<210> SEQ ID NO 414
<211> LENGTH: 23
<212> TYPE: RNA
<213> ORGANISM: Homo sapiens

<400> SEQUENCE: 414
aacauucaac gcugucggug agu                                               23

<210> SEQ ID NO 415
<211> LENGTH: 24
<212> TYPE: RNA
<213> ORGANISM: Homo sapiens

<400> SEQUENCE: 415
aacauucauu gcugucggug gguu                                              24

<210> SEQ ID NO 416
<211> LENGTH: 22
<212> TYPE: RNA
<213> ORGANISM: Homo sapiens

<400> SEQUENCE: 416
aacauucaac cugucgguga gu                                                22

<210> SEQ ID NO 417
<211> LENGTH: 22
<212> TYPE: RNA
<213> ORGANISM: Homo sapiens

<400> SEQUENCE: 417
uuuggcaaug guagaacuca ca                                                22
```

<210> SEQ ID NO 418
<211> LENGTH: 21
<212> TYPE: RNA
<213> ORGANISM: Homo sapiens

<400> SEQUENCE: 418
ugguucuaga cuugccaacu a    21

<210> SEQ ID NO 419
<211> LENGTH: 23
<212> TYPE: RNA
<213> ORGANISM: Homo sapiens

<400> SEQUENCE: 419
uauggcacug guagaauuca cug    23

<210> SEQ ID NO 420
<211> LENGTH: 22
<212> TYPE: RNA
<213> ORGANISM: Homo sapiens

<400> SEQUENCE: 420
uggacggaga acugauaagg gu    22

<210> SEQ ID NO 421
<211> LENGTH: 18
<212> TYPE: RNA
<213> ORGANISM: Homo sapiens

<400> SEQUENCE: 421
uggagagaaa ggcaguuc    18

<210> SEQ ID NO 422
<211> LENGTH: 23
<212> TYPE: RNA
<213> ORGANISM: Homo sapiens

<400> SEQUENCE: 422
caaagaauuc uccuuuuggg cuu    23

<210> SEQ ID NO 423
<211> LENGTH: 21
<212> TYPE: RNA
<213> ORGANISM: Homo sapiens

<400> SEQUENCE: 423
ucgugucuug uguugcagcc g    21

<210> SEQ ID NO 424
<211> LENGTH: 22
<212> TYPE: RNA
<213> ORGANISM: Homo sapiens

<400> SEQUENCE: 424
caucccuugc augguggagg gu    22

<210> SEQ ID NO 425
<211> LENGTH: 23
<212> TYPE: RNA
<213> ORGANISM: Homo sapiens

<400> SEQUENCE: 425
gugccuacug agcugauauc agu    23

<210> SEQ ID NO 426
<211> LENGTH: 22
<212> TYPE: RNA
<213> ORGANISM: Homo sapiens

<400> SEQUENCE: 426
ugauauguuu gauauauuag gu                                              22

<210> SEQ ID NO 427
<211> LENGTH: 22
<212> TYPE: RNA
<213> ORGANISM: Homo sapiens

<400> SEQUENCE: 427
caacggaauc ccaaaagcag cu                                              22

<210> SEQ ID NO 428
<211> LENGTH: 21
<212> TYPE: RNA
<213> ORGANISM: Homo sapiens

<400> SEQUENCE: 428
cugaccuaug aauugacagc c                                               21

<210> SEQ ID NO 429
<211> LENGTH: 21
<212> TYPE: RNA
<213> ORGANISM: Homo sapiens

<400> SEQUENCE: 429
aacuggccua caaaguccca g                                               21

<210> SEQ ID NO 430
<211> LENGTH: 22
<212> TYPE: RNA
<213> ORGANISM: Homo sapiens

<400> SEQUENCE: 430
uguaacagca acuccaugug ga                                              22

<210> SEQ ID NO 431
<211> LENGTH: 21
<212> TYPE: RNA
<213> ORGANISM: Homo sapiens

<400> SEQUENCE: 431
uagcagcaca gaaauauugg c                                               21

<210> SEQ ID NO 432
<211> LENGTH: 21
<212> TYPE: RNA
<213> ORGANISM: Homo sapiens

<400> SEQUENCE: 432
uagguaguuu cauguuguug g                                               21

<210> SEQ ID NO 433
<211> LENGTH: 21
<212> TYPE: RNA
<213> ORGANISM: Homo sapiens

<400> SEQUENCE: 433
uagguaguuu ccuguuguug g                                               21

<210> SEQ ID NO 434
<211> LENGTH: 22
<212> TYPE: RNA
<213> ORGANISM: Homo sapiens

<400> SEQUENCE: 434
uucaccaccu ucuccaccca gc                                              22

<210> SEQ ID NO 435
<211> LENGTH: 19
<212> TYPE: RNA
<213> ORGANISM: Homo sapiens

<400> SEQUENCE: 435
gguccagagg ggagauagg                                                  19

<210> SEQ ID NO 436
<211> LENGTH: 23
<212> TYPE: RNA
<213> ORGANISM: Homo sapiens

<400> SEQUENCE: 436
cccaguguuc agacuaccug uuc                                             23

<210> SEQ ID NO 437
<211> LENGTH: 22
<212> TYPE: RNA
<213> ORGANISM: Homo sapiens

<400> SEQUENCE: 437
uacaguaguc ugcacauugg uu                                              22

<210> SEQ ID NO 438
<211> LENGTH: 23
<212> TYPE: RNA
<213> ORGANISM: Homo sapiens

<400> SEQUENCE: 438
cccaguguuu agacuaucug uuc                                             23

<210> SEQ ID NO 439
<211> LENGTH: 22
<212> TYPE: RNA
<213> ORGANISM: Homo sapiens

<400> SEQUENCE: 439
uaacacuguc ugguaacgau gu                                              22

<210> SEQ ID NO 440
<211> LENGTH: 24
<212> TYPE: RNA
<213> ORGANISM: Homo sapiens

<400> SEQUENCE: 440
cucuaauacu gccugguaau gaug                                            24

<210> SEQ ID NO 441
<211> LENGTH: 22
<212> TYPE: RNA
<213> ORGANISM: Homo sapiens

<400> SEQUENCE: 441
aauacugccg gguaaugaug ga                                              22

```
<210> SEQ ID NO 442
<211> LENGTH: 22
<212> TYPE: RNA
<213> ORGANISM: Homo sapiens

<400> SEQUENCE: 442
agagguauag ggcaugggaa ga                                              22

<210> SEQ ID NO 443
<211> LENGTH: 22
<212> TYPE: RNA
<213> ORGANISM: Homo sapiens

<400> SEQUENCE: 443
gugaaauguu uaggaccacu ag                                              22

<210> SEQ ID NO 444
<211> LENGTH: 22
<212> TYPE: RNA
<213> ORGANISM: Homo sapiens

<400> SEQUENCE: 444
uucccuuugu cauccuaugc cu                                              22

<210> SEQ ID NO 445
<211> LENGTH: 22
<212> TYPE: RNA
<213> ORGANISM: Homo sapiens

<400> SEQUENCE: 445
uccuucauuc caccggaguc ug                                              22

<210> SEQ ID NO 446
<211> LENGTH: 22
<212> TYPE: RNA
<213> ORGANISM: Homo sapiens

<400> SEQUENCE: 446
uggaauguaa ggaagugugu gg                                              22

<210> SEQ ID NO 447
<211> LENGTH: 22
<212> TYPE: RNA
<213> ORGANISM: Homo sapiens

<400> SEQUENCE: 447
auaagacgag caaaaagcuu gu                                              22

<210> SEQ ID NO 448
<211> LENGTH: 21
<212> TYPE: RNA
<213> ORGANISM: Homo sapiens

<400> SEQUENCE: 448
cugugcgugu gacagcggcu g                                               21

<210> SEQ ID NO 449
<211> LENGTH: 22
<212> TYPE: RNA
<213> ORGANISM: Homo sapiens

<400> SEQUENCE: 449
uucccuuugu cauccuucgc cu                                              22
```

<210> SEQ ID NO 450
<211> LENGTH: 21
<212> TYPE: RNA
<213> ORGANISM: Homo sapiens

<400> SEQUENCE: 450
uaacagucuc cagucacggc c                                                21

<210> SEQ ID NO 451
<211> LENGTH: 22
<212> TYPE: RNA
<213> ORGANISM: Homo sapiens

<400> SEQUENCE: 451
accaucgacc guugauugua cc                                               22

<210> SEQ ID NO 452
<211> LENGTH: 21
<212> TYPE: RNA
<213> ORGANISM: Homo sapiens

<400> SEQUENCE: 452
acagcaggca cagacaggca g                                                21

<210> SEQ ID NO 453
<211> LENGTH: 21
<212> TYPE: RNA
<213> ORGANISM: Homo sapiens

<400> SEQUENCE: 453
augaccuaug aauugacaga c                                                21

<210> SEQ ID NO 454
<211> LENGTH: 21
<212> TYPE: RNA
<213> ORGANISM: Homo sapiens

<400> SEQUENCE: 454
uaaucucagc uggcaacugu g                                                21

<210> SEQ ID NO 455
<211> LENGTH: 24
<212> TYPE: RNA
<213> ORGANISM: Homo sapiens

<400> SEQUENCE: 455
uacugcauca ggaacugauu ggau                                             24

<210> SEQ ID NO 456
<211> LENGTH: 21
<212> TYPE: RNA
<213> ORGANISM: Homo sapiens

<400> SEQUENCE: 456
uugugcuuga ucuaaccaug u                                                21

<210> SEQ ID NO 457
<211> LENGTH: 21
<212> TYPE: RNA
<213> ORGANISM: Homo sapiens

<400> SEQUENCE: 457
ugauugucca aacgcaauuc u                                                21

<210> SEQ ID NO 458
<211> LENGTH: 21
<212> TYPE: RNA
<213> ORGANISM: Homo sapiens

<400> SEQUENCE: 458
ccacaccgua ucugacacuu u                                        21

<210> SEQ ID NO 459
<211> LENGTH: 23
<212> TYPE: RNA
<213> ORGANISM: Homo sapiens

<400> SEQUENCE: 459
agcuacauug ucugcugggu uuc                                      23

<210> SEQ ID NO 460
<211> LENGTH: 24
<212> TYPE: RNA
<213> ORGANISM: Homo sapiens

<400> SEQUENCE: 460
agcuacaucu ggcuacuggg ucuc                                     24

<210> SEQ ID NO 461
<211> LENGTH: 21
<212> TYPE: RNA
<213> ORGANISM: Homo sapiens

<400> SEQUENCE: 461
ugucaguuug ucaaauaccc c                                        21

<210> SEQ ID NO 462
<211> LENGTH: 23
<212> TYPE: RNA
<213> ORGANISM: Homo sapiens

<400> SEQUENCE: 462
caagucacua gugguuccgu uua                                      23

<210> SEQ ID NO 463
<211> LENGTH: 21
<212> TYPE: RNA
<213> ORGANISM: Homo sapiens

<400> SEQUENCE: 463 agggccccccc cucaauccug u                                       21

<210> SEQ ID NO 464
<211> LENGTH: 22
<212> TYPE: RNA
<213> ORGANISM: Homo sapiens

<400> SEQUENCE: 464
ugguuuaccg ucccacauac au                                       22

<210> SEQ ID NO 465
<211> LENGTH: 23
<212> TYPE: RNA
<213> ORGANISM: Homo sapiens

<400> SEQUENCE: 465
cagugcaaua guauugucaa agc                                      23

```
<210> SEQ ID NO 466
<211> LENGTH: 23
<212> TYPE: RNA
<213> ORGANISM: Homo sapiens

<400> SEQUENCE: 466
uaagugcuuc cauguuuugg uga                                              23

<210> SEQ ID NO 467
<211> LENGTH: 23
<212> TYPE: RNA
<213> ORGANISM: Homo sapiens

<400> SEQUENCE: 467
acuuuaacau ggaagugcuu ucu                                              23

<210> SEQ ID NO 468
<211> LENGTH: 23
<212> TYPE: RNA
<213> ORGANISM: Homo sapiens

<400> SEQUENCE: 468
uaagugcuuc cauguuuuag uag                                              23

<210> SEQ ID NO 469
<211> LENGTH: 22
<212> TYPE: RNA
<213> ORGANISM: Homo sapiens

<400> SEQUENCE: 469
uuuaacaugg ggguaccugc ug                                               22

<210> SEQ ID NO 470
<211> LENGTH: 23
<212> TYPE: RNA
<213> ORGANISM: Homo sapiens

<400> SEQUENCE: 470
uaagugcuuc cauguuucag ugg                                              23

<210> SEQ ID NO 471
<211> LENGTH: 23
<212> TYPE: RNA
<213> ORGANISM: Homo sapiens

<400> SEQUENCE: 471
uaagugcuuc cauguuugag ugu                                              23

<210> SEQ ID NO 472
<211> LENGTH: 23
<212> TYPE: RNA
<213> ORGANISM: Homo sapiens

<400> SEQUENCE: 472
aaaagcuggg uugagagggc gaa                                              23

<210> SEQ ID NO 473
<211> LENGTH: 21
<212> TYPE: RNA
<213> ORGANISM: Homo sapiens

<400> SEQUENCE: 473
uaagccaggg auuguggguu c                                                21
```

<210> SEQ ID NO 474
<211> LENGTH: 22
<212> TYPE: RNA
<213> ORGANISM: Homo sapiens

<400> SEQUENCE: 474
gcacauuaca cggucgaccu cu                                       22

<210> SEQ ID NO 475
<211> LENGTH: 23
<212> TYPE: RNA
<213> ORGANISM: Homo sapiens

<400> SEQUENCE: 475
cgcauccccu agggcauugg ugu                                      23

<210> SEQ ID NO 476
<211> LENGTH: 22
<212> TYPE: RNA
<213> ORGANISM: Homo sapiens

<400> SEQUENCE: 476
ccacugcccc aggugcugcu gg                                       22

<210> SEQ ID NO 477
<211> LENGTH: 21
<212> TYPE: RNA
<213> ORGANISM: Homo sapiens

<400> SEQUENCE: 477
ccuaguaggu guccaguaag u                                        21

<210> SEQ ID NO 478
<211> LENGTH: 20
<212> TYPE: RNA
<213> ORGANISM: Homo sapiens

<400> SEQUENCE: 478
ccucugggcc cuuccuccag                                          20

<210> SEQ ID NO 479
<211> LENGTH: 22
<212> TYPE: RNA
<213> ORGANISM: Homo sapiens

<400> SEQUENCE: 479
cuggcccucu cugcccuucc gu                                       22

<210> SEQ ID NO 480
<211> LENGTH: 23
<212> TYPE: RNA
<213> ORGANISM: Homo sapiens

<400> SEQUENCE: 480
gcaaagcaca cggccugcag aga                                      23

<210> SEQ ID NO 481
<211> LENGTH: 21
<212> TYPE: RNA
<213> ORGANISM: Homo sapiens

<400> SEQUENCE: 481
gccccugggc cuauccuaga a                                        21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu                                           23

<210> SEQ ID NO 483
<211> LENGTH: 23
<212> TYPE: RNA
<213> ORGANISM: Homo sapiens

<400> SEQUENCE: 483
uccagcuccu auaugaugcc uuu                                           23

<210> SEQ ID NO 484
<211> LENGTH: 23
<212> TYPE: RNA
<213> ORGANISM: Homo sapiens

<400> SEQUENCE: 484
uccagcauca gugauuuugu uga                                           23

<210> SEQ ID NO 485
<211> LENGTH: 21
<212> TYPE: RNA
<213> ORGANISM: Homo sapiens

<400> SEQUENCE: 485
ucccuguccu ccaggagcuc a                                             21

<210> SEQ ID NO 486
<211> LENGTH: 23
<212> TYPE: RNA
<213> ORGANISM: Homo sapiens

<400> SEQUENCE: 486
uccgucucag uuacuuuaua gcc                                           23

<210> SEQ ID NO 487
<211> LENGTH: 24
<212> TYPE: RNA
<213> ORGANISM: Homo sapiens

<400> SEQUENCE: 487
ucucacacag aaaucgcacc cguc                                          24

<210> SEQ ID NO 488
<211> LENGTH: 21
<212> TYPE: RNA
<213> ORGANISM: Homo sapiens

<400> SEQUENCE: 488
ugcugacucc uaguccaggg c                                             21

<210> SEQ ID NO 489
<211> LENGTH: 23
<212> TYPE: RNA
<213> ORGANISM: Homo sapiens

<400> SEQUENCE: 489
ugucugcccg caugccugcc ucu                                           23

```
<210> SEQ ID NO 490
<211> LENGTH: 22
<212> TYPE: RNA
<213> ORGANISM: Homo sapiens

<400> SEQUENCE: 490
aauugcacuu uagcaauggu ga                                              22

<210> SEQ ID NO 491
<211> LENGTH: 22
<212> TYPE: RNA
<213> ORGANISM: Homo sapiens

<400> SEQUENCE: 491
acauagagga aauuccacgu uu                                              22

<210> SEQ ID NO 492
<211> LENGTH: 21
<212> TYPE: RNA
<213> ORGANISM: Homo sapiens

<400> SEQUENCE: 492
aauaauacau gguugaucuu u                                               21

<210> SEQ ID NO 493
<211> LENGTH: 21
<212> TYPE: RNA
<213> ORGANISM: Homo sapiens

<400> SEQUENCE: 493
gccugcuggg guggaaccug g                                               21

<210> SEQ ID NO 494
<211> LENGTH: 21
<212> TYPE: RNA
<213> ORGANISM: Homo sapiens

<400> SEQUENCE: 494
gugccgccau cuuuugagug u                                               21

<210> SEQ ID NO 495
<211> LENGTH: 23
<212> TYPE: RNA
<213> ORGANISM: Homo sapiens

<400> SEQUENCE: 495
aaagugcugc gacauuugag cgu                                             23

<210> SEQ ID NO 496
<211> LENGTH: 22
<212> TYPE: RNA
<213> ORGANISM: Homo sapiens

<400> SEQUENCE: 496
acucaaaaug ggggcgcuuu cc                                              22

<210> SEQ ID NO 497
<211> LENGTH: 23
<212> TYPE: RNA
<213> ORGANISM: Homo sapiens

<400> SEQUENCE: 497
gaagugcuuc gauuuugggg ugu                                             23
```

```
<210> SEQ ID NO 498
<211> LENGTH: 22
<212> TYPE: RNA
<213> ORGANISM: Homo sapiens

<400> SEQUENCE: 498
uuauaauaca accugauaag ug                                            22
```

MICRORNA-BASED METHODS AND COMPOSITIONS FOR THE DIAGNOSIS, PROGNOSIS AND TREATMENT OF SOLID CANCERS

GOVERNMENT SUPPORT

This invention was made with government support under P01CA76259, P01CA81534 and P30CA56036 awarded by The National Institutes of Health. The Government has certain rights in this invention.

BACKGROUND OF THE INVENTION

Cancer, the uncontrolled growth of malignant cells, is a major health problem of the modern medical era and is one of the leading causes of death in developed countries. In the United States, one in four deaths is caused by cancer (Jemal, A. et al., *CA Cancer J. Clin.* 52:23-47 (2002)). Among cancers, those that arise from organs and solid tissues, known as solid cancers (e.g., colon cancer, lung cancer, breast cancer, stomach cancer, prostate cancer, pancreatic cancer) are among the most-commonly identified human cancers.

For example, prostate cancer is the most frequently diagnosed noncutaneous malignancy among men in industrialized countries, and, in the United States, 1 in 8 men will develop prostate cancer during his life (Simard, J. et al., *Endocrinology* 143(6):2029-40 (2002)). The incidence of prostate cancer has dramatically increased over the last decades and prostate cancer is now a leading cause of death in the United States and Western Europe (Peschel, R. E. and J. W. Colberg, *Lancet* 4:233-41 (2003); Nelson, W. G. et al., *N. Engl. J. Med.* 349(4):366-81 (2003)). An average 40% reduction in life expectancy affects males with prostate cancer. If detected early, prior to metastasis and local spread beyond the capsule, prostate cancer can often times be cured (e.g., using surgery). However, if diagnosed after spread and metastasis from the prostate, prostate cancer is typically a fatal disease with low cure rates. While prostate-specific antigen (PSA)-based screening has aided early diagnosis of prostate cancer, it is neither highly sensitive nor specific (Punglia et al., *N. Engl. J. Med.* 349(4):335-42 (2003)). This means that a high percentage of false negative and false positive diagnoses are associated with the test. The consequences are both many instances of missed cancers and unnecessary follow-up biopsies for those without cancer.

Breast cancer remains the second leading cause of cancer-related deaths in women, affecting more than 180,000 women in the United States each year. For women in North America, the life-time odds of getting breast cancer are now one in eight. Although the discovery of BRCA1 and BRCA2 were important steps in identifying key genetic factors involved in breast cancer, it has become clear that mutations in BRCA1 and BRCA2 account for only a fraction of inherited susceptibility to breast cancer (Nathanson, K. L., et al., *Human Mol. Gen.* 10(7):715-720 (2001); Anglican Breast Cancer Study Group. *Br. J. Cancer* 83(10):1301-08 (2000); and Syrjakoski, K., et al., *J. Natl. Cancer Inst.* 92:1529-31 (2000)). Despite considerable research into therapies for breast cancer, breast cancer remains difficult to diagnose and treat effectively, and the high mortality observed in breast cancer patients indicates that improvements are needed in the diagnosis, treatment and prevention of the disease.

Excluding skin cancer, colorectal cancer is the third most frequently diagnosed cancer in the United States and Canada (after lung and breast in women, and lung and prostate in men). The American Cancer Society estimates that there will be approximately 145,000 new cases of colorectal cancer diagnosed in the U.S. in 2005 (Cancer Facts and Figures 2005. Atlanta, Ga.: American Cancer Society, 2005. Available at www.cancer.org/docroot/STT/stt_0.asp, accessed Dec. 19, 2005). Colorectal cancer is the second leading cause of cancer death among men and women in the United States and Canada (after lung cancer).

The annual incidence of pancreatic cancer is nearly equivalent to the annual mortality, estimated to be 31,860 and 31,270, respectively, in the U.S. in 2004 (Cancer Facts and Figures 2004. Atlanta, Ga.: American Cancer Society, 2004. Available at www.cancer.org/docroot/STT/stt_0_2004.asp, accessed Aug. 21, 2005). Patients with locally advanced and metastatic pancreatic cancer have poor prognoses, and diagnosis generally occurs too late for surgery or radiotherapy to be curative (Burr, H. A., et al., *The Oncologist* 10(3): 183-190, (2005)). Chemotherapy can provide relief of symptoms for some patients with advanced pancreatic cancer, but its impact on survival has been modest to date.

In the United States, more than 20,000 individuals are diagnosed with stomach (gastric) cancer each year. The American Cancer Society estimates that there will be 22,710 new cases of colorectal cancer diagnosed in the U.S. in 2004 (Cancer Facts and Figures 2004. Atlanta, Ga.: American Cancer Society, 2004. Available at www.cancer.org/docroot/STT/stt_0_2004.asp, accessed Aug. 21, 2005). Because stomach cancer may occur without symptoms, it may be in advanced stages by the time the diagnosis is made. Treatment is then directed at making the patient more comfortable and improving quality of life.

Lung cancer causes more deaths worldwide than any other form of cancer (Goodman, G. E., *Thorax* 57:994-999 (2002)). In the United States, lung cancer is the primary cause of cancer death among both men and women. In 2002, the death rate from lung cancer was an estimated 134,900 deaths, exceeding the combined total for breast, prostate and colon cancer. Id. Lung cancer is also the leading cause of cancer death in all European countries, and numbers of lung cancer-related deaths are rapidly increasing in developing countries as well.

The five-year survival rate among all lung cancer patients, regardless of the stage of disease at diagnosis, is only about 13%. This contrasts with a five-year survival rate of 46% among cases detected while the disease is still localized. However, only 16% of lung cancers are discovered before the disease has spread. Early detection is difficult as clinical symptoms are often not observed until the disease has reached an advanced stage. Despite research into therapies for this and other cancers, lung cancer remains difficult to diagnose and treat effectively.

Clearly, the identification of markers and genes that are responsible for susceptibility to particular forms of solid cancer (e.g., prostate cancer, breast cancer, lung cancer, stomach cancer, colon cancer, pancreatic cancer) is one of the major challenges facing oncology today. There is a need to identify means for the early detection of individuals that have a genetic susceptibility to cancer so that more aggressive screening and intervention regimens may be instituted for the early detection and treatment of cancer. Cancer genes may also reveal key molecular pathways that may be manipulated (e.g., using small or large molecule weight drugs) and may lead to more effective treatments regardless of the cancer stage when a particular cancer is first diagnosed.

MicroRNAs are a class of small, non-coding RNAs that control gene expression by hybridizing to and triggering either translational repression or, less frequently, degradation of a messenger RNA (mRNA) target. The discovery and study of miRNAs has revealed miRNA-mediated gene regulatory mechanisms that play important roles in organismal development and various cellular processes, such as cell differentiation, cell growth and cell death (Cheng, A. M., et al., *Nucleic Acids Res.* 33:1290-1297 (2005)). Recent studies suggest that aberrant expression of particular miRNAs may be involved in human diseases, such as neurological disorders (Ishizuka, A., et al., *Genes Dev.* 16:2497-2508 (2002)) and cancer. In particular, misexpression of miR-16-1 and/or miR-15a has been found in human chronic lymphocytic leukemias (Calin, G. A., et al., *Proc. Natl. Acad. Sci. U.S.A.* 99:15524-15529 (2002)).

Clearly, there is a great need in the art for improved methods for detecting and treating solid cancers (e.g., prostate cancer, breast cancer, lung cancer, stomach cancer, colon cancer, pancreatic cancer). The present invention provides novel methods and compositions for the diagnosis and treatment of solid cancers.

SUMMARY OF THE INVENTION

The present invention is based, in part, on the identification of specific miRNAs that have altered expression levels in particular solid cancers.

Accordingly, the invention encompasses methods of diagnosing whether a subject has, or is at risk for developing, a solid cancer. According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, a solid cancer. The solid cancer can be any cancer that arises from organs and solid tissues. In certain embodiments, the solid cancer is stomach cancer, breast cancer, pancreatic cancer, colon cancer, lung cancer or prostate cancer. In particular embodiments, the solid cancer is not breast cancer, lung cancer, prostate cancer, pancreatic cancer or gastrointestinal cancer.

In one embodiment, the at least one miR gene product measured in the test sample is selected from the group consisting of miR-21, miR-191, miR-17-5p and combinations thereof. In another embodiment, the at least one miR gene product measured in the test sample is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

In one embodiment, the solid cancer is breast cancer or lung cancer and the at least one miR gene product measured in the test sample is selected from the group consisting of miR-210, miR-213 and a combination thereof.

In another embodiment, the solid cancer is colon cancer, stomach cancer, prostate cancer or pancreas cancer and the at least one miR gene product measured in the test sample is miR-218-2.

In a certain embodiment, the solid cancer is breast cancer and the at least one miR gene product measured in the test sample is selected from the group consisting of miR-125b-1, miR-125b-2, miR-145, miR-21 and combinations thereof. In a related embodiment, the solid cancer is breast cancer and the at least one miR gene product in the test sample is selected from the group consisting of miR-21, miR-29b-2, miR-146, miR-125b-2, miR-125b-1, miR-10b, miR-145, miR-181a, miR-140, miR-213, miR-29a prec, miR-181b-1, miR-199b, miR-29b-1, miR-130a, miR-155, let-7a-2, miR-205, miR-29c, miR-224, miR-100, miR-31, miR-30c, miR-17-5p, miR-210, miR-122a, miR-16-2 and combinations thereof.

In another embodiment, the solid cancer is colon cancer and the at least one miR gene product in the test sample is selected from the group consisting of miR-24-1, miR-29b-2, miR-20a, miR-10a, miR-32, miR-203, miR-106a, miR-17-5p, miR-30c, miR-223, miR-126*, miR-128b, miR-21, miR-24-2, miR-99b prec, miR-155, miR-213, miR-150, miR-107, miR-191, miR-221, miR-9-3 and combinations thereof.

In yet another embodiment, the solid cancer is lung cancer and the miR gene product in the test sample is selected from the group consisting of miR-21, miR-205, miR-200b, miR-9-1, miR-210, miR-148, miR-141, miR-132, miR-215, miR-128b, let-7g, miR-16-2, miR-129-1/2 prec, miR-126*, miR-142-as, miR-30d, miR-30a-5p, miR-7-2, miR-199a-1, miR-127, miR-34a prec, miR-34a, miR-136, miR-202, miR-196-2, miR-199a-2, let-7a-2, miR-124a-1, miR-149, miR-17-5p, miR-196-1 prec, miR-10a, miR-99b prec, miR-196-1, miR-199b, miR-191, miR-195, miR-155 and combinations thereof.

In an additional embodiment, the solid cancer is pancreatic cancer and the at least one miR gene product measured in the test sample is selected from the group consisting of miR-103-1, miR-103-2, miR-155, miR-204 and combinations thereof. In a related embodiment, the solid cancer is pancreatic cancer and the miR gene product in the test sample is selected from the group consisting of miR-103-2, miR-103-1, miR-24-2, miR-107, miR-100, miR-125b-2, miR-125b-1, miR-24-1, miR-191, miR-23a, miR-26a-1, miR-125a, miR-130a, miR-26b, miR-145, miR-221, miR-126*, miR-16-2, miR-146, miR-214, miR-99b, miR-128b, miR-155, miR-29b-2, miR-29a, miR-25, miR-16-1, miR-99a, miR-224, miR-30d, miR-92-2, miR-199a-1, miR-223, miR-29c, miR-30b, miR-129-1/2, miR-197, miR-17-5p, miR-30c, miR-7-1, miR-93-1, miR-140, miR-30a-5p, miR-132, miR-181b-1, miR-152 prec, miR-23b, miR-20a, miR-222, miR-27a, miR-92-1, miR-21, miR-129-112 prec, miR-150, miR-32, miR-106a, miR-29b-1 and combinations thereof.

In another embodiment, the solid cancer is prostate cancer and the miR gene product in the test sample is selected from the group consisting of let-7d, miR-128a prec, miR-195, miR-203, let-7a-2 prec, miR-34a, miR-20a, miR-218-2, miR-29a, miR-25, miR-95, miR-197, miR-135-2, miR-187, miR-196-1, miR-148, miR-191, miR-21, let-71, miR-198, miR-199a-2, miR-30c, miR-17-5p, miR-92-2, miR-146, miR-181b-1 prec, miR-32, miR-206, miR-184 prec, miR-29a prec, miR-29b-2, miR-149, miR-181b-1, miR-196-1 prec, miR-93-1, miR-223, miR-16-1, miR-101-1, miR-124a-1, miR-26a-1, miR-214, miR-27a, miR-24-1, miR-106a, miR-199a-1 and combinations thereof.

In yet another embodiment, the solid cancer is stomach cancer and the miR gene product in the test sample is selected from the group consisting of miR-223, miR-21, miR-218-2, miR-103-2, miR-92-2, miR-25, miR-136, miR-191, miR-221, miR-125b-2, miR-103-1, miR-214, miR-222, miR-212 prec, miR-125b-1, miR-100, miR-107, miR-92-1, miR-96, miR-192, miR-23a, miR-215, miR-7-2, miR-138-2, miR-24-1, miR-99b, miR-33b, miR-24-2 and combinations thereof.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., hybridizing to a microarray that comprises several miRNA-specific probe oligonucleotides) to provide a hybridization profile for the test sample, and comparing the test sample hybridization profile to a hybridization profile from a control sample. An alteration in the signal of at least one miRNA in the test sample relative to the control sample is indicative of the subject either having, or being at risk for developing, a solid cancer. In a particular embodiment, target oligonucleotides are hybridized to a microarray comprising miRNA-specific probe oligonucleotides for one or more miRNAs selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention also encompasses methods of inhibiting tumorigenesis in a subject who has, or is suspected of having, a solid cancer (e.g., prostate cancer, stomach cancer, pancreatic cancer, lung cancer, breast cancer, colon cancer), wherein at least one miR gene product is deregulated (e.g., down-regulated, up-regulated) in the cancer cells of the subject. When the at least one isolated miR gene product is down-regulated in the cancer cells, the method comprises administering an effective amount of an isolated miR gene product, an isolated variant or a biologically-active fragment of the miR gene product or variant, such that proliferation of cancer cells in the subject is inhibited. In a further embodiment, the at least one isolated miR gene product is selected from the group consisting of miR-145, miR-155, miR-218-2 and combinations thereof. In a particular embodiment, the miR gene product is not miR-15a or miR-16-1. When the at least one isolated miR gene product is up-regulated in the cancer cells, the method comprises administering to the subject an effective amount of at least one compound for inhibiting expression of the at least one miR gene product (referred to herein as a "miR expression-inhibition compound"), such that proliferation of cancer cells in the subject is inhibited. In a particular embodiment, the at least one miR expression-inhibition compound is specific for a miR gene product selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

In a related embodiment, the methods of inhibiting tumorigenesis in a subject additionally comprise the step of determining the amount of at least one miR gene product in cancer cells from the subject, and comparing that level of the miR gene product in the cells to the level of a corresponding miR gene product in control cells. If expression of the miR gene product is deregulated (e.g., down-regulated, up-regulated) in cancer cells, the methods further comprise altering the amount of the at least one miR gene product expressed in the cancer cells. In one embodiment, the amount of the miR gene product expressed in the cancer cells is less than the amount of the miR gene product expressed in a control cell (e.g., control cells), and an effective amount of the down-regulated miR gene product, isolated variant or biologically-active fragment of the miR gene product or variant, is administered to the subject. Suitable miR gene products for this embodiment include miR-145, miR-155, miR-218-2 and combinations thereof, among others. In a particular embodiment, the miR gene product is not miR-15a or miR-16-1. In another embodiment, the amount of the miR gene product expressed in the cancer cells is greater than the amount of the miR gene product expressed in the control cell (e.g., control cells), and an effective amount of at least one compound for inhibiting expression of the at least one up-regulated miR gene product is administered to the subject. Suitable compounds for inhibiting expression of the at least one miR gene product include, but are not limited to, compounds that inhibit the expression of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention further provides pharmaceutical compositions for treating solid cancers (e.g., prostate cancer, stomach cancer, pancreatic cancer, lung cancer, breast cancer, colon cancer). In one embodiment, the pharmaceutical compositions comprise at least one isolated miR gene product and a pharmaceutically-acceptable carrier. In a particular embodiment, the at least one miR gene product corresponds to a miR gene product that has a decreased level of expression in cancer cells relative to control cells. In certain embodiments the isolated miR gene product is selected from the group consisting of miR-145, miR-155, miR-218-2 and combinations thereof.

In another embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in cancer cells than in control cells. In certain embodiments, the miR expression-inhibition compound is specific for one or more miR gene products selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention also encompasses methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in solid cancers (e.g., prostate cancer, stomach cancer, pancreatic cancer, lung cancer, breast cancer, colon cancer). An increase in the level of the miR gene product in the cell, relative to a suitable control cell, is indicative of the test agent being an inhibitor of tumorigenesis. In a particular embodiment, the at least one miR gene product associated with decreased expression levels in solid cancer cells is selected from the group consisting of miR-145, miR-155, miR-218-2 and combinations thereof.

In other embodiments, the method comprises providing a test agent to a cell and measuring the level of at least one miR gene product associated with increased expression levels in solid cancers. A decrease in the level of the miR gene product in the cell, relative to a suitable control cell, is indicative of the test agent being an inhibitor of tumorigenesis. In a particular embodiment, the at least one miR gene product associated with increased expression levels in solid cancer cells is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

BRIEF DESCRIPTION OF THE DRAWINGS

Figure 8:
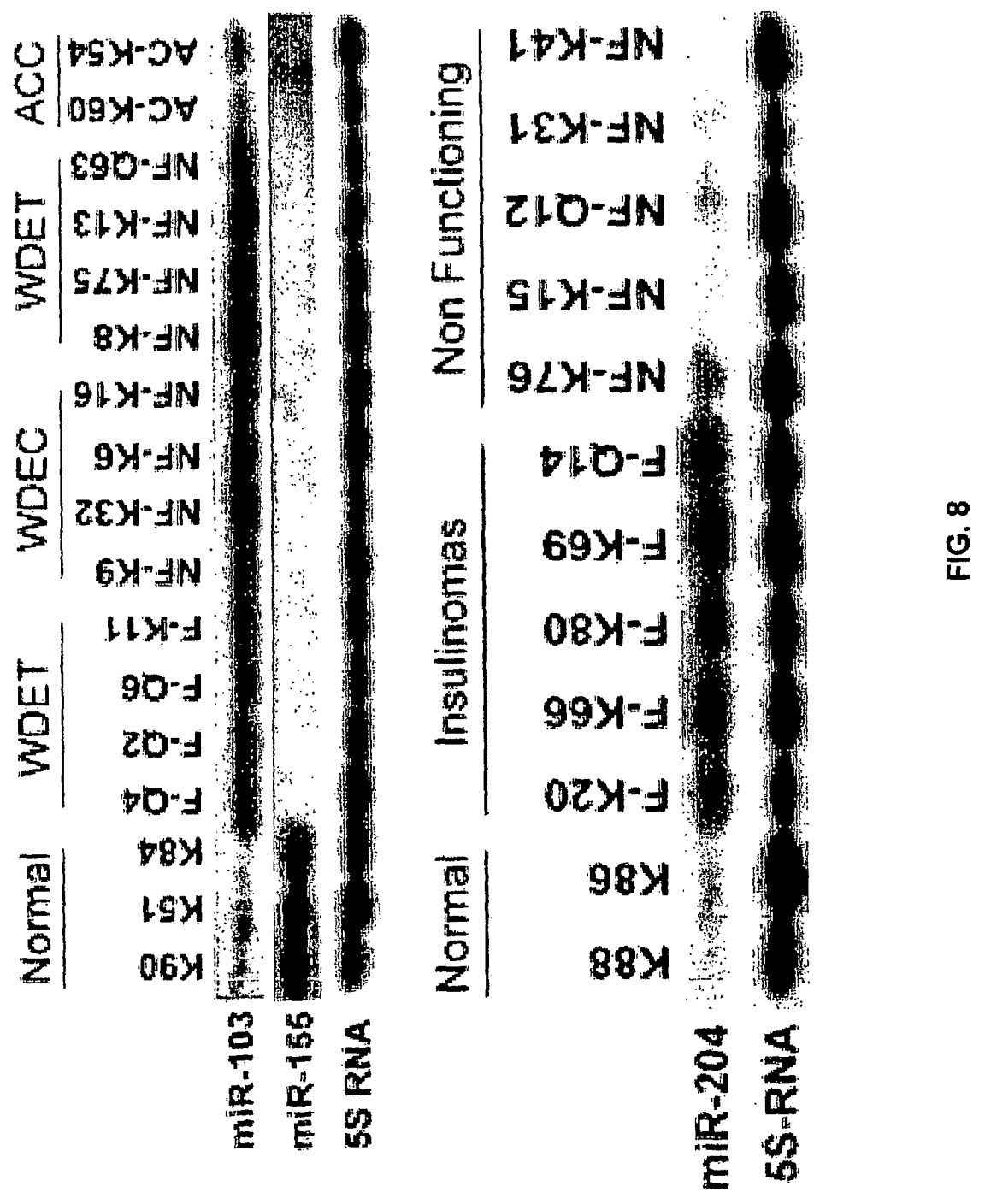

FIG. 8 depicts Northern blots showing up-regulation of miR-103 and down-regulation miR-155 (top) expression in different endocrine pancreatic cancer samples (WDET, well differentiated pancreatic endocrine tumors, WDEC, well differentiated pancreatic endocrine carcinomas and ACC, pancreatic acinar cell carcinomas) relative to normal samples (K series), as well as up-regulation of miR-204 (bottom) expression in insulinomas (F series) relative to normal samples (K series) and non secreting/non functioning (NF-series) samples. Normalization was performed with a probe specific to 5S RNA.

DETAILED DESCRIPTION OF THE INVENTION

Figure 1:
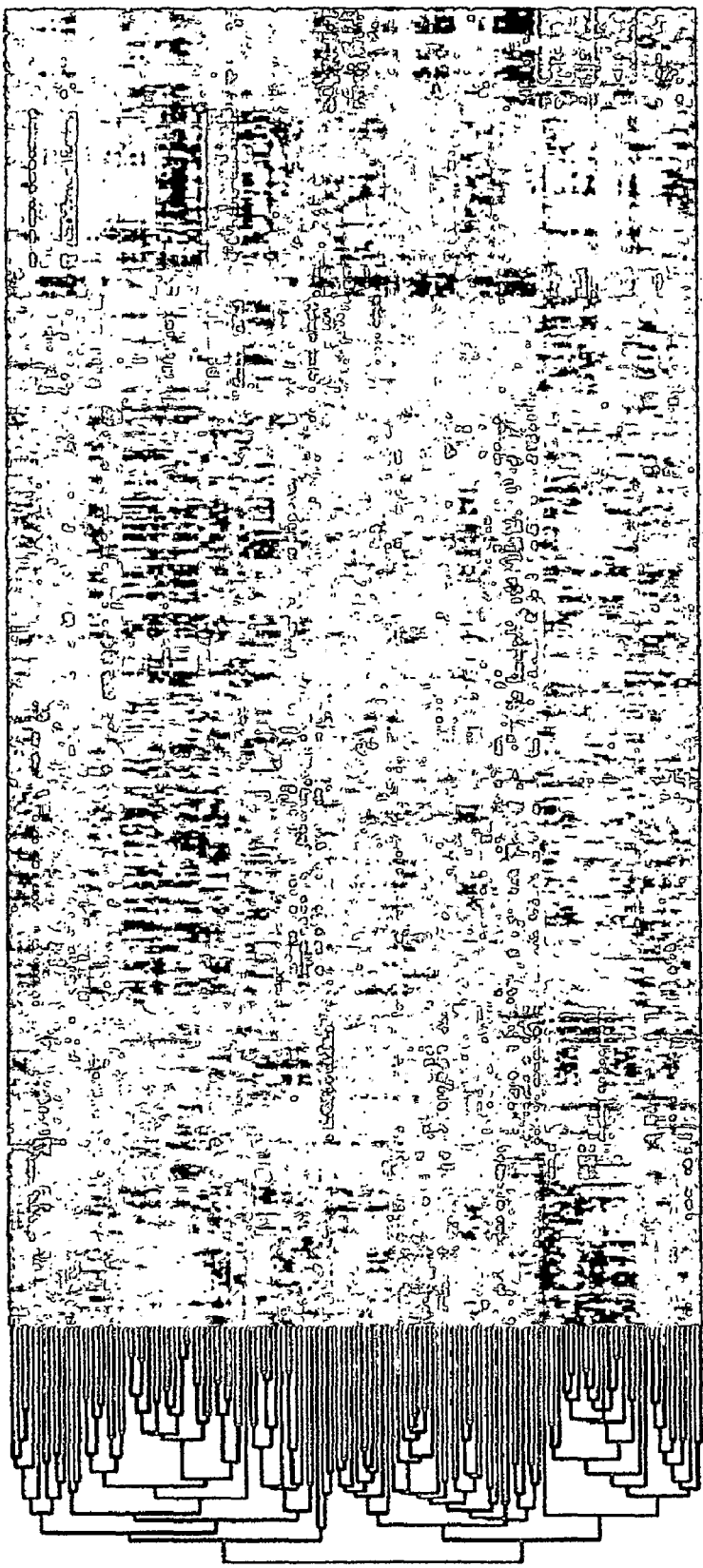
FIG. 1 depicts a clustering analysis of 540 samples, representing 6 solid cancers (top) and the respective normal tissues. miRNAs included in the tree (n=137) represent those whose expression level (background-subtracted intensity) was higher than the threshold value (256) in at least 50% of the samples analyzed. Arrays were median-centered and normalized using Gene Cluster 2.0. Average linkage clustering was performed by using uncentered correlation metric. The colors indicate the difference in expression level from the median for the microRNAs in each sample.

The present invention is based, in part, on the identification of particular microRNAs whose expression is altered in cancer cells associated with different solid cancers, such as colon, stomach, pancreatic, lung, breast and prostate cancer, relative to normal control cells.

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having been processed from the miR precursor. When a microRNA is referred to herein by name, the name corresponds to both the precursor and mature forms, unless otherwise indicated.

Tables 1a and 1b depict the nucleotide sequences of particular precursor and mature human microRNAs.

TABLE 1a

Human microRNA Precursor Sequences.

| Precursor Name | Sequence (5' To 3')* | SEQ ID NO. |
|---|---|---|
| let-7a-1 | CACUGUGGGAUGAGGUAGUAGGUUGUAUAGUU UUAGGGUCACACCCACCACUGGGAGAUAACUA UACAAUCUACUGUCUUUCCUAACGUG | 1 |
| let-7a-2 | AGGUUGAGGUAGUAGGUUGUAUAGUUUAGAAU UACAUCAAGGGAGAUAACUGUACAGCCUCCUA GCUUUCCU | 2 |

TABLE 1a-continued

Human microRNA Precursor Sequences.

| Precursor Name | Sequence (5' To 3')* | SEQ ID NO. |
|---|---|---|
| let-7a-3 | GGGUGAGGUAGUAGGUUGUAUAGUUUGGGGCU CUGCCCUGCUAUGGGAUAACUAUACAAUCUAC UGUCUUUCCU | 3 |
| let-7a-4 | GUGACUGCAUGCUCCCAGGUUGAGGUAGUAGG UUGUAUAGUUUAGAAUUACACAAGGGAGAUAA CUGUACAGCCUCCUAGCUUUCCUUGGGUCUUG CACUAAACAAC | 4 |
| let-7b | GGCGGGGUGAGGUAGUAGGUUGUGUGGUUUCA GGGCAGUGAUGUUGCCCCUCGGAAGAUAACUA UACAACCUACUGCCUUCCCUG | 5 |
| let-7c | GCAUCCGGGUUGAGGUAGUAGGUUGUAUGGUU UAGAGUUACACCCUGGGAGUUAACUGUACAAC CUUCUAGCUUUCCUUGGAGC | 6 |
| let-7d | CCUAGGAAGAGGUAGUAGGUUGCAUAGUUUUA GGGCAGGGAUUUUGCCCACAAGGAGGUAACUA UACGACCUGCUGCCUUUCUUAGG | 7 |
| let-7d-v1 | CUAGGAAGAGGUAGUAGUUUGCAUAGUUUUAG GGCAAAGAUUUUGCCCACAAGUAGUUAGCUAU ACGACCUGCAGCCUUUUGUAG | 8 |
| let-7d-v2 | CUGGCUGAGGUAGUAGUUUGUGCUGUUGGUCG GGUUGUGACAUUGCCCGCUGUGGAGAUAACUG CGCAAGCUACUGCCUUGCUAG | 9 |
| let-7e | CCCGGGCUGAGGUAGGAGGUUGUAUAGUUGAG GAGGACACCCAAGGAGAUCACUAUACGGCCUC CUAGCUUUCCCCAGG | 10 |
| let-7f-1 | UCAGAGUGAGGUAGUAGAUUGUAUAGUUUGGG GGUAGUGAUUUUACCCUGUUCAGGAGAUAACU AUACAAUCUAUUGCCUUCCCUGA | 11 |
| let-7f-2-1 | CUGUGGGAUGAGGUAGUAGAUUGUAUAGUUGU GGGGUAGUGAUUUUACCCUGUUCAGGAGAUAA CUAUACAAUCUAUUGCCUUCCCUGA | 12 |
| let-7f-2-2 | CUGUGGGAUGAGGUAGUAGAUUGUAUAGUUUU AGGGUCAUACCCCAUCUUGGAGAUAACUAUAC AGUCUACUGUCUUUCCCACGG | 13 |
| let-7g | UUGCCUGAUUCCAGGCUGAGGUAGUAGUUUGU ACAGUUUGAGGGUCUAUGAUACCACCCGGUAC AGGAGAUAACUGUACAGGCCACUGCCUUGCCA GGAACAGCGCGC | 14 |
| let-7i | CUGGCUGAGGUAGUAGUUUGUGCUGUUGGUCG GGUUGUGACAUUGCCCGCUGUGGAGAUAACUG CGCAAGCUACUGCCUUGCUAG | 15 |
| miR-1b-1-1 | ACCUACUCAGAGUACAUACUUCUUUAUGUACC CAUAUGAACAUACAAUGCUAUGGAAUGUAAAG AAGUAUGUAUUUUUGGUAGGC | 16 |
| miR-1b-1-2 | CAGCUAACAACUUAGUAAUACCUACUCAGAGU ACAUACUUCUUUAUGUACCCAUAUGAACAUAC AAUGCUAUGGAAUGUAAAGAAGUAUGUAUUUU UGGUAGGCAAUA | 17 |
| miR-1b-2 | GCCUGCUUGGGAAACAUACUUCUUUAUAUGCC CAUAUGGACCUGCUAAGCUAUGGAAUGUAAAG AAGUAUGUAUCUCAGGCCGGG | 18 |
| miR-1b | UGGGAAACAUACUUCUUUAUAUGCCCAUAUGG ACCUGCUAAGCUAUGGAAUGUAAAGAAGUAUG UAUCUCA | 19 |
| miR-1d | ACCUACUCAGAGUACAUACUUCUUUAUGUACC CAUAUGAACAUACAAUGCUAUGGAAUGUAAAG AAGUAUGUAUUUUUGGUAGGC | 20 |
| miR-7-1a | UGGAUGUUGGCCUAGUUCUGUGUGGAAGACUA GUGAUUUUGUUGUUUUUAGAUAACUAAAUCGA CAACAAAUCACAGUCUGCCAUAUGGCACAGGC CAUGCCUCUACA | 21 |
| miR-7-1b | UUGGAUGUUGGCCUAGUUCUGUGUGGAAGACU AGUGAUUUUGUUGUUUUUAGAUAACUAAAUCG ACAACAAAUCACAGUCUGCCAUAUGGCACAGG CCAUGCCUCUACAG | 22 |
| miR-7-2 | CUGGAUACAGAGUGGACCGGCUGGCCCCAUCU GGAAGACUAGUGAUUUUGUUGUUGUCUACUG CGCUCAACAACAAAUCCCAGUCUACCUAAUGG UGCCAGCCAUCGCA | 23 |
| miR-7-3 | AGAUUAGAGUGGCUGUGGUCUAGUGCUGUGUG GAAGACUAGUGAUUUUGUUGUUCUGAUGUACU ACGACAACAAGUCACAGCCGGCCUCAUAGCGC AGACUCCCUUCGAC | 24 |
| miR-9-1 | CGGGGUUGGUUGUUAUCUUUGGUUAUCUAGCU GUAUGAGUGGUGUGGAGUCUUCAUAAAGCUAG AUAACCGAAAGUAAAAAUAACCCCA | 25 |
| miR-9-2 | GGAAGCGAGUUGUUAUCUUUGGUUAUCUAGCU GUAUGAGUGUAUUGGUCUUCAUAAAGCUAGAU AACCGAAAGUAAAAACUCCUUCA | 26 |
| miR-9-3 | GGAGGCCCGUUUCUCUCUUUGGUUAUCUAGCU GUAUGAGUGCCACAGAGCCGUCAUAAAGCUAG AUAACCGAAAGUAGAAAUGAUUCUCA | 27 |
| miR-10a | GAUCUGUCUGUCUUCUGUAUAUACCCUGUAGA UCCGAAUUUGUGUAAGGAAUUUUGUGGUCACA AAUUCGUAUCUAGGGGAAUAUGUAGUUGACAU AAACACUCCGCUCU | 28 |
| miR-10b | CCAGAGGUUGUAACGUUGUCUAUAUAUACCCU GUAGAACCGAAUUUGUGUGGUAUCCGUAUAGU CACAGAUUCGAUUCUAGGGGAAUAUAUGGUCG AUGCAAAAACUUCA | 29 |
| miR-15a-2 | GCGCGAAUGUGUGUUUAAAAAAAAUAAAACCU UGGAGUAAAGUAGCAGCACAUAAUGGUUUGUG GAUUUUGAAAAGGUGCAGGCCAUAUUGUGCUG CCUCAAAAAUAC | 30 |
| miR-15a | CCUUGGAGUAAAGUAGCAGCACAUAAUGGUUU GUGGAUUUUGAAAAGGUGCAGGCCAUAUUGUG CUGCCUCAAAAAUACAAGG | 31 |
| miR-15b-1 | CUGUAGCAGCACAUCAUGGUUUACAUGCUACA GUCAAGAUGCGAAUCAUUAUUUGCUGCUCUAG | 32 |
| miR-15b-2 | UUGAGGCCUUAAAGUACUGUAGCAGCACAUCA UGGUUUACAUGCUACAGUCAAGAUGCGAAUCA UUAUUUGCUGCUCUAGAAAUUUAAGGAAAUUC AU | 33 |
| miR-16-1 | GUCAGCAGUGCCUUAGCAGCACGUAAAUAUUG GCGUUAAGAUUCUAAAAUUAUCUCCAGUAUUA ACUGUGCUGCUGAAGUAAGGUUGAC | 34 |
| miR-16-2 | GUUCCACUCUAGCAGCACGUAAAUAUUGGCGU AGUGAAAUAUAUAUUAAACACCAAUAUUACUG UGCUGCUUUAGUGUGAC | 35 |

TABLE 1a-continued

Human microRNA Precursor Sequences.

| Precursor Name | Sequence (5' To 3')* | SEQ ID NO. |
| --- | --- | --- |
| miR-16-13 | GCAGUGCCUUAGCAGCACGUAAAUAUUGGCGU UAAGAUUCUAAAAUUAUCUCCAGUAUUAACUG UGCUGCUGAAGUAAGGU | 36 |
| miR-17 | GUCAGAAUAAUGUCAAAGUGCUUACAGUGCAG GUAGUGAUAUGUGCAUCUACUGCAGUGAAGGC ACUUGUAGCAUUAUGGUGAC | 37 |
| miR-18 | UGUUCUAAGGUGCAUCUAGUGCAGAUAGUGAA GUAGAUUAGCAUCUACUGCCCUAAGUGCUCCU UCUGGCA | 38 |
| miR-18-13 | UUUUUGUUCUAAGGUGCAUCUAGUGCAGAUAG UGAAGUAGAUUAGCAUCUACUGCCCUAAGUGC UCCUUCUGGCAUAAGAA | 39 |
| miR-19a | GCAGUCCUCUGUUAGUUUUGCAUAGUUGCACU ACAAGAAGAAUGUAGUUGUGCAAAUCUAUGCA AAACUGAUGGUGGCCUGC | 40 |
| miR-19a-13 | CAGUCCUCUGUUAGUUUUGCAUAGUUGCACUA CAAGAAGAAUGUAGUUGUGCAAAUCUAUGCAA AACUGAUGGUGGCCUG | 41 |
| miR-19b-1 | CACUGUUCUAUGGUUAGUUUUGCAGGUUUGCA UCCAGCUGUGUGAUAUUCUGCUGUGCAAAUCC AUGCAAAACUGACUGUGGUAGUG | 42 |
| miR-19b-2 | ACAUUGCUACUUACAAUUAGUUUUGCAGGUUU GCAUUUCAGCGUAUAUAUGUAUAUGUGGCUGU GCAAAUCCAUGCAAAACUGAUUGUGAUAAUGU | 43 |
| miR-19b-13 | UUCUAUGGUUAGUUUUGCAGGUUUGCAUCCAG CUGUGUGAUAUUCUGCUGUGCAAAUCCAUGCA AAACUGACUGUGGUAG | 44 |
| miR-19b-X | UUACAAUUAGUUUUGCAGGUUUGCAUUUCAGC GUAUAUAUGUAUAUGUGGCUGUGCAAAUCCAU GCAAAACUGAUUGUGAU | 45 |
| miR-20 (miR-20a) | GUAGCACUAAAGUGCUUAUAGUGCAGGUAGUG UUUAGUUAUCUACUGCAUUAUGAGCACUUAAA GUACUGC | 46 |
| miR-21 | UGUCGGGUAGCUUAUCAGACUGAUGUUGACUG UUGAAUCUCAUGGCAACACCAGUCGAUGGGCU GUCUGACA | 47 |
| miR-21-17 | ACCUUGUCGGGUAGCUUAUCAGACUGAUGUUG ACUGUUGAAUCUCAUGGCAACACCAGUCGAUG GGCUGUCUGACAUUUUG | 48 |
| miR-22 | GGCUGAGCCGCAGUAGUUCUUCAGUGGCAAGC UUUAUGUCCUGACCCAGCUAAAGCUGCCAGUU GAAGAACUGUUGCCCUCUGCC | 49 |
| miR-23a | GGCCGGCUGGGGUUCCUGGGGAUGGGAUUUGC UUCCUGUCACAAAUCACAUUGCCAGGGAUUUC CAACCGACC | 50 |
| miR-23b | CUCAGGUGCUCUGGCUGCUUGGGUUCCUGGCA UGCUGAUUUGUGACUUAAGAUUAAAUCACAUU GCCAGGGAUUACCACGCAACCACGACCUUGG C | 51 |
| miR-23-19 | CCACGCCGGCUGGGGUUCCUGGGGAUGGGAUU UGCUUCCUGUCACAAAUCACAUUGCCAGGGAU UUCCAACCGACCCUGA | 52 |
| miR-24-1 | CUCCGGUGCCUACUGAGCUGAUAUCAGUUCUC AUUUUACACACUGGCUCAGUUCAGCAGGAACA GGAG | 53 |
| miR-24-2 | CUCUGCCUCCCGUGCCUACUGAGCUGAAACAC AGUUGGUUUGUGUACACUGGCUCAGUUCAGCA GGAACAGGG | 54 |
| miR-24-19 | CCCUGGGCUCUGCCUCCCGUGCCUACUGAGCU GAAACACAGUUGGUUUGUGUACACUGGCUCAG UUCAGCAGGAACAGGGG | 55 |
| miR-24-9 | CCCUCCGGUGCCUACUGAGCUGAUAUCAGUUC UCAUUUUACACACUGGCUCAGUUCAGCAGGAA CAGCAUC | 56 |
| miR-25 | GGCCAGUGUUGAGAGGCGGAGACUUGGGCAAU UGCUGGACGCUGCCCUGGGCAUUGCACUUGUC UCGGUCUGACAGUGCCGGCC | 57 |
| miR-26a | AGGCCGUGGCCUCGUUCAAGUAAUCCAGGAUA GGCUGUGCAGGUCCCAAUGGGCCUAUCUUGGUU ACUUGCACGGGGACGCGGGCCU | 58 |
| miR-26a-1 | GUGGCCUCGUUCAAGUAAUCCAGGAUAGGCUG UGCAGGUCCCAAUGGGCCUAUUCUUGGUUACU UGCACGGGGACGC | 59 |
| miR-26a-2 | GGCUGUGGCUGGAUUCAAGUAAUCCAGGAUAG GCUGUUUCCAUCUGUGAGGCCUAUUCUUGAUU ACUUGUUUCUGGAGGCAGCU | 60 |
| miR-26b | CCGGGACCCAGUUCAAGUAAUUCAGGAUAGGU UGUGUGCUGUCCAGCCUGUUCUCCAUUACUUG GCUCGGGGACCGG | 61 |
| miR-27a | CUGAGGAGCAGGGCUUAGCUGCUUGUGAGCAG GGUCCACACCAAGUCGUGUUCACAGUGGCUAA GUUCCGCCCCCCAG | 62 |
| miR-27b-1 | AGGUGCAGAGCUUAGCUGAUUGGUGAACAGUG AUUGGUUUCCGCUUUGUUCACAGUGGCUAAGU UCUGCACCU | 63 |
| miR-27b-2 | ACCUGUCUAACAAGGUGCAGAGCUUAGCUGAU UGGUGAACAGUGAUUGGUUUCCGCUUUGUUCA CAGUGGCUAAGUUCUGCACCUGAAGAGAAGGU G | 64 |
| miR-27-19 | CCGAGGAGCAGGGCUUAGCUGCUUGUGAGCA GGGUCCACACCAAGUCGUGUUCACAGUGGCUA AGUUCCGCCCCCAGG | 65 |
| miR-28 | GGUCCUUGCCCUCAAGGAGCUCACAGUCUAUU GAGUUACCUUUCUGACUUUCCCACUAGAUUGU GAGCUCCUGGAGGGCAGGCACU | 66 |
| miR-29a-2 | CCUUCUGUGACCCCUUAGAGGAUGACUGAUUU CUUUUGGUGUUCAGAGUCAAUAUAAUUUUCUA GCACCAUCUGAAAUCGGUUAUAAUGAUUGGGG AAGAGCACCAUG | 67 |
| miR-29a | AUGACUGAUUUCUUUUGGUGUUCAGAGUCAAU AUAAUUUUCUAGCACCAUCUGAAAUCGGUUAU | 68 |
| miR-29b-1 | CUUCAGGAAGCUGGUUUCAUAUGGUGGUUUAG AUUUAAAUAGUGAUUGUCUAGCACCAUUUGAA AUCAGUGUUCUUGGGGG | 69 |
| miR-29b-2 | CUUCUGGAAGCUGGUUUCACAUGGUGGCUUAG AUUUUUCCAUCUUUGUAUCUAGCACCAUUUGA AAUCAGUGUUUUAGGAG | 70 |
| miR-29c | ACCACUGGCCCAUCUCUUACACAGGCUGACCG AUUUCUCCUGGUGUUCAGAGUCUGUUUUUGUC UAGCACCAUUUGAAAUCGGUUAUGAUGUAGGG GGAAAAGCAGCAGC | 71 |

TABLE 1a-continued

Human microRNA Precursor Sequences.

| Precursor Name | Sequence (5' To 3')* | SEQ ID NO. |
|---|---|---|
| miR-30a | GCGACUGUAAACAUCCUCGACUGGAAGCUGUG AAGCCACAGAUGGGCUUUCAGUCGGAUGUUUG CAGCUGC | 72 |
| miR-30b-1 | AUGUAAACAUCCUACACUCAGCUGUAAUACAU GGAUUGGCUGGGAGGUGGAUGUUUACGU | 73 |
| miR-30b-2 | ACCAAGUUUCAGUUCAUGUAAACAUCCUACAC UCAGCUGUAAUACAUGGAUUGGCUGGGAGGUG GAUGUUUACUUCAGCUGACUUGGA | 74 |
| miR-30c | AGAUACUGUAAACAUCCUACACUCUCAGCUGU GGAAAGUAAGAAAGCUGGGAGAAGGCUGUUUA CUCUUUCU | 75 |
| miR-30d | GUUGUUGUAAACAUCCCCGACUGGAAGCUGUA AGACACAGCUAAGCUUUCAGUCAGAUGUUUGC UGCUAC | 76 |
| miR-30e | CUGUAAACAUCCUUGACUGGAAGCUGUAAGGU GUUCAGAGGAGCUUUCAGUCGGAUGUUUACAG | 77 |
| miR-31 | GGAGAGGAGGCAAGAUGCUGGCAUAGCUGUUG AACUGGGAACCUGCUAUGCCAACAUAUUGCCA UCUUUCC | 78 |
| miR-32 | GGAGAUAUUGCACAUUACUAAGUUGCAUGUUG UCACGGCCUCAAUGCAAUUUAGUGUGUGUGAU AUUUUC | 79 |
| miR-33b | GGGGGCCGAGAGAGGCGGGCGGCCCCGCGGUG CAUUGCUGUUGCAUUGCACGUGUGUGAGGCGG GUGCAGUGCCUCGGCAGUGCAGCCCGGAGCCG GCCCCUGGCACCAC | 80 |
| miR-33b-2 | ACCAAGUUUCAGUUCAUGUAAACAUCCUACAC UCAGCUGUAAUACAUGGAUUGGCUGGGAGGUG GAUGUUUACUUCAGCUGACUUGGA | 81 |
| miR-33 | CUGUGGUGCAUUGUAGUUGCAUUGCAUGUUCU GGUGGUACCCAUGCAAUGUUUCCACAGUGCAU CACAG | 82 |
| miR-34-a | GGCCAGCUGUGAGUGUUUCUUUGGCAGUGUCU UAGCUGGUUGUUGUGAGCAAUAGUAAGGAAGC AAUCAGCAAGUAUACUGCCCUAGAAGUGCUGC ACGUUGUGGGCCC | 83 |
| miR-34-b | GUGCUCGGUUUGUAGGCAGUGUCAUUAGCUGA UUGUACUGUGGUGGUUACAAUCACUAACUCCA CUGCCAUCAAAACAAGGCAC | 84 |
| miR-34-c | AGUCUAGUUACUAGGCAGUGUAGUUAGCUGAU UGCUAAUAGUACCAAUCACUAACCACACGGCC AGGUAAAAAGAUU | 85 |
| miR-91-13 | UCAGAAUAAUGUCAAAGUGCUUACAGUGCAGG UAGUGAUAUGUGCAUCUACUGCAGUGAAGGCA CUUGUAGCAUUAUGGUGA | 86 |
| miR-92-1 | CUUUCUACACAGGUUGGGAUCGGUUGCAAUGC UGUGUUUCUGUAUGGUAUUGCACUUGUCCCGG CCUGUUGAGUUUGG | 87 |
| miR-92-2 | UCAUCCCUGGGUGGGGAUUUGUUGCAUUACUU GUGUUCUAUAUAAAGUAUUGCACUUGUCCCGG CCUGUGGAAGA | 88 |
| miR-93-1 (miR-93-2) | CUGGGGGCUCCAAAGUGCUGUUCGUGCAGGUA GUGAUUUACCCAACCUACUGCUGAGCUAGCA CUUCCCGAGCCCCGG | 89 |
| miR-95-4 | AACACAGUGGGCACUCAAUAAAUGUCUGUUGA AUUGAAAUGCGUUACAUUCAACGGGUAUUUAU UGAGCACCCACUCUGUG | 90 |
| miR-96-7 | UGGCCGAUUUUGGCACUAGCACAUUUUUGCUU GUGUCUCUCCGCUCUGAGCAAUCAUGUGCAGU GCCAAUAUGGGAAA | 91 |
| miR-97-6 (miR-30*) | GUGAGCGACUGUAAACAUCCUCGACUGGAAGC UGUGAAGCCACAGAUGGGCUUUCAGUCGGAUG UUUGCAGCUGCCUACU | 92 |
| miR-98 | GUGAGGUAGUAAGUUGUAUUGUUGUGGGGUA GGGAUAUUAGGCCCCAAUUAGAAGAUAACUAU ACAACUUACUACUUUCC | 93 |
| miR-99b | GGCACCCACCCGUAGAACCGACCUUGCGGGGC CUUCGCCGCACACAAGCUCGUGUCUGUGGGUC CGUGUC | 94 |
| miR-99a | CCCAUUGGCAUAAACCCGUAGAUCCGAUCUUG UGGUGAAGUGGACCGCACAAGCUCGCUUCUAU GGGUCUGUGUCAGUGUG | 95 |
| miR-100-1/2 | AAGAGAGAAGAUAUUGAGGCCUGUUGCCACAA ACCCGUAGAUCCGAACUUGUGGUAUUAGUCCG CACAAGCUUGUAUCUAUAGGUAUGUGUCUGUU AGGCAAUCUCAC | 96 |
| miR-100-11 | CCUGUUGCCACAAACCCGUAGAUCCGAACUUG UGGUAUUAGUCCGCACAAGCUUGUAUCUAUAG GUAUGUGUCUGUUAGG | 97 |
| miR-101-1/2 | AGGCUGCCCUGGCUCAGUUAUCACAGUGCUGA UGCUGUCUAUUCUAAAGGUACAGUACUGUGAU AACUGAAGGAUGGCAGCCAUCUACUUCCAU CAGAGGAGCCUCAC | 98 |
| miR-101 | UCAGUUAUCACAGUGCUGAUGCUGUGCAUUCU AAAGGUACAGUACUGUGAUAACUGA | 99 |
| miR-101-1 | UGCCCUGGCUCAGUUAUCACAGUGCUGAUGCU GUCUAUUCUAAAGGUACAGUACUGUGAUAACU GAAGGAUGGCA | 100 |
| miR-101-2 | ACUGUCCUUUUCGGUUAUCAUGGUACCGAUG CUGUAUAUCUGAAAGGUACAGUACUGUGAUAA CUGAAGAAUGGUGGU | 101 |
| miR-101-9 | UGUCCUUUUCGGUUAUCAUGGUACCGAUGCU GUAUAUCUGAAAGGUACAGUACUGUGAUAACU GAAGAAUGGUG | 102 |
| miR-102-1 | CUUCGGAAGCUGGUUUCACAUGGUGGCUUAG AUUUUUCCAUCUUUGUAUCUAGCACCAUUUGA AAUCAGUGUUUUAGGAG | 103 |
| miR-102-7.1 (miR-102-7.2) | CUUCAGGAAGCUGGUUUCAUAUGGUGGUUUAG AUUUAAAUAGUGAUUGUCUAGCACCAUUUGAA AUCAGUGUUCUUGGGGG | 104 |
| miR-103-2 | UUGUGCUUUCAGCUUCUUUACAGUGCUGCCUU GUAGCAUUCAGGUCAGCAACAUUGUACAGGG CUAUGAAAGAACCA | 105 |
| miR-103-1 | UACUGCCCUCGGCUUCUUUACAGUGCUGCCUU GUUGCAUAUGGAUCAAGCAGCAUUGUACAGGG CUAUGAAGGCAUUG | 106 |
| miR-104-17 | AAAUGUCAGCAGCCCAUCGACUGGUGUUGCC AUGAGAUUCAACAGUCAACAUCAGUCUGAUAA GCUACCCGACAAGG | 107 |

TABLE 1a-continued

Human microRNA Precursor Sequences.

| Precursor Name | Sequence (5' To 3')* | SEQ ID NO. |
|---|---|---|
| miR-105-1 | UGUGCAUCGUGGUCAAAUGCUCAGACUCCUGU GGUGGCUGCUCAUGCACCACGGAUGUUUGAGC AUGUGCUACGGUGUCUA | 108 |
| miR-105-2 | UGUGCAUCGUGGUCAAAUGCUCAGACUCCUGU GGUGGCUGCUUAUGCACCACGGAUGUUUGAGC AUGUGCUAUGGUGUCUA | 109 |
| miR-106-a | CCUUGGCCAUGUAAAAGUGCUUACAGUGCAGG UAGCUUUUUGAGAUCUACUGCAAUGUAAGCAC UUCUUACAUUACCAUGG | 110 |
| miR-106-b | CCUGCCGGGGCUAAAGUGCUGACAGUGCAGAU AGUGGUCCUCUCCGUGCUACCGCACUGUGGGU ACUUGCUGCUCCAGCAGG | 111 |
| miR-107 | CUCUCUGCUUUCAGCUUCUUUACAGUGUUGCC UUGUGGCAUGGAGUUCAAGCAGCAUUGUACAG GGCUAUCAAAGCACAGA | 112 |
| miR-108-1-small | ACACUGCAAGAACAAUAAGGAUUUUUAGGGGC AUUAUGACUGAGUCAGAAAACACAGCUGCCCC UGAAAGUCCCUCAUUUUUCUUGCUGU | 113 |
| miR-108-2-small | ACUGCAAGAGCAAUAAGGAUUUUUAGGGGCAU UAUGAUAGUGGAAUGGAAACAUCUGCCCCC AAAAGUCCCUCAUUUU | 114 |
| miR-122a-1 | CCUUAGCAGAGCUGUGGAGUGUGACAAUGGUG UUUGUGUCUAAACUAUCAAACGCCAUUAUCAC ACUAAAUAGCUACUGCUAGGC | 115 |
| miR-122a-2 | AGCUGUGGAGUGUGACAAUGGUGUUUGUGUCC AAACUAUCAAACGCCAUUAUCACACUAAAUAG CU | 116 |
| miR-123 | ACAUUAUUACUUUUGGUACGCGCUGUGACACU UCAAACUCGUACCGUGAGUAAUAAUGCGC | 117 |
| miR-124a-1 | AGGCCUCUCUCUCCGUGUUCACAGCGGACCUU GAUUUAAAUGUCCAUACAAUUAAGGCACGCGG UGAAUGCCAAGAAUGGGGCUG | 118 |
| miR-124a-2 | AUCAAGAUUAGAGGCUCUGCUCUCCGUGUUCA CAGCGGACCUUGAUUUAAUGUCAUACAAUUAA GGCACGCGGUGAAUGCCAAGAGCGGAGCCUAC GGCUGCACUUGAAG | 119 |
| miR-124a-3 | UGAGGGCCCCUCUGCGUGUUCACAGCGGACCU UGAUUUAAUGUCUAUACAAUUAAGGCACGCGG UGAAUGCCAAGAGAGGCGCCUCC | 120 |
| miR-124a | CUCUGCGUGUUCACAGCGGACCUUGAUUUAAU GUCUAUACAAUUAAGGCACGCGGUGAAUGCCA AGAG | 121 |
| miR-124b | CUCUCCGUGUUCACAGCGGACCUUGAUUUAAU GUCAUACAAUUAAGGCACGCGGUGAAUGCCAA GAG | 122 |
| miR-125a-1 | UGCCAGUCUCUAGGUCCCUGAGACCCUUUAAC CUGUGAGGACAUCCAGGGUCACAGGUGAGGUU CUUGGGAGCCUGGCGUCUGGCC | 123 |
| miR-125a-2 | GGUCCCUGAGACCCUUUAACCUGUGAGGACAU CCAGGGUCACAGGUGAGGUUCUUGGGAGCCUG G | 124 |
| miR-125b-1 | UGCGCUCCUCUCAGUCCCUGAGACCCUAACUU GUGAUGUUUACCGUUUAAAUCCACGGGUUAGG CUCUUGGGAGCUGCGAGUCGUGCU | 125 |
| miR-125b-2 | ACCAGACUUUUCCUAGUCCCUGAGACCCUAAC UUGUGAGGUAUUUUAGUAACAUCACAAGUCAG GCUCUUGGGACCUAGGCGGAGGGGA | 126 |
| miR-126-1 | CGCUGGCGACGGACAUUAUUACUUUUGGUAC GCGCUGUGACAGUUCAAACUCGUACCGUGAGU AAUAAUGCGCCGUCCACGGCA | 127 |
| miR-126-2 | ACAUUAUUACUUUUGGUACGCGCUGUGACACU UCAAACUCGUACCGUGAGUAAUAAUGCGC | 128 |
| miR-127-1 | UGUGAUCACUGUCUCCAGCCUGCUGAAGCUCA GAGGGCUCUGAUUCAGAAAGAUCAUCGGAUCC GUCUGAGCUUGGCUGGUCGGAAGUCUCAUCAU C | 129 |
| miR-127-2 | CCAGCCUGCUGAAGCUCAGAGGGCUCUGAUUC AGAAAGAUCAUCGGAUCCGUCUGAGCUUGGCU GGUCGG | 130 |
| miR-128a | UGAGCUGUUGGAUUCGGGGCCGUAGCACUGUC UGAGAGGUUUACAUUUCUCACAGUGAACCGGU CUCUUUUCAGCUGCUUC | 131 |
| miR-128b | GCCCGGCAGCCACUGUGCAGUGGGAAGGGGGG CCGAUACACUGUACGAGAGUGAGUAGCAGGUC UCACAGUGAACCGGUCUCUUUCCCUACUGUGU CACACUCCUAAUGG | 132 |
| miR-128 | GUUGGAUUCGGGGCCGUAGCACUGUCUGAGAG GUUUACAUUUCUCACAGUGAACCGGUCUCUUU UUCAGC | 133 |
| miR-129-1 | UGGAUCUUUUUGCGGUCUGGGCUUGCUGUUCC UCUCAACUAGUCAGGAAGCCCUUACCCCAA AAAGUAUCUA | 134 |
| miR-129-2 | UGCCCUUCGCGAAUCUUUUUGCGGUCUGGGCU UGCUGUACAUUAACUCAAUAGCCGGAAGCCCUU ACCCCAAAAAGCAUUUGCGGAGGGCG | 135 |
| miR-130a | UGCUGCUGGCCAGAGCUCUUUUCACAUUGUGC UACUGUCUGCACCUGUCACUAGCAGUGCAAUG UUAAAAGGGCAUUGGCCGUGUAGUG | 136 |
| miR-131-1 | GCCAGGAGGCGGGGUUGGUUGUUAUCUUUGGU UAUCUAGCUGUAUGAGUGUGUGGAGUCUUCA UAAAGCUAGAUAACCGAAAGUAAAAAUAACCC CAUACACUGCGCAG | 137 |
| miR-131-3 | CACGGCGCGGCAGCGGCACUGGCUAAGGGAGG CCCGUUUCUCUCUUUGGUUAUCUAGCUGUAUG AGUGCCACAGAGCCGUCAUAAAGCUAGAUAAC CGAAAGUAGAAAUG | 138 |
| miR-131 | GUUGUUAUCUUUGGUUAUCUAGCUGUAUGAGU GUAUUGGUCUUCAUAAAGCUAGAUAACCGAAA GUAAAAAC | 139 |
| miR-132-1 | CCGCCCCCGCGUCUCCAGGGCAACCGUGGCUU UCGAUUGUUACUGUGGGAACUGGAGGUAACAG UCUACAGCCAUGGUCGCCCCGCAGCGCCCA CGCGC | 140 |
| miR-132-2 | GGGCAACCGUGGCUUUCGAUUGUUACUGUGGG AACUGGAGGUAACAGUCUACAGCCAUGGUCGC CC | 141 |
| miR-133a-1 | ACAAUGCUUUGCUAGAGCUGGUAAAAUGGAAC CAAAUCGCCUCUUCAAUGGAUUUGGUCCCCUU CAACCAGCUGUAGCUAUGCAUUGA | 142 |

TABLE 1a-continued

Human microRNA Precursor Sequences.

| Precursor Name | Sequence (5' To 3')* | SEQ ID NO. |
|---|---|---|
| miR-133a-2 | GGGAGCCAAAUGCUUUGCUAGAGCUGGUAAAAUGGAACCAAAUCGACUGUCCAAUGGAUUUGGUCCCCUUCAACCAGCUGUAGCUGUGCAUUGAUGGCGCCG | 143 |
| miR-133 | GCUAGAGCUGGUAAAAUGGAACCAAAUCGCCUCUUCAAUGGAUUUGGUCCCCUUCAACCAGCUGUAGC | 144 |
| miR-133b | CCUCAGAAGAAAGAUGCCCCCUGCUCUGGCUGGUCAAACGGAACCAAGUCCGUCUUCCUGAGAGGUUUGGUCCCCUUCAACCAGCUACAGCAGGGCUGGCAAUGCCCAGUCCUUGGAGA | 145 |
| miR-133b-small | GCCCCCUGCUCUGGCUGGUCAAACGGAACCAAGUCCGUCUUCCUGAGAGGUUUGGUCCCCUUCAACCAGCUACAGCAGGG | 146 |
| miR-134-1 | CAGGGUGUGUGACUGGUUGACCAGAGGGGCAUGCACUGGUUCACCCUGUGGGCCACCUAGUCACCAACCCUC | 147 |
| miR-134-2 | AGGGUGUGUGACUGGUUGACCAGAGGGGCAUGCACUGUGUUCACCCUGUGGGCCACCUAGUCACCAACCCU | 148 |
| miR-135a-1 | AGGCCUCGCUGUUCUCUAUGGCUUUUUAUUCCUAUGUGAUUCUACUGCUCACUCAUAUAGGGAUUGGAGCCGUGGCGCACGGCGGGACA | 149 |
| miR-135a-2 (miR-135-2) | AGAUAAAUUGACUCUAGUGCUUUAUGGCUUUUUAUUCCUAUGUGAUAGUAAUAAAGUCUCAUGUAGGGAUGGAAGCCAUGAAAUACAUUGUGAAAAUCA | 150 |
| miR-135 | CUAUGGCUUUUUAUUCCUAUGUGAUUCUACUGCUCACUCAUAUAGGGAUUGGAGCCGUGG | 151 |
| miR-135b | CACUCUGCUGUGGCCUAUGGCUUUUCAUUCCUAUGUGAUUGCUGUCCCAAACUCAUGUAGGGCUAAAAGCCAUGGGCUACAGUGAGGGGCGAGCUCC | 152 |
| miR-136-1 | UGAGCCCUCGGAGGACUCCAUUUGUUUUGAUGAUGGAUUCUUAUGCUCCAUCAUCGUCUCAAAUGAGUCUUCAGAGGGUUCU | 153 |
| miR-136-2 | GAGGACUCCAUUUGUUUUGAUGAUGGAUUCUUAUGCUCCAUCAUCGUCUCAAAUGAGUCUUC | 154 |
| miR-137 | CUUCGGUGACGGGUAUUCUUGGGUGGAUAAUACGGAUUACGUUGUUAUUGCUUAAGAAUACGCGUAGUCGAGG | 155 |
| miR-138-1 | CCCUGGCAUGGUGUGGUGGGGCAGCUGGUGUUGUGAAUCAGGCCGUUGCCAAUCAGAGAACGGCUACUUCACAACACCAGGGCCACACCACUACAGG | 156 |
| miR-138-2 | CGUUGCUGCAGCUGGUGUUGUGAAUCAGGCCGACGAGCAGCGCAUCCUCUUACCCGGCUAUUUCACGACACCAGGGUUGCAUCA | 157 |
| miR-138 | CAGCUGGUGUUGUGAAUCAGGCCGACGAGCAGCGCAUCCUCUUACCCGGCUAUUUCACGACACCAGGGUUG | 158 |
| miR-139 | GUGUAUUCUACAGUGCACGUGUCUCCAGUGUGGCUCGGAGGCUGGAGAGGCGGCCCUGUUGGUAAC | 159 |
| miR-140 | UGUGUCUCUCUCUGUGUCCUGCCAGUGGUUUUACCCUAUGGUAGGUUACGUCAUGCUGUUCUACCACAGGGUAGAACCACGGACAGGAUACCGGGGCACC | 160 |
| miR-140as | UCCUGCCAGUGGUUUUACCCUAUGGUAGGUUACGUCAUGCUGUUCUACCACAGGGUAGAACCACGGACAGGA | 161 |
| miR-140s | CCUGCCAGUGGUUUUACCCUAUGGUAGGUUACGUCAUGCUGUUCUACCACAGGGUAGAACCACGGACAGG | 162 |
| miR-141-1 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | 163 |
| miR-141-2 | GGGUCCAUCUUCCAGUACAGUGUUGGAUGGUCUAAUUGUGAAGCUCCUAACACUGUCUGGUAAAGAUGGCCC | 164 |
| miR-142 | ACCCAUAAAGUAGAAAGCACUACUAACAGCACUGGAGGGUGUAGUGUUUCCUACUUUAUGGAUG | 165 |
| miR-143-1 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | 166 |
| miR-143-2 | CCUGAGGUGCAGUGCUGCAUCUCUGGUCAGUUGGGAGUCUGAGAUGAAGCACUGUAGCUCAGG | 167 |
| miR-144-1 | UGGGGCCCUGGCUGGGAUAUCAUCAUAUACUGUAAGUUUGCGAUGAGACACUACAGUAUAGAUGAUGUACUAGUCCGGGCACCCCC | 168 |
| miR-144-2 | GGCUGGGAUAUCAUCAUAUACUGUAAGUUUGCGAUGAGACACUACAGUAUAGAUGAUGUACUAGUC | 169 |
| miR-145-1 | CACCUUGUCCUCACGGUCCAGUUUUCCCAGGAAUCCCUUAGAUGCUAAGAUGGGGAUUCCUGGAAAUACUGUUCUUGAGGUCAUGGUU | 170 |
| miR-145-2 | CUCACGGUCCAGUUUUCCCAGGAAUCCCUUAGAUGCUAAGAUGGGGAUUCCUGGAAAUACUGUUCUUGAG | 171 |
| miR-146-1 | CCGAUGUGUAUCCUCAGCUUUGAGAACUGAAUUCCAUGGGUUGUGUCAGUGUCAGACCUCUGAAAUUCAGUUCUUCAGCUGGGAUAUCUCUGUCAUCGU | 172 |
| miR-146-2 | AGCUUUGAGAACUGAAUUCCAUGGGUUGUGUCAGUGUCAGACCUCUGAAAUUCAGUUCUUCAGCU | 173 |
| miR-147 | AAUCUAAAGACAACAUUUCUGCACACACACCAGACUAUGGAAGCCAGUGUGUGGAAAUGCUUCUGCUAGAUU | 174 |
| miR-148a (miR-148) | GAGGCAAAGUUCUGAGACACUCCGACUCUGAGUAUGAUAGAAGUCAGUGCACUACAGAACUUUGUCUC | 175 |
| miR-148b | CAAGCACGAUUAGCAUUUGAGGUGAAGUUCUGUUAUACACUCAGGCUGUGGCUCUCUGAAAGUCAGUGCAUCACAGAACUUUGUCUCGAAAGCUUUCUA | 176 |
| miR-148b-small | AAGCACGAUUAGCAUUUGAGGUGAAGUUCUGUUAUACACUCAGGCUGUGGCUCUCUGAAAGUCAGUGCAU | 177 |

TABLE 1a-continued

Human microRNA Precursor Sequences.

| Precursor Name | Sequence (5' To 3')* | SEQ ID NO. |
| --- | --- | --- |
| miR-149-1 | GCCGGCGCCCGAGCUCUGGCUCCGUGUCUUCACUCCCGUGCUUGCGAGGAGGGAGGGAGGGACGGGGGCUGUGCUGGGGCAGCUGGA | 178 |
| miR-149-2 | GCUCUGGCUCCGUGUCUUCACUCCCGUGCUUGUCCGAGGAGGGAGGGAGGGAC | 179 |
| miR-150-1 | CUCCCCAUGGCCCUGUCUCCCAACCCUUGUACCAGUGCUGGGCUCAGACCCUGGUACAGGCCUGGGGGACAGGGACCUGGGGAC | 180 |
| miR-150-2 | CCCUGUCUCCCAACCCUUGUACCAGUGCUGGGCUCAGACCCUGGUACAGGCCUGGGGGACAGGG | 181 |
| miR-151 | UUUCCUGCCCUCGAGGAGCUCACAGUCUAGUAUGUCUCAUCCCUACUAGACUGAAGCUCCUUGAGGACAGG | 182 |
| miR-151-2 | CCUGUCCUCAAGGAGCUUCAGUCUAGUAGGGGAUGAGACAUACUAGACUGUGAGCUCCUCGAGGCAGG | 183 |
| miR-152-1 | UGUCCCCCCGGCCCAGGUUCUGUGAUACACUCCGACUCGGGCUCUGGAGCAGUCAGUGCAUGACAGAACUUGGGCCCGGAAGGACC | 184 |
| miR-152-2 | GGCCCAGGUUCUGUGAUACACUCCGACUCGGGCUCUGGAGCAGUCAGUGCAUGACAGAACUUGGGCCCCGG | 185 |
| miR-153-1-1 | CUCACAGCUGCCAGUGUCAUUUUUGUGAUCUGCAGCUAGUAUUCUCACUCCAGUUGCAUAGUCACAAAAGUGAUCAUUGGCAGGUGUGGC | 186 |
| miR-153-1-2 | UCUCUCUCUCCCUCACAGCUGCCAGUGUCAUUGUCACAAAAGUGAUCAUUGGCAGGUGUGGCUGCAUG | 187 |
| miR-153-2-1 | AGCGGUGGCCAGUGUCAUUUUUGUGAUGUUGCAGCUAGUAAUAUGAGCCCAGUUGCAUAGUCACAAAAGUGAUCAUUGGAAACUGUG | 188 |
| miR-153-2-2 | CAGUGUCAUUUUUGUGAUGUUGCAGCUAGUAAUAUGAGCCCAGUUGCAUAGUCACAAAAGUGAUCAUUG | 189 |
| miR-154-1 | GUGGUACUUGAAGAUAGGUUAUCCGUGUUGCCUUCGCUUUAUUGUGACGAAUCAUACACGGUUGACCUAUUUUUCAGUACCAA | 190 |
| miR-154-2 | GAAGAUAGGUUAUCCGUGUUGCCUUCGCUUUAUUUGUGACGAAUCAUACACGGUUGACCUAUUUUUU | 191 |
| miR-155 | CUGUUAAUGCUAAUCGUGAUAGGGGUUUUUGCCUCCAACUGACUCCUACAUAUUAGCAUUAACAG | 192 |
| miR-156 = miR-157 = overlap miR-141 | CCUAACACUGUCUGGUAAAGAUGGCUCCCGGGUGGGUUCUCUCGGCAGUAACCUUCAGGGAGCCCUGAAGACCAUGGAGGAC | 193 |
| miR-158-small = miR-192 | GCCGAGACCGAGUGCACAGGGCUCUGACCUAUGAAUUGACAGCCAGUGCUCUCGUCUCCCCUCGGCCUCCAAUUCAUAGGUCAGCCUGUAAUGGUUAUGUUCGCCUCAAUGCCAGC | 194 |
| miR-159-1-small | UCCCGCCCCCUGUAACAGCAACUCCAUGUGGAAGUGCCCACUGGUUCCAGUGGGGCUGCUGUUAUCUGGGGCGAGGGCGA | 195 |
| miR-161-small | AAAGCUGGGUUGAGAGGGCGAAAAAGGAUGAGGUGACUGGUCUGGGCUACGCUAUGCUGCGGCGCUCGGG | 196 |
| miR-163-1b-small | CAUUGGCCUCCUAAGCCAGGGAUUGUGGGUUCGAGUCCCACCCGGGGUAAAGAAAGGCCGAAUU | 197 |
| miR-163-3-small | CCUAAGCCAGGGAUUGUGGGUUCGAGUCCCACCUGGGGUAGAGGUGAAAGUUCCUUUUACGGAAUUUUUU | 198 |
| miR-162 | CAAUGUCAGCAGUGCCUUAGCAGCACGUAAAUAUUGGCGUUAAGAUUCUAAAAUUAUCUCCAGUAUUAACUGUGCUGCUGAAGUAAGGUUGACCAUACUCUACAGUUG | 199 |
| miR-175-small = miR-224 | GGGCUUUCAAGUCACUAGUGGUUCCGUUUAGUAGAUGAUUGUGCAUUGUUUCAAAAUGGUGCCCUAGUGACUACAAAGCCC | 200 |
| miR-177-small | ACGCAAGUGUCCUAAGGUGAGCUCAGGGAGCACAGAAACCUCCAGUGGAACAGAAGGGCAAAAGCUCAUU | 201 |
| miR-180-small | CAUGUGUCACUUUCAGGUGGAGUUUCAAGAGUCCCUUCCUGGUUCACCGUCUCCUUUGCUCUUCCACAAC | 202 |
| miR-181a | AGAAGGGCUAUCAGGCCAGCCUUCGAGGACUCCAAGGAACAUUCAACGCUGUCGGUGAGUUUGGGAUUUGAAAAAACCACUGACCGUUGACUGUACCUUGGGGUCCUUA | 203 |
| miR-181b-1 | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | 204 |
| miR-181b-2 | CUGAUGGCUGCACUCAACAUUCAUUGCUGUCGGUGGGUUUGAGUCUGAAUCAACUCACUGAUCAAUGAAUGCAAACUGCGGACCAAACA | 205 |
| miR-181c | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | 206 |
| miR-182-as | GAGCUGCUUGCCUCCCCCGUUUUUGGCAAUGGUAGAACUCACACUGGUGAGGUAACAGGAUCCGGUGGUUCUAGACUUGCCAACUAUGGGGCGAGGACUCAGGCGGCAC | 207 |
| miR-182 | UUUUUGGCAAUGGUAGAACUCACACUGGUGAGGUAACAGGAUCCGGUGGUUCUAGACUUGCCAACUAUGG | 208 |
| miR-183 | CCGCAGAGUGUGACUCCUGUUCUGUGUAUGGCACUGGUAGAAUUCACUGUGAACAGUCUCAGUCAGUGAAUUACCGAAGGGCCAUAAACAGAGCAGAGACAGAUCCACGA | 209 |
| miR-184-1 | CCAGUCACGUCCCCUUAUCACUUUUCCAGCCCAGCUUUGUGACUGUAAGUGUUGGACGGAGAACUGAUAAGGGUAGGUGAUUGA | 210 |
| miR-184-2 | CCUUAUCACUUUUCCAGCCCAGCUUUGUGACUGUAAGUGUUUGGACGGAGAACUGAUAAGGGUAGG | 211 |
| miR-185-1 | AGGGGGCGAGGGAUUGGAGAGAAAGGCAGUUCCUGAUGGUCCCCUCCCCAGGGGCUGGCUUUCCUCUGGUCCUUCCCUCCCA | 212 |

TABLE 1a-continued

Human microRNA Precursor Sequences.

| Precursor Name | Sequence (5' To 3')* | SEQ ID NO. |
|---|---|---|
| miR-185-2 | AGGGAUUGGAGAGAAAGGCAGUUCCUGAUGGU CCCCUCCCCAGGGGCUGGCUUUCCUCUGGUCC UU | 213 |
| miR-186-1 | UGCUUGUAACUUUCCAAAGAAUUCUCCUUUUG GGCUUUCUGGGUUUUAUUUUAAGCCCAAAGGUG AAUUUUUUGGGAAGUUUGAGCU | 214 |
| miR-186-2 | ACUUUCCAAAGAAUUCUCCUUUUGGGCUUUCU GGUUUUAUUUUAAGCCCAAAGGUGAAUUUUUU GGGAAGU | 215 |
| miR-187 | GGUCGGGCUCACCAUGACACAGUGUGAGACUC GGGCUACAACACAGGACCCCGGGGCGCUGCUCU GACCCCUCGUGUCUUGUGUUGCAGCCGGAGGG ACGCAGGUCCGCA | 216 |
| miR-188-1 | UGCUCCCUCUCUCACAUCCCUUGCAUGGUGGA GGGUGAGCUUUCUGAAAACCCCUCCCACAUGC AGGGUUUGCAGGAUGGCGAGCC | 217 |
| miR-188-2 | UCUCACAUCCCUUGCAUGGUGGAGGGUGAGCU UUCUGAAAACCCCUCCCACAUGCAGGGUUUGC AGGA | 218 |
| miR-189-1 | CUGUCGAUGGACCCGCCCUCCGGUGCCUACU GAGCUGAUAUCAGUUCUCAUUUUACACACUGG CUCAGUUCAGCAGGAACAGGAGUCGAGCCCUU GAGCAA | 219 |
| miR-189-2 | CUCCGGUGCCUACUGAGCUGAUAUCAGUUCUC AUUUUACACACUGGCUCAGUUCAGCAGGAACA GGAG | 220 |
| miR-190-1 | UGCAGGCCUCUGUGUGAUAUGUUUGAUAUAUU AGGUUGUUAUUUAAUCCAACUAUAUAUCAAAC AUAUUCCUACAGUGUCUUGCC | 221 |
| miR-190-2 | CUGUGUGAUAUGUUUGAUAUAUUAGGUUGUUA UUUAAUCCAACUAUAUAUCAAACAUAUUCCUA CAG | 222 |
| miR-191-1 | CGGCUGGACAGCGGGCAACGGAAUCCCAAAAG CAGCUGUUGUCUCCAGAGCAUUCCAGCUGCGC UUGGAUUUCGUCCCCUGCUCUCCUGCC | 223 |
| miR-191-2 | AGCGGGCAACGGAAUCCCAAAAGCAGCUGUUG UCUCCAGAGCAUUCCAGCUGCGCUUGGAUUUC GUCCCCUGCU | 224 |
| miR-192-2/3 | CCGAGACCGAGUGCACAGGGCUCUGACCUAUG AAUUGACAGCCAGUGCUCUCGUCUCCCCUCUG GCUGCCAAUUCCAUAGGUCACAGGUAUGUUCG CCUCAAUGCCAG | 225 |
| miR-192 | GCCGAGACCGAGUGCACAGGGCUCUGACCUAU GAAUUGACAGCCAGUGCUCUCGUCUCCCCUCU GGCUGCCAAUUCCAUAGGUCACAGGUAUGUUC GCCUCAAUGCCAGC | 226 |
| miR-193-1 | CGAGGAUGGGAGCUGAGGGCUGGGUCUUUGCG GGCGAGAUGAGGGUGUCGGAUCAACGGCCUA CAAAGUCCCAGUUCUCGGCCCCCG | 227 |
| miR-193-2 | GCUGGGUCUUUGCGGGCGAGAUGAGGGUGUCG GAUCAACGGCCUACAAAGUCCCAGU | 228 |
| miR-194-1 | AUGGUGUUAUCAAGUGUAACAGCAACUCCAUG UGGACUGUGUACCAAUUUCCAGUGGAGAUGCU GUUACUUUUGAUGGUUACCAA | 229 |
| miR-194-2 | GUGUAACAGCAACUCCAUGUGGACUGUGUACC AAUUUCCAGUGGAGAUGCUGUUACUUUUGAU | 230 |
| miR-195-1 | AGCUUCCCUGGCUCUAGCAGCACAGAAAUAUU GGCACAGGGAAGCGAGUCUGCCAAUAUUGGCU GUGCUGCUCCAGGCAGGGUGGUG | 231 |
| miR-195-2 | UAGCAGCACAGAAAUAUUGGCACAGGGAAGCG AGUCUGCCAAUAUUGGCUGUGCUGCU | 232 |
| miR-196-1 | CUAGAGCUUGAAUUGGAACUGCUGAGUGAAUU AGGUAGUUUCAUGUUGUUGGGCCUGGGUUUCU GAACACAACAACAUUAAACCACCCGAUUCACG GCAGUUACUGCUCC | 233 |
| miR-196a-1 | GUGAAUUAGGUAGUUUCAUGUUGUUGGGCCUG GGUUUCUGAACACAACAACAUUAAACCACCCG AUUCAC | 234 |
| miR-196a-2 (miR-196-2) | UGCUCGCUCAGCUGAUCUGUGGCUUAGGUAGU UCAUGUUGUGGGAUUGAGUUUGAACUCGG CAACAAGAAACUGCCUGAGUUACAUCAGUCGG UUUCGUCGAGGGC | 235 |
| miR-196 | GUGAAUUAGGUAGUUUCAUGUUGUUGGGCCUG GGUUUCUGAACACAACAACAUUAAACCACCCG AUUCAC | 236 |
| miR-196b | ACUGGUCGGUGAUUUAGGUAGUUUCCUGUUGU UGGGAUCCACCUUUCUCUCGACAGCACGACAC UGCCUUCAUUACUUCAGUUG | 237 |
| miR-197 | GGCUGUGCCGGGUAGAGAGGGCAGUGGGAGGU AAGAGCUCUUCACCCUUCACCACCUUCUCCAC CCAGCAUGGCC | 238 |
| miR-197-2 | GUGCAUGUGUAUGUAUGUGUGCAUGUGCAUGU GUAUGUGUAUGAGUGCAUGCGUGUGUGC | 239 |
| miR-198 | UCAUUGGUCCAGAGGGGAGAUAGGUUCCUGUG AUUUUUCCUUCUUCUCUAUAGAAUAAAUGA | 240 |
| miR-199a-1 | GCCAACCCAGUGUUCAGACUACCUGUUCAGGA GGCUCUCAAUGUGUACAGUAGUCUGCACAUUG GUUAGGC | 241 |
| miR-199a-2 | AGGAAGCUUCUGGAGAUCCUGCUCCGUCGCCC CAGUGUUCAGACUACCUGUUCAGGACAAUGCC GUUGUACAGUAGUCUGCACAUUGGUUAGACUG GGCAAGGGAGAGCA | 242 |
| miR-199b | CCAGAGGACACCUCCACUCCGUCUACCCAGUG UUUAGACUAUCUGUUCAGGACUCCCAAAUUGU ACAGUAGUCUGCACAUUGGUUAGGCUGGGCUG GGUUAGACCCUCGG | 243 |
| miR-199s | GCCAACCCAGUGUUCAGACUACCUGUUCAGGA GGCUCUCAAUGUGUACAGUAGUCUGCACAUUG GUUAGGC | 244 |
| miR-200a | GCCGUGGCCAUCUUACUGGGCAGCAUUGGAUG GAGUCAGGUCUCUAAUACUGCCUGGUAAUGAU GACGGC | 245 |
| miR-200b | CCAGCUCGGGCAGCCGUGGCCAUCUUACUGGG CAGCAUUGGAUGGAGUCAGGUCUCUAAUACUG CCUGGUAAUGAUGACGGCGGAGCCCUGCACG | 246 |
| miR-200c | CCCUCGUCUUACCCAGCAGUGUUUGGGUGCGG UUGGGAGUCUCUAAUACUGCCGGGUAAUGAUG GAGG | 247 |
| miR-202 | GUUCCUUUUUCCUAUGCAUAUACUUCUUUGAG GAUCUGGCCUAAAGAGGUAUAGGGCAUGGGAA GAUGGAGC | 248 |

TABLE 1a-continued

Human microRNA Precursor Sequences.

| Precursor Name | Sequence (5' To 3')* | SEQ ID NO. |
|---|---|---|
| miR-203 | GUGUUUGGGACUCGCGCGCUGGGUCCAGUGGU UCUUAACAGUUCAACAGUUCUGUAGCGCAAUU GUGAAAUGUUUAGGACCACUAGACCCGGCGGG CGCGGCGACAGCGA | 249 |
| miR-204 | GGCUACAGUCUUUCUUCAUGUGACUCGUGGAC UUCCCUUUGUCAUCCUAUGCCUGAGAAUAUAU GAAGGAGGCUGGGAAGGCAAAGGGACGUUCAA UUGUCAUCACUGGC | 250 |
| miR-205 | AAAGAUCCUCAGACAAUCCAUGUGCUUCUCUU GUCCUUCAUUCCACCGGAGUCUGUCUCAUACC CAACCAGAUUUCAGUGGAGUGAAGUUCAGGAG GCAUGGAGCUGACA | 251 |
| miR-206-1 | UGCUUCCCGAGGCCACAUGCUUCUUUAUAUCC CCAUAUGGAUUACUUUGCUAUGGAAUGUAAGG AAGUGUGUGGUUUCGGCAAGUG | 252 |
| miR-206-2 | AGGCCACAUGCUUCUUUAUAUCCCCAUAUGGA UUACUUUGCUAUGGAAUGUAAGGAAGUGUGUG GUUUU | 253 |
| miR-208 | UGACGGGCGAGCUUUUGGCCCGGGUUAUACCU GAUGCUCACGAUAAGACGAGCAAAAAGCUUG UUGGUCA | 254 |
| miR-210 | ACCCGGCAGUGCCUCCAGGCGCAGGGCAGCCC CUGCCCACCGCACACUGCGCUGCCCCAGACCC ACUGUGCGUGUGACAGCGGCUGAUCUGUGCCU GGGCAGCGCGACCC | 255 |
| miR-211 | UCACCUGGCCAUGUGACUUGUGGGCUUCCCUU UGUCAUCCUUCGCCUAGGGCUCUGAGCAGGGC AGGGACAGCAAAGGGGUGCUCAGUUGUCACUU CCCACAGCACGGAG | 256 |
| miR-212 | CGGGGCACCCCGCCCGGACAGCGCGCCGGCAC CUUGGCUCUAGACUGCUUACUGCCCGGGCCGC CCUCAGUAACAGUCUCCAGUCACGGCCACCGA CGCCUGGCCCCGCC | 257 |
| miR-213-2 | CCUGUGCAGAGAUUAUUUUUUAAAAGGUCACA AUCAACAUUCAUUGCUGUCGGUGGGUUGAACU GUGUGGACAAGCUCACUGAACAAUGAAUGCAA CUGUGGCCCCGCUU | 258 |
| miR-213 | GAGUUUUGAGGUUGCUUCAGUGAACAUUCAAC GCUGUCGGUGAGUUUGGAAUUAAAAUCAAAAC CAUCGACCGUUGAUUGUACCCUAUGGCUAACC AUCAUCUACUCC | 259 |
| miR-214 | GGCCUGGCUGGACAGAGUUGUCAUGUGUCUGC CUGUCUACACUUGCUGUGCAGAACAUCCGCUC ACCUGUACAGCAGGCACAGACAGGCAGUCACA UGACAACCCAGCCU | 260 |
| miR-215 | AUCAUUCAGAAAUGGUAUACAGGAAAAUGACC UAUGAAUUGACAGACAAUAUAGCUGAGUUUGU CUGUCAUUUCUUUAGGCCAAUAUUCUGUAUGA CUGUGCUACUUCAA | 261 |
| miR-216 | GAUGGCUGUGAGUUGGCUUAAUCUCAGCUGGC AACUGUGAGAUGUUCAUACAAUCCCUCACAGU GGUCUCUGGGAUUAUGCUAAACAGAGCAAUUU CCUAGCCCUCACGA | 262 |
| miR-217 | AGUAUAAUUAUUACAUAGUUUUUGAUGUCGCA GAUACUGCAUCAGGAACUGAUUGGAUAAGAAU CAGUCACCAUCAGUUCCUAAUGCAUUGCCUUC AGCAUCUAAACAAG | 263 |
| miR-218-1 | GUGAUAAUGUAGCGAGAUUUUCUGUUGUGCUU GAUCUAACCAUGUGGUUGCGAGGUAUGAGUAA AACAUGGUUCCGUCAAGCACCAUGGAACGUCA CGCAGCUUUCUACA | 264 |
| miR-218-2 | GACCAGUCGCUGCGGGGCUUUCCUUUGUGCUU GAUCUAACCAUGUGGUGGAACGAUGGAAACGG AACAUGGUUCUGUCAAGCACCGCGGAAAGCAC CGUGCUCUCCUGCA | 265 |
| miR-219 | CCGCCCCGGGCCGCGGCUCCUGAUUGUCCAAA CGCAAUUCUCGAGUCUAUGGCUCCGGCCGAGA GUUGAGUCUGGACGUCCCGAGCCGCCGCCCCC AAACCUCGAGCGGG | 266 |
| miR-219-1 | CCGCCCCGGGCCGCGGCUCCUGAUUGUCCAAA CGCAAUUCUCGAGUCUAUGGCUCCGGCCGAGA GUUGAGUCUGGACGUCCCGAGCCGCCGCCCCC AAACCUCGAGCGGG | 267 |
| miR-219-2 | ACUCAGGGGCUUCGCCACUGAUUGUCCAAACG CAAUUCUUGUACGAGUCUGCGGCCAACCGAGA AUUGUGGCUGGACAUCUGUGGCUGAGCUCCGG G | 268 |
| miR-220 | GACAGUGUGGGCAUUGUAGGGCUCCACACCGUA UCUGACACUUUGGGCGAGGGCACCAUGCUGAA GGUGUUCAUGAUGCGGUCUGGGAACUCCUCAC GGAUCUUACUGAUG | 269 |
| miR-221 | UGAACAUCCAGGUCGGGGCAUGAACCUGGCA UACAAUGUAGAUUUCUGUGUUCGUUAGGCAAC AGCUACAUUGUCUGCUGGGUUUCAGGCUACCU GGAAACAUGUUCUC | 270 |
| miR-222 | GCUGCUGGAAGGUGUAGGUACCCUCAAUGGCU CAGUAGCCAGUGUAGAUCCUGUCUUUCGUAAU CAGCAGCUACAUCUGGCUACUGGGUCUCUGAU GGCAUCUUCUAGCU | 271 |
| miR-223 | CCUGGCCUCCUGCAGUGCCACGCUCCGUGUAU UUGACAAGCUGAGUUGGACACUCCAUGUGGUA GAGUGUCAGUUUGUCAAAUACCCCAAGUGCGG CACAUGCUUACCAG | 272 |
| miR-224 | GGGCUUUCAAGUCACUAGUGGUUCCGUUUAGU AGAUGAUUGUGCAUUGUUUCAAAAUGGUGCCC UAGUGACUACAAAGCCC | 273 |
| miR-294-1 (chr16) | CAAUCUUCCUUUAUCAUGGUAUUGAUUUUUCA GUGCUUCCCUUUUGUGUGAGAGAAGAUA | 274 |
| miR-296 | AGGACCCUUCCAGAGGGCCCCCCCUCAAUCCU GUUGUGCCUAAUUCAGAGGGUUGGGUGGAGGC UCUCCUGAAGGGCUCU | 275 |
| miR-299 | AAGAAAUGGUUUACCGUCCCACAUACAUUUUG AAUAUGUAUGUGGGAUGGUAAACCGCUUCUU | 276 |
| miR-301 | ACUGCUAACGAAUGCUCUGACUUUAUUGCACU ACUGUACUUUACAGCUAGCAGUGCAAUAGUAU UGUCAAAGCAUCUGAAAGCAGG | 277 |
| miR-302a | CCACCACUUAAACGUGGAUGUACUUGCUUUGA AACUAAAGAAGUAAGUGCUUCCAUGUUUUGGU GAUGG | 278 |
| miR-302b | GCUCCCUUCAACUUUAACAUGGAAGUGCUUUC UGUGACUUUAAAAGUAAGUGCUUCCAUGUUUU AGUAGGAGU | 279 |
| miR-302c | CCUUUGCUUUAACAUGGGGGUACCUGCUGUGU GAAACAAAAGUAAGUGCUUCCAUGUUUCAGUG GAGG | 280 |

TABLE 1a-continued

Human microRNA Precursor Sequences.

| Precursor Name | Sequence (5' To 3')* | SEQ ID NO. |
|---|---|---|
| miR-302d | CCUCUACUUUAACAUGGAGGCACUUGCUGUGA CAUGACAAAAAU<u>AAGUGCUUCCAUGUUUGAGU GUGG</u> | 281 |
| miR-320 | GCUUCGCUCCCCUCCGCCUUCUCUUCCCGGUU CUUCCCGGAGUCGGG<u>AAAAGCUGGGUUGAGAG GGCGAA</u>AAAGGAUGAGGU | 282 |
| miR-321 | UUGGCCUCC<u>UAAGCCAGGGAUUGUGGGUUCGA GUCCC</u>ACCCGGGGUAAAGAAAGGCCGA | 283 |
| miR-323 | UUGGUACUUGGAGAGAGGUGGUCCGUGGCGCG UUCGCUUUAUUUAUGGCGCACAUUACACGGUC GACCUCUUUGCAGUAUCUAAUC | 284 |
| miR-324 | CUGACUAUGCCUCCC<u>CGCAUCCCCUAGGGCAU UGGUGUAAAGCUGGAGACCCACUGCCCCAGGU GCUGCUGG</u>GGGUUGUAGUC | 285 |
| miR-325 | AUACAGUGCUUGGUUCCUAGUAGGUGUCCAGU AAGUGUUUGUGACAUAAUUUGUUUAUUGAGGA CCUCCUAUCAAUCAAGCACUGUGCUAGGCUCU GG | 286 |
| miR-326 | CUCAUCUGUCUGUUGGGCUGGAGGCAGGGCCU UUGUGAAGGCGGGUGGUGCUCAGAUCGCCUCU GGGCCCUUCCUCCAGCCCCGAGGCGGAUUCA | 287 |
| miR-328 | UGGAGUGGGGGGCAGGAGGGGCUCAGGGAGA AAGUGCAUACAGCCC<u>CUGGCCCUCUCUGCCCU UCCGU</u>CCCUG | 288 |
| miR-330 | CUUUGGCGAUCACUGCCUCUCUGGGCCUGUGU CUUAGGCUCUGCAAGAUCAACCGA<u>GCAAAGCA CACGGCCUGCAGAGAGGCAGCGCUCUGCCC</u> | 289 |
| miR-331 | GAGUUUGGUUUUGUUUGGGUUUGUUCUAGGUA UGGUCCCAGGGAUCCCAGAUCAAACCAGG<u>CCC CUGGGCCUAUCCUAGAACCAACCUAAGCUC</u> | 290 |
| miR-335 | UGUUUUGAGCGGGGG<u>UCAAGAGCAAUAACGAA AAAUGUUUGUCAUAAACCGUUUUUCAUUAUUG</u> CUCCUGACCUCCUCUCAUUUGCUAUAUUCA | 291 |
| miR-337 | GUAGUCAGUAGUUGGGGGUGGGAACGGCUUC AUAGAGGAGUUGAUGCACAGUUA<u>UCCAGCUCC UAUAUGAUGCCUUUC</u>UUCAUCCCCUUCAA | 292 |
| miR-338 | UCUCCAACAAUAUCCUGGUGCUGAGUGAUGAC UCAGGCGAC<u>UCCAGCAUCAGUGAUUUUGUUGA AGA</u> | 293 |
| miR-339 | CGGGGCGGCCGCUC<u>UCCCUGUCCUCCAGGAGC UCA</u>CGUGUGCCUGCCUGUGAGCGCCUCGACGA CAGAGCCGGCGCCUGCCCCAGUGUCUGCGC | 294 |
| miR-340 | UUGUACCGGUGUGAUUAUAAAGCAAUGAGAC UGAUUGUCAUAUGUCGUUUGUGGGA<u>UCCGUCU CAGUUACUUUAUAGCCAUACCUGGUAUCUUA</u> | 295 |
| miR-342 | GAAACUGGGCUCAAGGUGAGGGGUGCUAUCUG UGAUUGAGGGACAUGGUUAAUGGAAUUG<u>UCUC ACACAGAAAUCGCACCCGUC</u>ACCUUGGCCUAC UUA | 296 |
| miR-345 | ACCCAAACCCUAGGUC<u>UGCUGACUCCUAGUCC AGGGC</u>UCGUGAUGGCUGGUGGGCCCUGAACGA GGGGUCUGGAGGCCUGGGUUUGAAUAUCGACA GC | 297 |
| miR-346 | GU<u>CUGUCUGCCCGCAUGCCUGCCUCU</u>CUGUUG CUCUGAAGGAGGCAGGGGCUGGGCCUGCAGCU GCCUGGGCAGAGCGGCUCCUGC | 298 |

TABLE 1a-continued

Human microRNA Precursor Sequences.

| Precursor Name | Sequence (5' To 3')* | SEQ ID NO. |
|---|---|---|
| miR-367 | CCAUUACUGUUGCUAAUAUGCAACUCUGUUGA AUAUAAAUUGGAAUUGCACUUUAGCAAUGGUG AUGG | 299 |
| miR-368 | AAAAGGUGGAUAUUCCUUCUAUGUUUAUGUUA UUUAUGGUUAA<u>ACAUAGAGGAAAUUCCACGUU UU</u> | 300 |
| miR-369 | UUGAAGGGAGAUCGACCGUGUUAUAUUCGCUU UAUUGACUUC<u>GAAUAAUACAUGGUUGAUCUUU UCUCAG</u> | 301 |
| miR-370 | AGACAGAGAAGCCAGGUCACGUCUCUGCAGUU ACACAGCUCACGAGU<u>GCCUGCUGGGGUGGAAC CUGG</u>UCUGUCU | 302 |
| miR-371 | GUGGCACUCAAACUGUGGGGGCACUUUCUGCU CUCUGGUGAAA<u>GUGCCGCCAUCUUUUGAGUGU UAC</u> | 303 |
| miR-372 | GUGGGCCUCAAAUGUGGAGCACUAUUCUGAUG UCCAAGUGGA<u>AAGUGCUGCGACAUUUGAGCGU CAC</u> | 304 |
| miR-373 | GGGAUACUCAAAAUGGGGGCGCUUUCCUUUUU GUCUGUACUGGGAAGUGCUUCGAUUUUGGGGU GUCCC | 305 |
| miR-374 | UACAUCGGCC<u>AUUAUAAUACAACCUGAUAAGU GUUAUAGCACUUAUCAGAUUGUAUUGUAAUUG UCUGUGUA</u> | 306 |
| miR-hes1 | AUGGAGCUGCUCACCCUGUGGGCCUCAAAUGU GGAGGAACUAUUCUGAUGUCCAAGUGGAAAGU GCUGCGACAUUUGAGCGUGACCGGUGACGCCC AUAUCA | 307 |
| miR-hes2 | GCAUCCCCUCAGCCUGUGGCACUCAAACUGUG GGGGCACUUUCUGCUCUCUGGUGAAAGUGCCG CCAUCUUUUGAGUGUUACCGCUUGAGAAGACU CAACC | 308 |
| miR-hes3 | CGAGGAGCUCAUACUGGGAUACUCAAAAUGGG GGCGCUUUCCUUUUUGUCUGUUACUGGGAAGU GCUUCGAUUUUGGGGUGUCCCUGUUUGAGUAG GGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | ugagguaguagguuguauaguu | 310 | let-7a-1; let-7a-2; let-7a-3; let-7a-4 |
| let-7b | ugagguaguagguugugugguu | 311 | let-7b |
| let-7c | ugagguaguagguuguaugguu | 312 | let-7c |
| let-7d | agagguaguagguugcauagu | 313 | let-7d; let-7d-v1 |
| let-7e | ugagguaggagguuguauagu | 314 | let-7e |
| let-7f | ugagguaguagauuguauaguu | 315 | let-7f-1; let-7f-2-1; let-7f-2-2 |
| let-7g | ugagguaguaguuuguacagu | 316 | let-7g |
| let-7i | ugagguaguaguuugugcu | 317 | let-7i |
| miR-1 | uggaauguaaagaaguaugua | 318 | miR-1b; miR-1b-1; miR-1b-2 |
| miR-7 | uggaagacuagugauuuuguu | 319 | miR-7-1; miR-7-1a; miR-7-2; miR-7-3 |
| miR-9 | ucuuugguuaucuagcuguauga | 320 | miR-9-1; miR-9-2; miR-9-3 |
| miR-9* | uaaagcuagauaaccgaaagu | 321 | miR-9-1; miR-9-2; miR-9-3 |
| miR-10a | uacccuguagauccgaauuugug | 322 | miR-10a |
| miR-10b | uacccuguagaaccgaauuugu | 323 | miR-10b |
| miR-15a | uagcagcacauaaugguuugug | 324 | miR-15a; miR-15a-2 |
| miR-15b | uagcagcacaucaugguuuaca | 325 | miR-15b |
| miR-16 | uagcagcacguaaauauuggcg | 326 | miR-16-1; miR-16-2; miR-16-13 |
| miR-17-5p | caaagugcuuacagugcagguagu | 327 | miR-17 |
| miR-17-3p | acugcagugaaggcacuugu | 328 | miR-17 |
| miR-18 | uaaggugcaucuagugcagaua | 329 | miR-18; miR-18-13 |
| miR-19a | ugugcaaaucuaugcaaaacuga | 330 | miR-19a; miR-19a-13 |
| miR-19b | ugugcaaauccaugcaaaacuga | 331 | miR-19b-1; miR-19b-2 |
| miR-20 | uaaagugcuuauagugcaggua | 332 | miR-20 (miR-20a) |
| miR-21 | uagcuuaucagacugauguuga | 333 | miR-21; miR-21-17 |
| miR-22 | aagcugccaguugaagaacugu | 334 | miR-22 |
| miR-23a | aucacauugccagggauuucc | 335 | miR-23a |
| miR-23b | aucacauugccagggauuaccac | 336 | miR-23b |
| miR-24 | uggcucaguucagcaggaacag | 337 | miR-24-1; miR-24-2; miR-24-19; miR-24-9 |
| miR-25 | cauugcacuugucucggucuga | 338 | miR-25 |
| miR-26a | uucaaguaauccaggauaggcu | 339 | miR-26a; miR-26a-1; miR-26a-2 |
| miR-26b | uucaaguaauucaggauaggu | 340 | miR-26b |
| miR-27a | uucacaguggcuaaguuccgcc | 341 | miR-27a |
| miR-27b | uucacaguggcuaaguucug | 342 | miR-27b-1; miR-27b-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-28 | aaggagcucacagucuauugag | 343 | miR-28 |
| miR-29a | cuagcaccaucugaaaucgguu | 344 | miR-29a-2; miR-29a |
| miR-29b | uagcaccauuugaaaucagu | 345 | miR-29b-1; miR-29b-2 |
| miR-29c | uagcaccauuugaaaucgguua | 346 | miR-29c |
| miR-30a-5p | uguaaacauccucgacuggaagc | 347 | miR-30a |
| miR-30a-3p | cuuucagucggauguuugcagc | 348 | miR-30a |
| miR-30b | uguaaacauccuacacucagc | 349 | miR-30b-1; miR-30b-2 |
| miR-30c | uguaaacauccuacacucucagc | 350 | miR-30c |
| miR-30d | uguaaacauccccgacuggaag | 351 | miR-30d |
| miR-30e | uguaaacauccuugacugga | 352 | miR-30e |
| miR-31 | ggcaagaugcuggcauagcug | 353 | miR-31 |
| miR-32 | uauugcacauuacuaaguugc | 354 | miR-32 |
| miR-33 | gugcauuguaguugcauug | 355 | miR-33; miR-33b |
| miR-34a | uggcagugucuuagcugguugu | 356 | miR-34a |
| miR-34b | aggcagugucauuagcugauug | 357 | miR-34b |
| miR-34c | aggcaguguaguuagcugauug | 358 | miR-34c |
| miR-92 | uauugcacuugucccggccugu | 359 | miR-92-2; miR-92-1 |
| miR-93 | aaagugcuguucgugcagguag | 360 | miR-93-1; miR-93-2 |
| miR-95 | uucaacggguauuuauugagca | 361 | miR-95 |
| miR-96 | uuuggcacuagcacauuuuugc | 362 | miR-96 |
| miR-98 | ugagguaguaaguuguauuguu | 363 | miR-98 |
| miR-99a | aacccguagauccgaucuugug | 364 | miR-99a |
| miR-99b | cacccguagaaccgaccuugcg | 365 | miR-99b |
| miR-100 | uacaguacugugauaacugaag | 366 | miR-100 |
| miR-101 | uacaguacugugauaacugaag | 367 | miR-101-1; miR-101-2 |
| miR-103 | agcagcauuguacagggcuauga | 368 | miR-103-1 |
| miR-105 | ucaaaugcucagacuccugu | 369 | miR-105 |
| miR-106-a | aaaagugcuuacagugcagguagc | 370 | miR-106-a |
| miR-106-b | uaaagugcugacagugcagau | 371 | miR-106-b |
| miR-107 | agcagcauuguacagggcuauca | 372 | mir-107 |
| miR-122a | uggagugugacaauggguguuugu | 373 | miR-122a-1; miR-122a-2 |
| miR-124a | uuaaggcacgcggugaaugcca | 374 | miR-124a-1; miR-124a-2; miR-124a-3 |
| miR-125a | ucccugagacccuuuaaccugug | 375 | miR-125a-1; miR-125a-2 |
| miR-125b | ucccugagacccuaacuuguga | 376 | miR-125b-1; miR-125b-2 |
| miR-126* | cauuauuacuuuuggguacgcg | 377 | miR-126-1; miR-126-2 |
| miR-126 | ucguaccgugaguaauaaugc | 378 | miR-126-1; miR-126-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-127 | ucggauccgucugagcuuggcu | 379 | miR-127-1; miR-127-2 |
| miR-128a | ucacagugaaccggucucuuuu | 380 | miR-128; miR-128a |
| miR-128b | ucacagugaaccggucucuuuc | 381 | miR-128b |
| miR-129 | cuuuuugcggucugggcuugc | 382 | miR-129-1; miR-129-2 |
| miR-130a | cagugcaauguuaaaagggc | 383 | miR-130a |
| miR-130b | cagugcaaugaugaaagggcau | 384 | miR-130b |
| miR-132 | uaacagucuacagccauggucg | 385 | miR-132-1 |
| miR-133a | uugguccccuucaaccagcugu | 386 | miR-133a-1; miR-133a-2 |
| miR-133b | uugguccccuucaaccagcua | 387 | miR-133b |
| miR-134 | ugugacugguugaccagaggg | 388 | miR-134-1; miR-134-2 |
| miR-135a | uauggcuuuuuauuccuauguga | 389 | miR-135a; miR-135a-2 (miR-135-2) |
| miR-135b | uauggcuuuucauuccuaugug | 390 | miR-135b |
| miR-136 | acuccauuuguuuugaugaugga | 391 | miR-136-1; miR-136-2 |
| miR-137 | uauugcuuaagaauacgcguag | 392 | miR-137 |
| miR-138 | agcugguguugugaauc | 393 | miR-138-1; miR-138-2 |
| miR-139 | ucuacagugcacgugucu | 394 | miR-139 |
| miR-140 | aggguuuuacccuaugguag | 395 | miR-140; miR-140as; miR-140s |
| miR-141 | aacacugucugguaaagaugg | 396 | miR-141-1; miR-141-2 |
| miR-142-3p | uguaguguuuccuacuuuaugga | 397 | miR-142 |
| miR-142-5p | cauaaaguagaaagcacuac | 398 | miR-142 |
| miR-143 | ugagaugaagcacuguagcuca | 399 | miR-143-1 |
| miR-144 | uacaguauagaugauguacuag | 400 | miR-144-1; miR-144-2 |
| miR-145 | guccaguuuucccaggaaucccuu | 401 | miR-145-1; miR-145-2 |
| miR-146 | ugagaacugaauuccaugdgguu | 402 | miR-146-1; miR-146-2 |
| miR-147 | guguguggaaaugcuucugc | 403 | miR-147 |
| miR-148a | ucagugcacuacagaacuuugu | 404 | miR-148a (miR-148) |
| miR-148b | ucagugcaucacagaacuuugu | 405 | miR-148b |
| miR-149 | ucuggcuccgugucuucacucc | 406 | miR-149 |
| miR-150 | ucucccaacccuuguaccagug | 407 | miR-150-1; miR-150-2 |
| miR-151 | acuagacugaagcuccuugagg | 408 | miR-151 |
| miR-152 | ucagugcaugacagaacuugg | 409 | miR-152-1; miR-152-2 |
| miR-153 | uugcauagucacaaaaguga | 410 | miR-153-1-1; miR-153-1-2; miR-153-2-1; miR-153-2-2 |
| miR-154 | uagguuauccguguugccuucg | 411 | miR-154-1; miR-154-2 |
| miR-154* | aaucauacacgguugaccuauu | 412 | miR-154-1; miR-154-2 |
| miR-155 | uuaaugcuaaucugugauagggg | 413 | miR-155 |
| miR-181a | aacauucaacgcugucggugagu | 414 | miR-181a |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-181b | aacauucauugcugucggugggu | 415 | miR-181b-1; miR-181b-2 |
| miR-181c | aacauucaaccugucggugagu | 416 | miR-181c |
| miR-182 | uuuggcaaugguagaacucaca | 417 | miR-182; miR-182as |
| miR-182* | agguucuagacuugccaacua | 418 | miR-182; miR-182as |
| miR-183 | uauggcacugguagaauucacug | 419 | miR-183 |
| miR-184 | uggacggagaacugauaagggu | 420 | miR-184-1; miR-184-2 |
| miR-185 | uggagagaaaggcaguuc | 421 | miR-185-1; miR-185-2 |
| miR-186 | caaagaauucuccuuuugggcuu | 422 | miR-186-1; miR-186-2 |
| miR-187 | ucgugucuuguguugcagccg | 423 | miR-187 |
| miR-188 | caucccuugcauggugagggu | 424 | miR-188 |
| miR-189 | gugccuacugagcugauaucagu | 425 | miR-189-1; miR-189-2 |
| miR-190 | ugauauguuugauauauuaggu | 426 | miR-190-1; miR-190-2 |
| miR-191 | caacggaaucccaaaagcagcu | 427 | miR-191-1; miR-191-2 |
| miR-192 | cugaccuaugaauugacagcc | 428 | miR-192 |
| miR-193 | aacuggccuacaaagucccag | 429 | miR-193-1; miR-193-2 |
| miR-194 | uguaacagcaacuccaugugga | 430 | miR-194-1; miR-194-2 |
| miR-195 | uagcagcacagaaauauuggc | 431 | miR-195-1; miR-195-2 |
| miR-196a | uagguaguuucauguuguugg | 432 | miR-196a; miR-196a-2 (miR196-2) |
| miR-196b | uagguaguuuccuguuguugg | 433 | miR-196b |
| miR-197 | uucaccaccuucuccacccagc | 434 | miR-197 |
| miR-198 | gguccagaggggagauagg | 435 | miR-198 |
| miR-199a | cccaguguucagacuaccuguuc | 436 | miR-199a-1; miR-199a-2 |
| miR-199a* | uacaguagucugcacauugguu | 437 | miR-199a-1; miR-199a-2; miR-199s; miR-199b |
| miR-199b | cccaguguuuagacuaucuguuc | 438 | miR-199b |
| miR-200a | uaacacugucugguaacgaugu | 439 | miR-200a |
| miR-200b | cucuaauacugccugguaaugaug | 440 | miR-200b |
| miR-200c | aauacugccggguaaugaugga | 441 | miR-200c |
| miR-202 | agagguauagggcaugggaaga | 442 | miR-202 |
| miR-203 | gugaaauguuuaggaccacuag | 443 | miR-203 |
| miR-204 | uucccuuugucauccuaugccu | 444 | miR-204 |
| miR-205 | uccuucauuccaccggagucug | 445 | miR-205 |
| miR-206 | uggaauguaaggaagugugugg | 446 | miR-206-1; miR-206-2 |
| miR-208 | auaagacgagcaaaaagcuugu | 447 | miR-208 |
| miR-210 | cugugcgugugacagcggcug | 448 | miR-210 |
| miR-211 | uucccuuugucauccuucgccu | 449 | miR-211 |
| miR-212 | uaacagucuccagucacggcc | 450 | miR-212 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-213 | accaucgaccguugauuguacc | 451 | miR-213 |
| miR-214 | acagcaggcacagacaggcag | 452 | miR-214 |
| miR-215 | augaccaugaauugacagac | 453 | miR-215 |
| miR-216 | uaaucucagcuggcaacugug | 454 | miR-216 |
| miR-217 | uacugcaucaggaacugauuggau | 455 | miR-217 |
| miR-218 | uugugcuugaucuaaccaugu | 456 | miR-218-1; miR-218-2 |
| miR-219 | ugauuguccaaacgcaauucu | 457 | miR-219; miR-219-1; miR-219-2 |
| miR-220 | ccacaccguaucugacacuuu | 458 | miR-220 |
| miR-221 | agcuacauugucugcuggguuuc | 459 | miR-221 |
| miR-222 | agcuacaucuggcuacuggguceuc | 460 | miR-222 |
| miR-223 | ugucaguuugucaaauacccc | 461 | miR-223 |
| miR-224 | caagucacuagugguuccguuua | 462 | miR-224 |
| miR-296 | agggcccccccucaauccugu | 463 | miR-296 |
| miR-299 | ugguuuaccguccacauacau | 464 | miR-299 |
| miR-301 | cagugcaauaguauugucaaagc | 465 | miR-301 |
| miR-302a | uaagugcuuccauguuuuggaga | 466 | miR-302a |
| miR-302b* | acuuuaacauggaagugcuuucu | 467 | miR-302b |
| miR-302b | uaagugcuuccauguuuuaguag | 468 | miR-302b |
| miR-302c* | uuuaacauggggguaccugcug | 469 | miR-302c |
| miR-302c | uaagugcuuccauguuucagugg | 470 | miR-302c |
| miR-302d | uaagugcuuccauguuugagugu | 471 | miR-302d |
| miR-320 | aaaagcuggguugagagggcgaa | 472 | miR-320 |
| miR-321 | uaagccagggauugugggguuc | 473 | miR-321 |
| miR-323 | gcacauuacacggucgaccucu | 474 | miR-323 |
| miR-324-5p | cgcauccccuagggcauuggugu | 475 | miR-324 |
| miR-324-3p | ccacugccccaggugcugcugg | 476 | miR-324 |
| miR-325 | ccuaguagguguccaguaagu | 477 | miR-325 |
| miR-326 | ccucugggcccuuccuccag | 478 | miR-326 |
| miR-328 | cuggcccucucugcccuuccgu | 479 | miR-328 |
| miR-330 | gcaaagcacacggccugcagaga | 480 | miR-330 |
| miR-331 | gccccugggccuauccuagaa | 481 | miR-331 |
| miR-335 | ucaagagcaauaacgaaaaaugu | 482 | miR-335 |
| miR-337 | uccagcuccuauaugaugccuuu | 483 | miR-337 |
| miR-338 | uccagcaucagugauuuuguuga | 484 | miR-338 |
| miR-339 | ucccuguccuccaggagcuca | 485 | miR-339 |
| miR-340 | uccgucucaguuacuuuauagcc | 486 | miR-340 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-342 | ucucacacagaaaucgcacccguc | 487 | miR-342 |
| miR-345 | ugcugacuccuaguccagggc | 488 | miR-345 |
| miR-346 | ugucugcccgcaugccugccucu | 489 | miR-346 |
| miR-367 | aauugcacuuuagcaaugguga | 490 | miR-367 |
| miR-368 | acauagaggaaauuccacguuu | 491 | miR-368 |
| miR-369 | aauaauacaugguugaucuuu | 492 | miR-369 |
| miR-370 | gccugcuggggguggaaccugg | 493 | miR-370 |
| miR-371 | gugccgccaucuuuugagugu | 494 | miR-371 |
| miR-372 | aaagugcugcgacauuugagcgu | 495 | miR-372 |
| miR-373* | acucaaaauggggcgcuuucc | 496 | miR-373 |
| miR-373 | gaagugcuucgauuuugggugu | 497 | miR-373 |
| miR-374 | uuauaauacaaccugauaagug | 498 | miR-374 |

The present invention encompasses methods of diagnosing whether a subject has, or is at risk for developing, a solid cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, a solid cancer. In a preferred embodiment, the subject is a human who has, or is suspected of having, a solid cancer.

In one embodiment, the at least one miR gene product measured in the test sample is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof. In a particular embodiment, the miR gene product is miR-21, miR-191 or miR-17-5p. In another embodiment, the miR gene product is not miR-15a or miR-16-1. In an additional embodiment, the miR gene product is not miR 159-1 or miR-192. In an additional embodiment, the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the miR gene product is not miR-21, miR-301, miR-142 as, miR-142s, miR-194, miR-215, or miR-32. In another embodiment, the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the miR gene product is not miR-15a, miR-16-1, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186.

The solid cancer can be any cancer that arises from organs and solid tissues. Such cancers are typically associated with the formation and/or presence of tumor masses and can be carcinomas, sarcomas and lymphomas. Specific examples of solid cancers to be diagnosed by the methods of the invention include, but are not limited to, colon cancer, rectal cancer, stomach (gastric) cancer, pancreatic cancer, breast cancer, lung cancer, prostate cancer, bronchial cancer, testicular cancer, ovarian cancer, uterine cancer, penile cancer, melanoma and other skin cancers, liver cancer, esophogeal cancer, cancers of the oral cavity and pharynx (e.g., tongue cancer, mouth cancer), cancers of the digestive system (e.g., intestinal cancer, gall bladder cancer), bone and joint cancers, cancers of the endocrine system (e.g., thyroid cancer), brain cancer, eye cancer, cancers of the urinary system (e.g., kidney cancer, urinary bladder cancer), Hodgkin disease and non-Hodgkin lymphoma. In particular embodiments, the solid cancer is not one or more of breast cancer, lung cancer, prostate cancer, pancreatic cancer or gastrointestinal cancer.

In one embodiment, the solid cancer is breast cancer or lung cancer and the at least one miR gene product measured in the test sample is selected from the group consisting of miR-210, miR-213 and a combination thereof.

In a further embodiment, the solid cancer is colon cancer, stomach cancer, prostate cancer or pancreas cancer and the at least one miR gene product measured in the test sample is miR-218-2.

In a certain embodiment of the invention, the solid cancer is breast cancer and the at least one miR gene product measured in the test sample is selected from the group consisting of miR-125b-1, miR-125b-2, miR-145, miR-21 and combinations thereof. In a related embodiment, the solid cancer is breast cancer and the at least one miR gene product in the test sample is selected from the group consisting of miR-21, miR-29b-2, miR-146, miR-125b-2, miR-125b-1, miR-10b, miR-145, miR-181a, miR-140, miR-213, miR-29a prec, miR-181b-1, miR-199b, miR-29b-1, miR-130a, miR-155, let-7a-2, miR-205, miR-29c, miR-224, miR-100, miR-31, miR-30c, miR-17-5p, miR-210, miR-122a, miR-16-2 and combinations thereof. In a related embodiment, the solid cancer is breast cancer and the at least one miR gene product is not miR-15a or miR-16-1. In a further embodiment, the solid cancer is breast cancer and the at least one miR gene product is not miR-145, miR-21, miR-155, miR-10b, miR-125b-1, miR-125b-2, let7a-2, let7a-3, let-7d, miR-122a, miR-191, miR-206, miR-210, let-71, miR-009-1 (miR131-1), miR-34 (miR-170), miR-102 (miR-29b), miR-123 (miR-126), miR-140-as, miR-125a, miR-194, miR-204, miR-213, let-7f-2, miR-01, miR-128b, miR-136, miR-143, miR-149, miR-191, miR-196-1, miR-196-2, miR-202, miR-103-1, or miR-30c. In another embodiment, the solid cancer is breast cancer and the miR gene product is not miR-21, miR-125b-1, let-7a-2, let-71, miR-100, let-7g, miR-31, miR-32a-1, miR-33b, miR-34a-2, miR-101-1, miR-135-1, miR-142 as, miR-142s, miR-144, miR-301, miR-29c, miR-30c, miR-106a, or miR-29b-1. In yet another embodiment, the solid cancer is breast cancer and the miR gene product is not miR-159-1 or miR-192. In an additional embodiment, the solid cancer is breast cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is breast cancer and the miR gene product is not miR-21, miR-301, miR-142 as, miR-142s, miR-194, miR-215, or miR-32. In another embodiment, the solid cancer is breast cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is breast cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In another embodiment, the solid cancer is colon cancer and the at least one miR gene product in the test sample is selected from the group consisting of miR-24-1, miR-29b-2, miR-20a, miR-10a, miR-32, miR-203, miR-106a, miR-17-5p, miR-30c, miR-223, miR-126*, miR-128b, miR-21, miR-24-2, miR-99b prec, miR-155, miR-213, miR-150, miR-107, miR-191, miR-221, miR-9-3 and combinations thereof. In another embodiment, the solid cancer is colon cancer and the miR gene product is not miR 159-1 or miR-192. In an additional embodiment, the solid cancer is colon cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is colon cancer and the miR gene product is not miR-21, miR-301, miR-142 as, miR-142s, miR-194, miR-215, or miR-32. In another embodiment, the solid cancer is colon cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is colon cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In yet another embodiment, the solid cancer is lung cancer and the miR gene product in the test sample is selected from the group consisting of miR-21, miR-205, miR-200b, miR-9-1, miR-210, miR-148, miR-141, miR-132, miR-215, miR-128b, let-7g, miR-16-2, miR-129-1/2 prec, miR-126*, miR-142-as, miR-30d, miR-30a-5p, miR-7-2, miR-199a-1, miR-127, miR-34a prec, miR-34a, miR-136, miR-202, miR-196-2, miR-199a-2, let-7a-2, miR-124a-1, miR-149, miR-17-5p, miR-196-1 prec, miR-10a, miR-99b prec, miR-196-1, miR-199b, miR-191, miR-195, miR-155 and combinations thereof. In a related embodiment, the solid cancer is lung cancer and the at least one miR gene product is not miR-15a or miR-16-1. In a further embodiment, the solid cancer is lung cancer and the at least one miR gene product is not miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-192, miR-224, miR-24-2, miR-212, miR-9, miR-17, miR-124a-1, miR-95, miR-198, miR-216, miR-219-1, miR-197, miR-125a, miR-26a-1, miR-146, miR-199b, let7a-2, miR-27b, miR-32, miR-29b-2, miR-33, miR-181c, miR-101-1, miR-124a-3, miR-125b-1 or let7f-1. In another embodiment, the solid cancer is lung cancer and the at least one miR gene product is not miR-21, miR-182, miR-181, miR-30, miR-15a, miR-143, miR-205, miR-96, miR-103, miR-107, miR-129, miR-137, miR-186, miR-15b, miR-16-2, miR-195, miR-34, miR-153, miR-217, miR-204, miR-211, miR-9, miR-217, let-7a-2 or miR-32. In a further embodiment, the solid cancer is lung cancer and the miR gene product is not let-7c, let-7g, miR-7-3, miR-210, miR-31, miR-34a-1, miR-a-2, miR-99a, miR-100, miR-125b-2, miR-132, miR-135-1, miR-195, miR-34, miR-123, miR-203. In another embodiment, the solid cancer is lung cancer and the miR gene product is not miR 159-1 or miR-192. In an additional embodiment, the solid cancer is lung cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is lung cancer and the miR gene product is not miR-21, miR-301, miR-142 as, miR-142s, miR-194, miR-215, or miR-32. In another embodiment, the solid cancer is lung cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is lung cancer and the miR gene product is not miR-181b, miR-181 c, miR-181d, miR-30, miR-15b, miR-16-2, miR-153-1, miR-217, miR-205, miR-204, miR-103, miR-107, miR-129-2, miR-9 or miR-137.

In a further embodiment, the solid cancer is pancreatic cancer and the at least one miR gene product measured in the test sample is selected from the group consisting of miR-103-1, miR-103-2, miR-155, miR-204 and combinations thereof. In a related embodiment, the solid cancer is pancreatic cancer and the miR gene product in the test sample is selected from the group consisting of miR-103-2, miR-103-1, miR-24-2, miR-107, miR-100, miR-125b-2, miR-125b-1, miR-24-1, miR-191, miR-23a, miR-26a-1, miR-125a, miR-130a, miR-26b, miR-145, miR-221, miR-126*, miR-16-2, miR-146, miR-214, miR-99b, miR-128b, miR-155, miR-29b-2, miR-29a, miR-25, miR-16-1, miR-99a, miR-224, miR-30d, miR-92-2, miR-199a-1, miR-223, miR-29c, miR-30b, miR-129-1/2, miR-197, miR-17-5p, miR-30c, miR-7-1, miR-93-1, miR-140, miR-30a-5p, miR-132, miR-181b-1, miR-152 prec, miR-23b, miR-20a, miR-222, miR-27a, miR-92-1, miR-21, miR-129-1/2 prec, miR-150, miR-32, miR-106a, miR-29b-1 and combinations thereof. In one embodiment, the solid cancer is pancreatic cancer and the miR gene product is not miR-15a or miR-16-1. In another embodiment, the solid cancer is pancreatic cancer and the miR gene product is not miR 159-1 or miR-192. In an additional embodiment, the solid cancer is pancreatic cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is pancreatic cancer and the miR gene product is not miR-21, miR-301, miR-142 as, miR-142s, miR-194, miR-215, or miR-32. In another embodiment, the solid cancer is pancreatic cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is pancreatic cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In another embodiment, the solid cancer is prostate cancer and the miR gene product in the test sample is selected from the group consisting of let-7d, miR-128a prec, miR-195, miR-203, let-7a-2 prec, miR-34a, miR-20a, miR-218-2, miR-29a, miR-25, miR-95, miR-197, miR-135-2, miR-187, miR-196-1, miR-148, miR-191, miR-21, let-71, miR-198, miR-199a-2, miR-30c, miR-17-5p, miR-92-2, miR-146, miR-181b-1 prec, miR-32, miR-206, miR-184 prec, miR-29a prec, miR-29b-2, miR-149, miR-181b-1, miR-196-1 prec, miR-93-1, miR-223, miR-16-1, miR-101-1, miR-124a-1, miR-26a-1, miR-214, miR-27a, miR-24-1, miR-106a, miR-199a-1 and combinations thereof. In a related embodiment, the solid cancer is prostate cancer and the miR gene product is not miR-15a or miR-16-1. In another embodiment, the solid cancer is prostate cancer and the miR gene product is not miR 159-1 or miR-192. In an additional embodiment, the solid cancer is prostate cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is prostate cancer and the miR gene product is not miR-21, miR-301, miR-142 as, miR-142s, miR-194, miR-215, or miR-32. In another embodiment, the solid cancer is prostate cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is prostate cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In yet another embodiment, the solid cancer is stomach cancer and the miR gene product in the test sample is selected from the group consisting of miR-223, miR-21, miR-218-2, miR-103-2, miR-92-2, miR-25, miR-136, miR-191, miR-221, miR-125b-2, miR-103-1, miR-214, miR-222, miR-212 prec, miR-125b-1, miR-100, miR-107, miR-92-1, miR-96, miR-192, miR-23a, miR-215, miR-7-2, miR-138-2, miR-24-1, miR-99b, miR-33b, miR-24-2 and combinations thereof. In a related embodiment, the solid cancer is stomach cancer and the miR gene product is not miR-15a or miR-16-1. In another embodiment, the solid cancer is stomach cancer and the miR gene product is not miR 159-1 or miR-192. In an additional embodiment, the solid cancer is stomach cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is stomach cancer and the miR gene product is not miR-21, miR-301, miR-142 as, miR-142s, miR-194, miR-215, or miR-32. In another embodiment, the solid cancer is stomach cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is stomach cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

The level of at least one miR gene product can be measured in a biological sample (e.g., cells, tissues) obtained from the subject. For example, a tissue sample (e.g., from a tumor) can be removed from a subject suspected of having a solid cancer by conventional biopsy techniques. In another embodiment, a blood sample can be removed from the subject, and blood cells (e.g., white blood cells) can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. A reference miR expression standard for the biological sample can also be used as a control.

An alteration (e.g., an increase or decrease) in the level of a miR gene product in the sample obtained from the subject, relative to the level of a corresponding miR gene product in a control sample, is indicative of the presence of a solid cancer in the subject. In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences provided in Table 1a and Table 1b and include, but are not limited to, probes having at least about 70%, 75%, 80%, 85%, 90%, 95%, 98%, 99% or complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^{8}$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98%, 99% or complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in solid cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancerous (e.g., tumor) tissue, and within cancerous tissue, different prognosis states (for example, good or poor long term survival prospects) may be determined. By comparing expression profiles of solid cancer tissue in different states, information regarding which genes are important (including both up- and down-regulation of genes) in each of these states is obtained. The identification of sequences that are differentially expressed in solid cancer tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the solid cancer expression profile or convert a poor prognosis profile to a better prognosis profile.

Accordingly, the invention provides methods of diagnosing whether a subject has, or is at risk for developing, a solid cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, a solid cancer. In one embodiment, the microarray comprises miRNA-specific probe oligonucleotides for a substantial portion of all known human miRNAs. In a particular embodiment, the microarray comprises miRNA-specific probe oligonucleotides for one or more miRNAs selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., a solid cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs.

zero signal). More preferably, the profile recorded includes the intensity of the signal from each hybridization. The profile is compared to the hybridization profile generated from a normal, i.e., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with a solid cancer, comprising measuring the level of at least one miR gene product, which is associated with a particular prognosis in a solid cancer (e.g., a good or positive prognosis, a poor or adverse prognosis), in a test sample from the subject. According to these methods, an alteration in the level of a miR gene product that is associated with a particular prognosis in the test sample, as compared to the level of a corresponding miR gene product in a control sample, is indicative of the subject having a solid cancer with a particular prognosis. In one embodiment, the miR gene product is associated with an adverse (i.e., poor) prognosis. Examples of an adverse prognosis include, but are not limited to, low survival rate and rapid disease progression. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of solid cancers. Therefore, altering the level of the miR gene product (e.g., by decreasing the level of a miR gene product that is up-regulated in solid cancer cells, by increasing the level of a miR gene product that is down-regulated in solid cancer cells) may successfully treat the solid cancer.

Accordingly, the present invention encompasses methods of inhibiting tumorigenesis in a subject who has, or is suspected of having, a solid cancer wherein at least one miR gene product is deregulated (e.g., down-regulated, up-regulated) in the cancer cells of the subject. When the at least one isolated miR gene product is down-regulated in the cancer cells (e.g., miR-145, miR-155, miR-218-2), the method comprises administering an effective amount of the at least one isolated miR gene product, or an isolated variant or biologically-active fragment thereof, such that proliferation of cancer cells in the subject is inhibited. In one embodiment, the isolated miR gene product that is administered is not miR-15a or miR-16-1. In another embodiment, the miR gene product is not miR 159-1 or miR-192. In an additional embodiment, the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the miR gene product is not miR-21, miR-301, miR-142 as, miR-142s, miR-194, miR-215, or miR-32. In another embodiment, the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the miR gene product is not miR-30, miR-15b, miR-16-2, miR-217, miR-205, miR-204, miR-103, miR-107, miR-9, and miR-137. In a further embodiment, the miR gene product is not miR-145, miR-21, miR-155, miR-10b, miR-125b-1, miR-125b-2, let7a-2, let7a-3, let-7d, miR-122a, miR-191, miR-206, miR-210, let-71, miR-009-1 (miR131-1), miR-34 (miR-170), miR-102 (miR-29b), miR-123 (miR-126), miR-140-as, miR-125a, miR-194, miR-204, miR-213, let-7f-2, miR-101, miR-128b, miR-136, miR-143, miR-149, miR-191, miR-196-1, miR-196-2, miR-202, miR-103-1, or miR-30c. In another embodiment, the miR gene product is not miR-21, miR-125b-1, let-7a-2, let-7i, miR-100, let-7g, miR-31, miR-32a-1, miR-33b, miR-34a-2, miR-101-1, miR-135-1, miR-142 as, miR-142s, miR-144, miR-301, miR-29c, miR-30c, miR-106a, or miR-29b-1.

For example, when a miR gene product is down-regulated in a cancer cell in a subject, administering an effective amount of an isolated miR gene product to the subject can inhibit proliferation of the cancer cell. The isolated miR gene product that is administered to the subject can be identical to the endogenous wild-type miR gene product (e.g., a miR gene product shown in Table 1a or Table 1b) that is down-regulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with solid cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with solid cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of at least one compound for inhibiting expression of the at least one miR gene product, referred to herein as miR gene expression-inhibition compounds, such that proliferation of solid cancer cells is inhibited. In a particular embodiment, the at least one miR expression-inhibition compound is specific for a miR gene product selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof. A miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, for example, a solid cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from a solid cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating a solid cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Domburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., a solid cancer). One skilled in the art can readily determine an effective amount of a miR expression-inhibition compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibition compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression of (e.g., inhibit translation of, induce cleavage or destruction of) the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g. RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences for the miR gene products are provided in Tables 1a and 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a solid cancer. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibition compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibition compounds can be administered to a subject by any means suitable for delivering these compounds to cancer cells of the subject. For example, the miR gene products or miR expression-inhibition compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibition compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibition compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibition compound can be administered to the subject either as naked RNA, in combination with a delivery reagent, or as a nucleic acid (e.g., a recombinant plasmid or viral vector) comprising sequences that express the miR gene product or miR gene product expression-inhibition compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression-inhibition compounds, and techniques for delivering such plasmids and vectors to cancer cells, are discussed herein and/or are well known in the art.

In a particular embodiment, liposomes are used to deliver a miR gene product or miR gene expression-inhibition compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating a solid cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in solid cancer cells relative to suitable control cells. In certain embodiments the isolated miR gene product is selected from the group consisting of miR-145, miR-155, miR-218-2 combinations thereof.

In other embodiments, the pharmaceutical compositions of the invention comprise at least one miR expression-inhibition compound. In a particular embodiment, the at least one miR gene expression-inhibition compound is specific for a miR gene whose expression is greater in solid cancer cells than control cells. In certain embodiments, the miR gene expression-inhibition compound is specific for one or more miR gene products selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising sequences encoding them) (e.g., 0.1 to 90% by weight), or a physiologically-acceptable salt thereof, mixed with a pharmaceutically-acceptable carrier. In certain embodiments, the pharmaceutical compositions of the invention additionally comprise one or more anti-cancer agents (e.g., chemotherapeutic agents). The pharmaceutical formulations of the invention can also comprise at least one miR gene product or miR gene expression-inhibition compound (or at least one nucleic acid comprising sequences encoding them), which are encapsulated by liposomes and a pharmaceutically-acceptable carrier. In one embodiment, the pharmaceutical composition comprises a miR gene or gene product that is not miR-15 and/or miR-16.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising sequences encoding them) that is resistant to degradation by nucleases. One skilled in the art can readily synthesize nucleic acids that are nuclease resistant, for example, by incorporating one or more ribonucleotides that is modified at the 2'-position into the miR gene product. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising sequences encoding them) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising sequences encoding them) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, FOLFOX4.

The invention also encompasses methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in cancer cells. An increase in the level of the miR gene product in the cell after the agent is provided, relative to a suitable control cell (e.g., agent is not provided), is indicative of the test agent being an inhibitor of tumorigenesis. In a particular embodiment, at least one miR gene product associated with decreased expression levels in cancer cells is selected from the group consisting of miR-145, miR-155, miR-218-2 and combinations thereof.

In other embodiments the method comprises providing a test agent to a cell and measuring the level of at least one miR gene product associated with increased expression levels in cancer cells. A decrease in the level of the miR gene product in the cell after the agent is provided, relative to a suitable control cell (e.g., agent is not provided), is indicative of the test agent being an inhibitor of tumorigenesis. In a particular embodiment, at least one miR gene product associated with increased expression levels in cancer cells is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described hereinabove.

The invention will now be illustrated by the following non-limiting examples.

EXEMPLIFICATION

The following Materials and Methods were used in the Examples:
Samples

A total of 540 samples, including 363 primary tumor samples and 177 normal tissues, were used in this study (Table 2). The following solid cancers were represented: lung carcinoma, breast carcinoma, prostate carcinoma, stomach carcinoma, colon carcinoma and pancreatic endocrine tumors. All samples were obtained with informed consent from each patient and were confirmed histologically. Normal samples were paired with samples from individuals affected with lung and stomach carcinoma, and from normal individuals for the remaining tissues. All normal breast samples were obtained by pooling 5 unrelated normal tissues. Total RNA was isolated from tissues using TRIzol™ reagent (Invitrogen), according to manufacturer's instructions.

MicroRNA Microarrays

Microarray analysis was performed as previously described (Liu, C.-G., et al., *Proc. Natl. Acad. Sci. USA* 101: 11755-11760 (2004)). Briefly, 5 µg of total RNA was used for hybridization on miRNA microarray chips. These chips contain gene-specific 40-mer oligonucleotide probes, spotted by contacting technologies and covalently attached to a polymeric matrix. The microarrays were hybridized in 6×SSPE (0.9 M NaCl/60 mM NaH$_2$PO$_4$.H$_2$O/8 mM EDTA, pH 7.4)/ 30% formamide at 25° C. for 18 hr, washed in 0.75×TNT (Tris.HCl/NaCl/Tween 20) at 37° C. for 40 min, and processed using direct detection of the biotin-labeled transcripts by streptavidin-Alexa647 (Molecular Probes) conjugate. Processed slides were scanned using a microarray scanner (GenePix Pro, Axon), with the laser set to 635 nm, at fixed PMT setting and a scan resolution of 10 mm. The data were confirmed by Northern blotting as described (Calin, G. A., et al., *Proc. Natl. Acad. Sci. USA* 101:11755-11760 (2004); Iorio, M. V., et al., *Cancer Res.* 65: 7065-7070 (2005)).

TABLE 2

Samples used in the study (tumors and corresponding normals).

| Tumour type | Cancer Samples | Normal Samples |
|---|---|---|
| Lung carcinoma | 123 | 123 |
| Breast carcinoma | 79 | 6* |
| Colon carcinoma | 46 | 8 |
| Gastric carcinoma | 20 | 21 |
| Endocrine pancreatic tumours | 39 | 12 |
| Prostate cancer | 56 | 7 |
| All tissues (527) | 363 | 177 |

*Pools of 5 unrelated normal breast tissues per sample (for a total of 30 unrelated individuals).

Computational Analysis

Microarray images were analyzed using GenePix Pro (Axon). Average values of the replicate spots of each miRNA were background-subtracted, normalized and subjected to further analysis. Normalization was performed by using a per chip median normalization method, using the median array as a reference. Finally, miRNAs measured as present in at least the smallest of the two classes in a dataset were selected. Absent calls were thresholded to 4.5 prior to statistical analysis. This level is the average minimum intensity level detected in the experiments. MicroRNA nomenclature was according to the Genome Browser (www.genome.ucsc.edu) and the microRNA database at Sanger Center (Griffiths-Jones, S., *Nucleic Acids Res* 32: D109-11 (2004)); in case of discrepancies we followed the microRNA database. Differentially-expressed microRNAs were identified by using the t test procedure within significance analysis of microarrays (SAM) (Tusher, V. G., et al., *Proc Natl Acad Sci USA* 98: 5116-21 (2001). SAM calculates a score for each gene on the basis of the change in expression relative to the standard deviation of all measurements. Within SAM, t test was used.

The microRNA signatures were determined by applying nearest shrunken centroids method. This method identifies a subgroup of genes that best characterizes each solid cancer from its respective normal counterpart. The prediction error was calculated by means of 10-fold cross validation, and for each cancer, we obtained the miR signature that resulted in the minimal prediction error. A resampling test was performed by random permutation analysis to compute the p-value of the shared signature.

EXAMPLE 1

Identification of a MicroRNA Expression Signature in Human Solid Cancers Statistics The combined cancers/normal tissue comparison was conducted using a reduced number of lung samples (80 cancer and 40 normal samples), in order to balance the different tissues numerically, yielding a total of 404 samples. For statistical analysis, 137 miRs, whose expression values were above 256 (threshold value) in at least 50% of the samples, were retained from the 228 that were measured. A T test was used to identify differentially-expressed microRNAs (Table 3). The p-values of the T test were corrected for multiple testing procedures and to control Type I error rates. Adjusted p-values were obtained by performing resampling with 500,000 permutations (Jung, S. H., et al. *Biostatistics* 6: 157-69 (2005)). This analysis was performed in order to evaluate the results by using the same method as Lu and co-workers (Lu, J., et al., *Nature* 435: 834-8 (2005)).

As an alternative to T test, significance analysis of microarrays (SAM) was used to identify differentially-expressed microRNAs. This procedure allows for the control of false detection rate (FDR). The delta was chosen to result in an FDR less than or equal to 0.01. microRNA subsets which result in the best tumor classification, i.e., which best predict the two classes (cancer and normal), were then identified using the method of the nearest shrunken centroids, as implemented in PAM (prediction analysis of microarray). The prediction error was calculated by means of 10-fold cross validation. The microRNAs were selected yielding the minimum misclassification error after cross-validation.

Results

By T-test, 43 differentially-expressed miRs with an adjusted p-value below 0.05 were obtained (Table 3). Twenty six miRs were overexpressed and 17 were under-expressed relative to corresponding normal tissues when the six solid cancers are grouped together (breast, colon, lung, pancreas, prostate, stomach). These results indicated that the spectrum of expressed miRNAs in solid cancers is very different from that of normal cells (43 out of 137 miRNAs, 31%). Using SAM, 49 miRNAs were identified as differentially-expressed, of which 34 were up-regulated (Table 4). Using PAM, 36 over-expressed miRNAs in cancer (indicated by positive cancer scores) and 21 down-regulated miRs (indicated by negative cancer scores) were identified as differentially-expressed (Table 5). However, these analyses are not tailored to identify alterations in miR expression that consistently result in transformation, because miR expression is heavily tissue-specific (He, L., et al. *Nature* 435: 828-833 (2005); also see FIG. 1 and FIG. 2).

Figure 2:
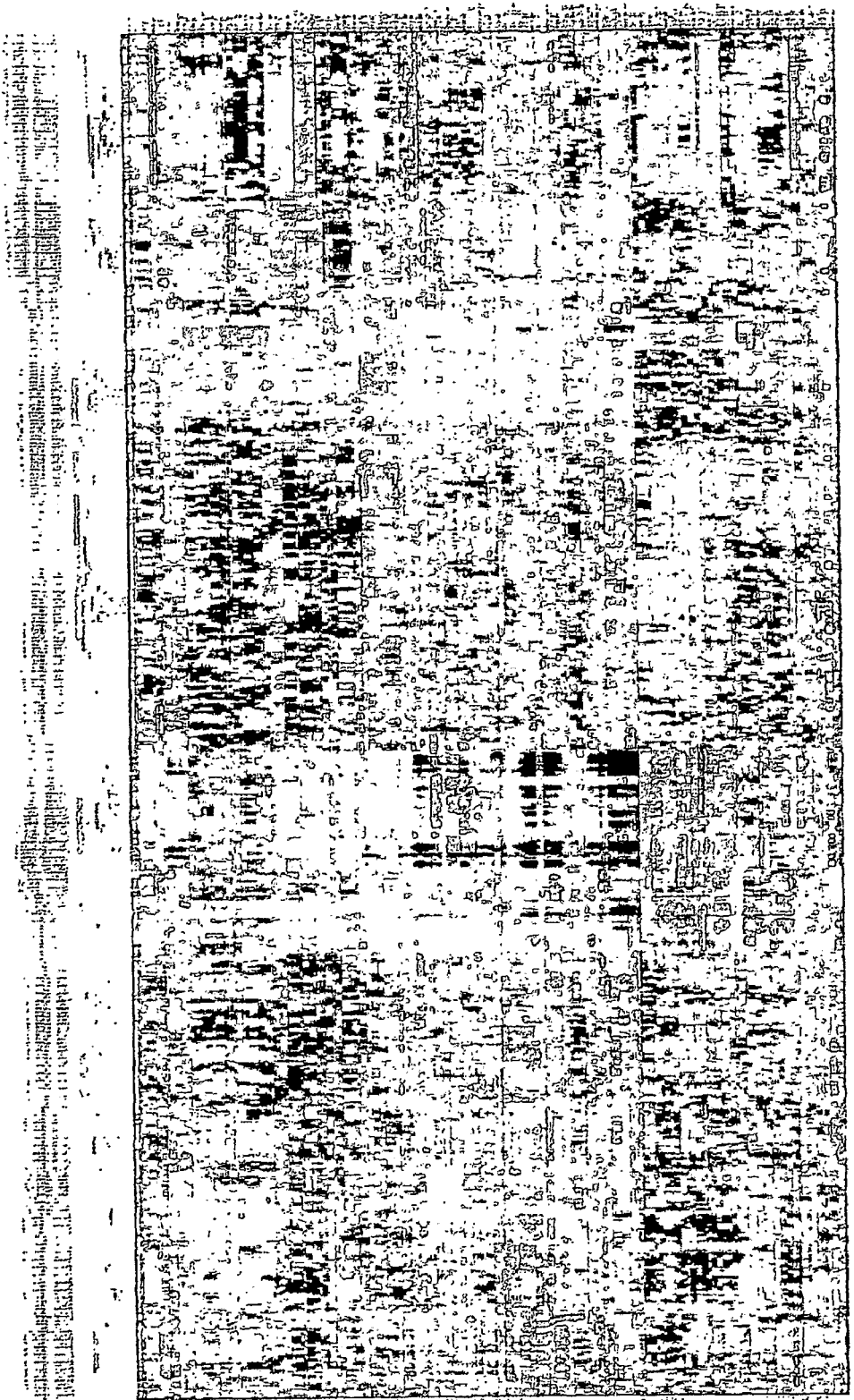
FIG. 2 depicts unsupervised analysis of microRNA expression data. MicroRNA profiling of 540 samples (indicated at top of panel) covering breast, colon, lung, pancreas, prostate and stomach (normal tissues and tumors) were filtered, centered and normalized for each feature. The data were subject to hierarchical clustering on both the samples (horizontally-oriented) and the features (vertically-oriented with average linkage and Pearson correlation as a similarity measure. Sample names are indicated at the top of the figure and miRNA names on the left. The probe ID is indicated in parentheses, as the same microRNA can be measured by different oligonucleotides. The colors indicate the difference in expression level from the median for the microRNAs in each sample.

The clustering of miRs based on expression profiles derived from 363 solid cancer and 177 normal samples using 228 miRs is shown in FIG. 1. The tree, which shows a very good separation between the different tissues, was constructed using 137 different miRNAs that were expressed in at least 50% of the samples used in the study.

TABLE 3

Differentially regulated miRs in 6 solid cancer types vs. normal tissues (T test stats.)*.

| miR | ID | Cancer Mean | Normal Mean | Test stat | Raw p | Adj p |
|---|---|---|---|---|---|---|
| miR-21 | #47 | 11.538663 | 9.648338 | 7.861136 | 2.00E−06 | 2.00E−06 |
| miR-141 | #137 | 9.024091 | 7.905398 | 6.238014 | 2.00E−06 | 2.00E−06 |
| miR-212 | #208 | 13.540651 | 14.33617 | −6.57942 | 2.00E−06 | 2.00E−06 |
| miR-128a prec | #113 | 12.32588 | 13.522675 | −6.76388 | 2.00E−06 | 2.00E−06 |
| miR-138-2 | #133 | 11.739557 | 13.144746 | −7.01204 | 2.00E−06 | 2.00E−06 |
| miR-218-2 | #221 | 11.279787 | 12.539366 | −7.40557 | 2.00E−06 | 2.00E−06 |
| miR-23b | #51 | 14.169748 | 15.949736 | −8.37744 | 2.00E−06 | 2.00E−06 |
| miR-195 | #184 | 10.343991 | 9.172985 | 5.763262 | 2.00E−06 | 1.00E−05 |
| miR-212 prec | #209 | 12.686966 | 13.661763 | −5.83132 | 4.00E−06 | 1.00E−05 |
| miR-29b-2 | #95 | 11.27556 | 9.940731 | 5.660854 | 2.00E−06 | 1.40E−05 |
| miR-199a-1 | #191 | 10.032008 | 8.920183 | 5.528849 | 2.00E−06 | 3.00E−05 |
| miR-9-3 | #28 | 11.461922 | 12.570412 | −5.43006 | 2.00E−06 | 4.60E−05 |
| miR-128a | #114 | 13.024235 | 13.856624 | −5.35102 | 6.00E−06 | 7.20E−05 |
| let-7a-1 | #1 | 12.616569 | 13.455246 | −5.35346 | 2.00E−06 | 7.20E−05 |
| let-7b | #5 | 13.42636 | 14.068521 | −5.17701 | 1.00E−05 | 0.000146 |
| miR-16-2 | #39 | 10.460707 | 9.305895 | 5.048375 | 4.00E−06 | 0.000224 |
| miR-199a-2 | #192 | 9.714225 | 8.759237 | 4.862553 | 1.00E−05 | 0.000494 |
| miR-152 prec | #151 | 11.388676 | 12.357529 | −4.83716 | 2.00E−06 | 0.00053 |
| miR-16-1 | #38 | 10.443169 | 9.338182 | 4.755258 | 1.00E−05 | 0.00071 |
| miR-30d | #72 | 13.982017 | 14.775206 | −4.5707 | 1.20E−05 | 0.001476 |
| miR-34a | #78 | 10.675566 | 9.63769 | 4.467301 | 2.60E−05 | 0.00217 |
| miR-17-5p | #41 | 11.567244 | 10.281468 | 4.341834 | 3.80E−05 | 0.0034 |
| miR-128b | #115 | 10.930395 | 9.947746 | 4.304764 | 3.80E−05 | 0.003912 |
| miR-20a | #46 | 11.409852 | 10.19284 | 4.304678 | 3.20E−05 | 0.003912 |
| miR-181b-1 prec | #211 | 9.577504 | 8.804294 | 4.285968 | 4.80E−05 | 0.004126 |
| miR-132 | #121 | 9.599947 | 8.775966 | 4.284737 | 5.60E−05 | 0.004126 |
| miR-200b | #195 | 9.475221 | 8.527243 | 4.221511 | 4.00E−05 | 0.0052 |
| let-7u-3 | #4 | 10.436089 | 9.511546 | 4.08952 | 0.000104 | 0.008242 |
| miR-138-1 | #132 | 8.299613 | 9.200253 | −4.05204 | 5.60E−05 | 0.00931 |
| miR-29c | #65 | 11.291005 | 10.326912 | 4.019385 | 0.000144 | 0.010312 |
| miR-29a | #62 | 11.381359 | 10.461075 | 4.013697 | 0.00015 | 0.010398 |
| miR-96 | #86 | 11.37218 | 12.136636 | −3.94825 | 0.000138 | 0.012962 |

TABLE 3-continued

Differentially regulated miRs in 6 solid cancer types vs. normal tissues (T test stats.)*.

| miR | ID | Cancer Mean | Normal Mean | Test stat | Raw p | Adj p |
|---|---|---|---|---|---|---|
| miR-191 | #177 | 13.498207 | 12.729872 | 3.817228 | 0.000158 | 0.02015 |
| miR-27a | #59 | 10.399338 | 9.548582 | 3.715048 | 0.000344 | 0.028096 |
| let-7g | #15 | 10.819688 | 10.01157 | 3.653239 | 0.000426 | 0.033874 |
| miR-9-1 | #24 | 10.102819 | 9.212988 | 3.651886 | 0.000388 | 0.033874 |
| miR-125a | #107 | 10.960998 | 10.005312 | 3.651356 | 0.000452 | 0.033874 |
| miR-95 | #84 | 9.435733 | 8.751331 | 3.59406 | 0.000478 | 0.039594 |
| miR-155 | #157 | 12.505359 | 13.231221 | −3.58369 | 0.000614 | 0.040394 |
| miR-199b | #194 | 9.755066 | 9.082751 | 3.55934 | 0.000588 | 0.04314 |
| miR-24-2 | #54 | 12.611696 | 11.612557 | 3.518774 | 0.00087 | 0.048278 |
| let-7e | #11 | 12.497795 | 13.055093 | −3.51589 | 0.00054 | 0.048354 |
| miR-92-1 | #81 | 16.081074 | 16.592426 | −3.50446 | 0.000928 | 0.049828 |

*Forty-three miRs have an adjusted p-value lower than 0.05. Twenty-six miRs are overexpressed and 17 down-regulated in breast, colon, lung, pancreas, prostate, stomach carcinomas.

TABLE 4

Differentially regulated miRs in 6 solid cancer types vs. normal tissues (SAM, significance analysis of microarrays)*.

| miR | ID | d. value | stdev | p. value | q. value | R. fold |
|---|---|---|---|---|---|---|
| miR-21 | #47 | 3.156 | 0.24 | 0 | 0 | 2.593 |
| miR-23b | #51 | −3.117 | 0.212 | 0 | 0 | 0.443 |
| miR-138-2 | #133 | −2.514 | 0.2 | 0 | 0 | 0.402 |
| miR-218-2 | #221 | −2.383 | 0.17 | 0 | 0 | 0.384 |
| miR-29b-2 | #95 | 2.246 | 0.236 | 0 | 0 | 1.868 |
| miR-128a prec | #113 | −2.235 | 0.177 | 0 | 0 | 0.368 |
| miR-195 | #184 | 2.085 | 0.203 | 0 | 0 | 1.695 |
| miR-141 | #137 | 2.08 | 0.179 | 0 | 0 | 2.459 |
| miR-199a-1 | #191 | 1.987 | 0.201 | 0 | 0 | 1.945 |
| miR-9-3 | #28 | −1.97 | 0.204 | 0 | 0 | 0.433 |
| miR-16-2 | #39 | 1.966 | 0.229 | 0 | 0 | 1.788 |
| miR-17-5p | #41 | 1.964 | 0.296 | 0 | 0 | 0.725 |
| miR-20a | #46 | 1.898 | 0.283 | 0 | 0 | 0.969 |
| miR-16-1 | #38 | 1.87 | 0.232 | 0 | 0 | 1.447 |
| miR-212 prec | #209 | −1.854 | 0.167 | 0 | 0 | 0.509 |
| miR-34a | #78 | 1.756 | 0.232 | 0 | 0 | 1.219 |
| miR-152 prec | #151 | −1.734 | 0.2 | 0 | 0 | 0.46 |
| miR-199a-2 | #192 | 1.721 | 0.196 | 0 | 0 | 1.838 |
| miR-128b | #115 | 1.674 | 0.228 | 0 | 0 | 1.266 |
| miR-212 | #208 | −1.659 | 0.121 | 0 | 0 | 0.627 |
| let-7a-1 | #1 | −1.628 | 0.157 | 0 | 0 | 0.461 |
| miR-200b | #195 | 1.626 | 0.225 | 0 | 0 | 1.432 |
| miR-128a | #114 | −1.619 | 0.156 | 0 | 0 | 0.511 |
| miR-29c | #65 | 1.611 | 0.24 | 0 | 0 | 1.225 |
| let-7a-3 | #4 | 1.581 | 0.226 | 0 | 0 | 1.109 |
| miR-29a | #62 | 1.565 | 0.229 | 0 | 0 | 1.706 |
| miR-24-2 | #54 | 1.555 | 0.284 | 0 | 0 | 0.831 |
| miR-138-1 | #132 | −1.551 | 0.222 | 0 | 0 | 0.432 |
| miR-125a | #107 | 1.541 | 0.262 | 0 | 0 | 1.164 |
| miR-106a | #99 | 1.514 | 0.275 | 0 | 0 | 0.952 |
| miR-132 | #121 | 1.496 | 0.192 | 0 | 0 | 2.158 |
| miR-30d | #72 | −1.491 | 0.174 | 0 | 0 | 0.424 |
| miR-9-1 | #24 | 1.478 | 0.244 | 0 | 0 | 0.763 |
| miR-27a | #59 | 1.448 | 0.229 | 0 | 0 | 1.174 |
| miR-181b-1 prec | #211 | 1.435 | 0.18 | 0 | 0 | 1.525 |
| let-7g | #15 | 1.394 | 0.221 | 0 | 0 | 1.072 |
| miR-96 | #86 | −1.384 | 0.194 | 0 | 0 | 0.519 |
| miR-191 | #177 | 1.372 | 0.201 | 0 | 0 | 1.165 |
| miR-93-1 | #83 | 1.363 | 0.266 | 0 | 0 | 0.775 |
| miR-136 | #130 | −1.355 | 0.267 | 0 | 0 | 0.364 |
| miR-205 | #201 | 1.343 | 0.309 | 0 | 0 | 1.281 |
| miR-185 | #170 | 1.287 | 0.222 | 0.001 | 0.001 | 0.609 |
| miR-125b-1 | #109 | 1.262 | 0.283 | 0.001 | 0.001 | 1.215 |
| miR-10a | #30 | 1.252 | 0.227 | 0.001 | 0.001 | 1.643 |
| miR-95 | #84 | 1.247 | 0.19 | 0.001 | 0.001 | 1.509 |
| miR-199b | #194 | 1.228 | 0.189 | 0.001 | 0.001 | 1.246 |
| miR-10b | #32 | 1.219 | 0.232 | 0.002 | 0.001 | 1.342 |
| let-7i | #10 | 1.216 | 0.203 | 0.002 | 0.001 | 1.026 |
| miR-210 | #205 | 1.213 | 0.237 | 0.002 | 0.001 | 1.088 |

*Thirty five miRs are over-expressed and 14 are down-regulated in breast, colon, lung, pancreas, prostate, stomach carcinomas (Delta = 0.9, FDR = 0.001).

TABLE 5

MicroRNAs selected by PAM (prediction analysis of microarray) in 6 solid cancer types vs. normal tissues*.

| miR | ID | Solid cancer score | Normal tissues score |
|---|---|---|---|
| miR-21 | #47 | 0.0801 | −0.2643 |
| miR-138-2 | #133 | −0.055 | 0.1815 |
| miR-218-2 | #221 | −0.0535 | 0.1765 |
| miR-23b | #51 | −0.0516 | 0.17 |
| miR-128u prec | #113 | −0.0498 | 0.1642 |
| miR-29b-2 | #95 | 0.0457 | −0.1508 |
| miR-195 | #184 | 0.0404 | −0.1333 |
| miR-17-5p | #41 | 0.0383 | −0.1263 |
| miR-9-3 | #28 | −0.0357 | 0.1176 |
| miR-212 prec | #209 | −0.0342 | 0.1129 |
| miR-20a | #46 | 0.0322 | −0.1061 |
| miR-141 | #137 | 0.0322 | −0.1061 |
| miR-199a-1 | #191 | 0.0319 | −0.1053 |
| miR-16-2 | #39 | 0.0315 | −0.1037 |
| miR-152 prec | #151 | −0.0283 | 0.0933 |
| miR-16-1 | #38 | 0.0277 | −0.0913 |
| miR-34a | #78 | 0.0269 | −0.0886 |
| miR-212 | #208 | −0.0265 | 0.0875 |
| let-7a-1 | #1 | −0.0264 | 0.0872 |
| miR-128a | #114 | −0.0259 | 0.0855 |
| miR-128b | #115 | 0.0254 | −0.0839 |
| miR-24-2 | #54 | 0.0244 | −0.0803 |
| miR-29c | #65 | 0.0224 | −0.0738 |
| miR-199a-2 | #192 | 0.0223 | −0.0736 |
| let-7a-3 | #4 | 0.0221 | −0.073 |
| miR-191 | #177 | 0.0188 | −0.062 |
| miR-125a | #107 | 0.0186 | −0.0613 |
| miR-30d | #72 | −0.0185 | 0.061 |
| miR-29a | #62 | 0.0184 | −0.0608 |
| miR-106a | #99 | 0.0177 | −0.0584 |
| miR-93-1 | #83 | 0.0163 | −0.0537 |
| miR-200b | #195 | 0.0159 | −0.0524 |
| let-7g | #15 | 0.0158 | −0.0521 |
| miR-27a | #59 | 0.0157 | −0.0518 |
| miR-96 | #86 | −0.0156 | 0.0514 |
| let-7b | #5 | −0.0152 | 0.0501 |
| miR-138-1 | #132 | −0.0151 | 0.0499 |

TABLE 5-continued

MicroRNAs selected by PAM (prediction analysis of microarray) in 6 solid cancer types vs. normal tissues*.

| miR | ID | Solid cancer score | Normal tissues score |
|---|---|---|---|
| miR-9-1 | #24 | 0.0136 | −0.0448 |
| miR-181b-1 prec | #211 | 0.0134 | −0.0442 |
| miR-155 | #157 | −0.0128 | 0.0423 |
| miR-132 | #121 | 0.0127 | −0.0418 |
| miR-136 | #130 | −0.0112 | 0.037 |
| let-7i | #10 | 0.0103 | −0.034 |
| miR-210 | #205 | 0.0074 | −0.0245 |
| miR-205 | #201 | 0.0073 | −0.024 |
| *miR-185 | #170 | 0.0071 | −0.0234 |
| miR-24-1 | #52 | 0.007 | −0.023 |
| miR-199b | #194 | 0.0064 | −0.021 |
| miR-125b-1 | #109 | 0.006 | −0.0199 |
| miR-206 prec | #203 | −0.005 | 0.0166 |
| miR-10a | #30 | 0.0045 | −0.015 |
| miR-95 | #84 | 0.0045 | −0.0149 |
| let-7c | #11 | −0.0039 | 0.013 |
| miR-124a-3 | #106 | −0.0028 | 0.0091 |
| miR-10b | #32 | 0.002 | −0.0066 |
| miR-185 prec | #171 | −0.0014 | 0.0047 |
| miR-92-1 | #81 | −2.00E−04 | 5.00E−04 |

*T = 1.5 and misclassification error = 0.176. Thirty six over-expressed miRs in cancer are indicated by positive cancer scores; 21 down-regulated miRs are indicated by negative cancer scores.

EXAMPLE 2

Identification of MicroRNA Expression Signatures Associated with Various Human Solid Cancers Results To identify microRNAs that are prognostic for cancer status associated with solid tumors, without incurring bias due to tissue specificity, an alternative approach was used. First, six tissue-specific signatures, one for each cancer histotype, were obtained by performing independent PAM tests (summarized in Tables 6 and 7) Specific signatures for each cancer are shown in Tables 8-13: e.g., breast-Table 8; colon-Table 9; lung-Table 10; pancreas-Table 11; prostate-Table 12; stomach-Table 13. Using these data, deregulated microRNAs that were shared among the different histotype miRNA signatures were identified (Table 14). In order to compute the p-values for this comparative analysis, a re-sampling test with 1,000, 000 random permutations on the miRNA identity was performed. The p-value was defined as the relative frequency of simulation scores exceeding the real score. Twenty-one misregulated microRNAs that were common to at least 3 types of solid cancers (p-value=2.5×10$^{-3}$) were identified (Table 14).

TABLE 6

MicroRNAs used to classify human cancers and normal tissues*.

| Cancer | Up-regulated miRs | Down-regulated miRs | Misclassification error after 10 fold cross validation |
|---|---|---|---|
| Breast | 15 | 12 | 0.08 |
| Colon | 21 | 1 | 0.09 |
| Lung | 35 | 3 | 0.31 |
| Pancreas | 55 | 2 | 0.02 |
| Prostate | 39 | 6 | 0.11 |
| Stomach | 22 | 6 | 0.19 |

*Median normalization was performed and the method of the nearest shrunken centroids was used to select predictive miRNAs.

TABLE 7

Deregulated microRNAs in solid common cancers*.

| Cancer | PAM Up-regulated | SAM Up-regulated | PAM Down-regulated | SAM Down-regulated |
|---|---|---|---|---|
| Breast | 15 | 3 (FDR = 0.33) | 12 | 47 |
| Colon | 21 | 42 (FDR <= 0.06) | 1 | 5 |
| Lung | 35 | 38 (FDR <= 0.01) | 3 | 3 |
| Pancreas | 55 | 50 (FDR <= 0.01) | 2 | 8 |
| Stomach | 22 | 22 (FDR = 0.06) | 6 | 4 |
| Prostate | 39 | 49 (FDR = 0.06) | 6 | 3 |

*Prediction analysis of microarrays (PAM) identifies those genes which best characterize cancers and normal tissues, whilst significance analysis of microarrays (SAM) identifies all those which have differential expression in the two classes. False detection rates (FDR) computed in SAM are indicated in parenthesis.

TABLE 8

MicroRNAs selected by prediction analysis of microarray (PAM) in breast cancer (cancer vs. normal tissues)*.

| miR | Cancer score | Normal score |
|---|---|---|
| miR-21 (#47) | 0.0331 | −0.4364 |
| miR-29b-2 (#95) | 0.0263 | −0.3467 |
| miR-146 (#144) | 0.0182 | −0.2391 |
| miR-125b-2 (#111) | −0.0174 | 0.2286 |
| miR-125b-1 (#109) | −0.0169 | 0.222 |
| miR-10b (#32) | −0.0164 | 0.2166 |
| miR-145 (#143) | −0.0158 | 0.2076 |
| miR-181a (#158) | 0.0153 | −0.201 |
| miR-140 (#136) | −0.0122 | 0.1613 |
| miR-213 (#160) | 0.0116 | −0.1527 |
| miR-29a prec (#63) | 0.0109 | −0.1441 |
| miR-181b-1 (#210) | 0.0098 | −0.1284 |
| miR-199b (#194) | 0.0089 | −0.1172 |
| miR-29b-1 (#64) | 0.0084 | −0.1111 |
| miR-130a (#120) | −0.0076 | 0.1001 |
| miR-155 (#157) | 0.0072 | −0.0951 |
| let-7a-2 (#3) | −0.0042 | 0.0554 |
| miR-205 (#201) | −0.004 | 0.0533 |
| miR-29c (#65) | 0.0032 | −0.0423 |
| miR-224 (#228) | −0.003 | 0.0399 |
| miR-100 (#91) | −0.0021 | 0.0283 |
| miR-31 (#73) | 0.0017 | −0.022 |
| miR-30c (#70) | −7.00E−04 | 0.009 |
| miR-17-5p (#41) | 7.00E−04 | −0.0089 |
| miR-210 (#205) | 4.00E−04 | −0.0057 |
| miR-122a (#101) | 4.00E−04 | −0.005 |
| miR-16-2 (#39) | −1.00E−04 | 0.0013 |

*27 miRs selected, misclassification error after cross validation of 0.008. Seventeen over-expressed miRs in cancer are indicated by positive cancer scores; 12 down-regulated miRs are indicated by negative cancer scores.

TABLE 9

MicroRNAs selected by prediction analysis of microarray (PAM) in colon (cancer vs. normal tissues)*.

| miR | Cancer score | Normal score |
|---|---|---|
| miR-24-1 (#52) | 0.0972 | −0.5589 |
| miR-29b-2 (#95) | 0.0669 | −0.3845 |
| miR-20a (#46) | 0.0596 | −0.3424 |
| miR-10a (#30) | 0.0511 | −0.2938 |
| miR-32 (#75) | 0.0401 | −0.2306 |
| miR-203 (#197) | 0.0391 | −0.2251 |
| miR-106a (#99) | 0.0364 | −0.2094 |
| miR-17-5p (#41) | 0.0349 | −0.2005 |
| miR-30c (#70) | 0.0328 | −0.1888 |
| miR-223 (#227) | 0.0302 | −0.1736 |
| miR-126* (#102) | 0.0199 | −0.1144 |
| miR-128b (#115) | 0.0177 | −0.102 |
| miR-21 (#47) | 0.0162 | −0.0929 |
| miR-24-2 (#54) | 0.0145 | −0.0835 |
| miR-99b prec (#88) | 0.0125 | −0.0721 |
| miR-155 (#157) | 0.0092 | −0.0528 |

TABLE 9-continued

MicroRNAs selected by prediction analysis of microarray (PAM) in colon (cancer vs. normal tissues)*.

| miR | Cancer score | Normal score |
|---|---|---|
| miR-213 (#160) | 0.0091 | −0.0522 |
| miR-150 (#148) | 0.0042 | −0.0243 |
| miR-107 (#100) | 0.003 | −0.0173 |
| miR-191 (#177) | 0.0028 | −0.0159 |
| miR-221 (#224) | 0.002 | −0.0116 |
| miR-9-3 (#28) | −0.0014 | 0.0083 |

*22 miRs selected, misclassification error after cross validation of 0.09. Twenty-one over-expressed miRs in cancer are indicated by positive cancer scores; 1 down-regulated miR is indicated by a negative cancer score.

TABLE 10

MicroRNAs selected by prediction analysis of microarray (PAM) in lung cancer (cancer vs. normal tissues)*.

| miR | Cancer score | Normal score |
|---|---|---|
| miR-21 (#47) | 0.175 | −0.175 |
| miR-205 (#201) | 0.1317 | −0.1317 |
| miR-200b (#195) | 0.1127 | −0.1127 |
| miR-9-1 (#24) | 0.1014 | −0.1014 |
| miR-210 (#205) | 0.0994 | −0.0994 |
| miR-148 (#146) | 0.0737 | −0.0737 |
| miR-141 (#137) | 0.0631 | −0.0631 |
| miR-132 (#121) | 0.0586 | −0.0586 |
| miR-215 (#213) | 0.0575 | −0.0575 |
| miR-128b (#115) | 0.0559 | −0.0559 |
| let-7g (#15) | 0.0557 | −0.0557 |
| miR-16-2 (#39) | 0.0547 | −0.0547 |
| miR-129-1/2 prec (#118) | 0.0515 | −0.0515 |
| miR-126* (#102) | −0.0406 | 0.0406 |
| miR-142-as (#139) | 0.0366 | −0.0366 |
| miR-30d (#72) | −0.0313 | 0.0313 |
| miR-30a-5p (#66) | −0.0297 | 0.0297 |
| miR-7-2 (#21) | 0.0273 | −0.0273 |
| miR-199a-1 (#191) | 0.0256 | −0.0256 |
| miR-127 (#112) | 0.0254 | −0.0254 |
| miR-34a prec (#79) | 0.0214 | −0.0214 |
| miR-34a (#78) | 0.0188 | −0.0188 |
| miR-136 (#130) | 0.0174 | −0.0174 |
| miR-202 (#196) | 0.0165 | −0.0165 |
| miR-196-2 (#188) | 0.0134 | −0.0134 |
| miR-199a-2 (#192) | 0.0126 | −0.0126 |
| let-7a-2 (#3) | 0.0109 | −0.0109 |
| miR-124a-1 (#104) | 0.0081 | −0.0081 |
| miR-149 (#147) | 0.0079 | −0.0079 |
| miR-17-5p (#41) | 0.0061 | −0.0061 |
| miR-196-1 prec (#186) | 0.0053 | −0.0053 |
| miR-10a (#30) | 0.0049 | −0.0049 |
| miR-99b prec (#88) | 0.0045 | −0.0045 |
| miR-196-1 (#185) | 0.0044 | −0.0044 |
| miR-199b (#194) | 0.0039 | −0.0039 |
| miR-191 (#177) | 0.0032 | −0.0032 |
| miR-195 (#184) | 7.00E−04 | −7.00E−04 |
| miR-155 (#157) | 7.00E−04 | −7.00E−04 |

*38 miRs selected, misclassification error after cross validation of 0.31. Thirty-five over-expressed miRs in cancer are indicated by positive cancer scores; 3 down-regulated miRs are indicated by negative cancer scores.

TABLE 11

MicroRNAs selected by prediction analysis of microarray (PAM) in pancreatic cancer (cancer vs. normal tissues)*.

| miR | Cancer score | Normal score |
|---|---|---|
| miR-103-2 (#96) | 0.4746 | −1.582 |
| miR-103-1 (#97) | 0.4089 | −1.3631 |
| miR-24-2 (#54) | 0.4059 | −1.3529 |
| miR-107 (#100) | 0.3701 | −1.2336 |
| miR-100 (#91) | 0.3546 | −1.182 |
| miR-125b-2 (#111) | 0.3147 | −1.0489 |
| miR-125b-1 (#109) | 0.3071 | −1.0237 |
| miR-24-1 (#52) | 0.2846 | −0.9488 |
| miR-191 (#177) | 0.2661 | −0.887 |
| miR-23a (#50) | 0.2586 | −0.8619 |
| miR-26a-1 (#56) | 0.2081 | −0.6937 |
| miR-125a (#107) | 0.1932 | −0.644 |
| miR-130a (#120) | 0.1891 | −0.6303 |
| miR-26b (#58) | 0.1861 | −0.6203 |
| miR-145 (#143) | 0.1847 | −0.6158 |
| miR-221 (#224) | 0.177 | −0.59 |
| miR-126* (#102) | 0.1732 | −0.5772 |
| miR-16-2 (#39) | 0.1698 | −0.5659 |
| miR-146 (#144) | 0.1656 | −0.552 |
| miR-214 (#212) | 0.1642 | −0.5472 |
| miR-99b (#89) | 0.1636 | −0.5454 |
| miR-128b (#115) | 0.1536 | −0.512 |
| miR-155 (#157) | −0.1529 | 0.5098 |
| miR-29b-2 (#95) | 0.1487 | −0.4956 |
| miR-29a (#62) | 0.1454 | −0.4848 |
| miR-25 (#55) | 0.1432 | −0.4775 |
| miR-16-1 (#38) | 0.1424 | −0.4746 |
| miR-99a (#90) | 0.1374 | −0.4581 |
| miR-224 (#228) | 0.1365 | −0.4549 |
| miR-30d (#72) | 0.1301 | −0.4336 |
| miR-92-2 (#82) | 0.116 | −0.3865 |
| miR-199a-1 (#191) | 0.1158 | −0.3861 |
| miR-223 (#227) | 0.1141 | −0.3803 |
| miR-29c (#65) | 0.113 | −0.3768 |
| miR-30b (#68) | 0.1008 | −0.3361 |
| miR-129-1/2 (#117) | 0.1001 | −0.3337 |
| miR-197 (#189) | 0.0975 | −0.325 |
| miR-17-5p (#41) | 0.0955 | −0.3185 |
| miR-30c (#70) | 0.0948 | −0.316 |
| miR-7-1 (#19) | 0.0933 | −0.311 |
| miR-93-1 (#83) | 0.0918 | −0.3061 |
| miR-140 (#136) | 0.0904 | −0.3015 |
| miR-30a-5p (#66) | 0.077 | −0.2568 |
| miR-132 (#121) | 0.0654 | −0.2179 |
| miR-181b-1 (#210) | 0.0576 | −0.1918 |
| miR-152 prec (#151) | −0.0477 | 0.1591 |
| miR-23b (#51) | 0.0469 | −0.1562 |
| miR-20a (#46) | 0.0452 | −0.1507 |
| miR-222 (#225) | 0.0416 | −0.1385 |
| miR-27a (#59) | 0.0405 | −0.1351 |
| miR-92-1 (#81) | 0.0332 | −0.1106 |
| miR-21 (#47) | 0.0288 | −0.0959 |
| miR-129-1/2 prec (#118) | 0.0282 | −0.0939 |
| miR-150 (#148) | 0.0173 | −0.0578 |
| miR-32 (#75) | 0.0167 | −0.0558 |
| miR-106a (#99) | 0.0142 | −0.0473 |
| miR-29b-1 (#64) | 0.0084 | −0.028 |

*57 miRs selected, misclassification error after cross validation of 0.02. Fifty-seven miRs are over-expressed and 2 are down-regulated in cancer (indicated by positive and negative scores, respectively).

TABLE 12

MicroRNAs selected by prediction analysis of microarray (PAM) in prostate cancer (cancer vs. normal tissues)*.

| miR | Cancer score | Normal score |
|---|---|---|
| let-7d (#8) | 0.0528 | −0.4227 |
| miR-128a prec (#113) | −0.0412 | 0.3298 |
| miR-195 (#184) | 0.04 | −0.3199 |
| miR-203 (#197) | 0.0356 | −0.2851 |
| let-7a-2 prec (#2) | −0.0303 | 0.2504 |
| miR-34a (#78) | 0.0303 | −0.2428 |
| miR-20a (#46) | 0.029 | −0.2319 |
| miR-218-2 (#221) | −0.0252 | 0.2018 |
| miR-29a (#62) | 0.0247 | −0.1978 |
| miR-25 (#55) | 0.0233 | −0.1861 |

TABLE 12-continued

MicroRNAs selected by prediction analysis of microarray (PAM) in prostate cancer (cancer vs. normal tissues)*.

| miR | Cancer score | Normal score |
|---|---|---|
| miR-95 (#84) | 0.0233 | −0.1861 |
| miR-197 (#189) | 0.0198 | −0.1587 |
| miR-135-2 (#128) | 0.0198 | −0.1582 |
| miR-187 (#173) | 0.0192 | −0.1535 |
| miR-196-1 (#185) | 0.0176 | −0.1411 |
| miR-148 (#146) | 0.0175 | −0.1401 |
| miR-191 (#177) | 0.017 | −0.136 |
| miR-21 (#47) | 0.0169 | −0.1351 |
| let-7i (#10) | 0.0163 | −0.1303 |
| miR-198 (#190) | 0.0145 | −0.1161 |
| miR-199a-2 (#192) | 0.0136 | −0.1088 |
| miR-30c (#70) | 0.0133 | −0.1062 |
| miR-17-5p (#41) | 0.0132 | −0.1053 |
| miR-92-2 (#82) | 0.012 | −0.0961 |
| miR-146 (#144) | 0.0113 | −0.0908 |
| miR-181b-1 prec (#211) | 0.011 | −0.0878 |
| miR-32 (#75) | 0.0109 | −0.0873 |
| miR-206 (#202) | 0.0104 | −0.083 |
| miR-184 prec (#169) | 0.0096 | −0.0764 |
| miR-29a prec (#63) | −0.0095 | 0.076 |
| miR-29b-2 (#95) | 0.0092 | −0.0739 |
| miR-149 (#147) | −0.0084 | 0.0676 |
| miR-181b-1 (#210) | 0.0049 | −0.0392 |
| miR-196-1 prec (#186) | 0.0042 | −0.0335 |
| miR-93-1 (#83) | 0.0039 | −0.0312 |
| miR-223 (#227) | 0.0038 | −0.0308 |
| miR-16-1 (#38) | 0.0028 | −0.0226 |
| miR-101-1 prec (#92) | 0.0015 | −0.0123 |
| miR-124a-1 (#104) | 0.0015 | −0.0119 |
| miR-26a-1 (#56) | 0.0015 | −0.0119 |
| miR-214 (#212) | 0.0013 | −0.0105 |
| miR-27a (#59) | 0.0011 | −0.0091 |
| miR-24-1 (#53) | −8.00E−04 | 0.0067 |
| miR-106a (#99) | 7.00E−04 | −0.0057 |
| miR-199a-1 (#191) | 4.00E−04 | −0.0029 |

*T = 1, 45 miRs selected, misclassification error after cross validation of 0.11. Thirty-nine over-expressed miRs in cancer are indicated by positive cancer scores; 6 downregulated miRs are indicated by negative cancer scores.

TABLE 13

MicroRNAs selected by prediction analysis of microarray (PAM) in stomach cancer (cancer vs. normal tissues)*.

| miR | Cancer score | Normal score |
|---|---|---|
| miR-223 (#227) | 0.1896 | −0.1806 |
| miR-21 (#47) | 0.1872 | −0.1783 |
| miR-218-2 (#221) | −0.1552 | 0.1478 |
| miR-103-2 (#96) | 0.1206 | −0.1148 |
| miR-92-2 (#82) | 0.1142 | −0.1088 |
| miR-25 (#55) | 0.1097 | −0.1045 |
| miR-136 (#130) | −0.1097 | 0.1045 |
| miR-191 (#177) | 0.0946 | −0.0901 |
| miR-221 (#224) | 0.0919 | −0.0876 |
| miR-125b-2 (#111) | 0.0913 | −0.0869 |
| miR-103-1 (#97) | 0.0837 | −0.0797 |
| miR-214 (#212) | 0.0749 | −0.0713 |
| miR-222 (#225) | 0.0749 | −0.0713 |
| miR-212 prec (#209) | −0.054 | 0.0514 |
| miR-125b-1 (#109) | 0.0528 | −0.0503 |
| miR-100 (#91) | 0.0526 | −0.0501 |
| miR-107 (#100) | 0.0388 | −0.0369 |
| miR-92-1 (#81) | 0.0369 | −0.0351 |
| miR-96 (#86) | −0.0306 | 0.0291 |
| miR-192 (#178) | 0.0236 | −0.0224 |
| miR-23a (#50) | 0.022 | −0.021 |
| miR-215 (#213) | 0.0204 | −0.0194 |
| miR-7-2 (#21) | 0.0189 | −0.018 |
| miR-138-2 (#133) | −0.0185 | 0.0176 |
| miR-24-1 (#52) | 0.0151 | −0.0144 |
| miR-99b (#89) | 0.0098 | −0.0093 |
| miR-33b (#76) | −0.0049 | 0.0046 |
| miR-24-2 (#54) | 0.0041 | −0.0039 |

*T = 1, 28 miRs selected, misclassification error after cross validation of 0.19. Twenty-two over-expressed miRs in cancer are indicated by positive cancer scores; 6 down-regulated miRs are indicated by negative cancer scores.

TABLE 14

The microRNAs shared by the signatures of the 6 solid cancers*.

| miR | N | Tumor Type |
|---|---|---|
| miR-21 | 6 | Breast Colon Lung Pancreas Prostate Stomach |
| miR-17-5p | 5 | Breast Colon Lung Pancreas Prostate |
| miR-191 | 5 | Colon Lung Pancreas Prostate Stomach |
| miR-29b-2 | 4 | Breast Colon Pancreas Prostate |
| miR-223 | 4 | Colon Pancreas Prostate Stomach |
| miR-128b | 3 | Colon Lung Pancreas |
| miR-199a-1 | 3 | Lung Pancreas Prostate |
| miR-24-1 | 3 | Colon Pancreas Stomach |
| miR-24-2 | 3 | Colon Pancreas Stomach |
| miR-146 | 3 | Breast Pancreas Prostate |
| miR-155 | 3 | Breast Colon Lung |
| miR-181b-1 | 3 | Breast Pancreas Prostate |
| miR-20a | 3 | Colon Pancreas Prostate |
| miR-107 | 3 | Colon Pancreas Stomach |
| miR-32 | 3 | Colon Pancreas Prostate |
| miR-92-2 | 3 | Pancreas Prostate Stomach |
| miR-214 | 3 | Pancreas Prostate Stomach |
| miR-30c | 3 | Colon Pancreas Prostate |
| miR-25 | 3 | Pancreas Prostate Stomach |
| miR-221 | 3 | Colon Pancreas Stomach |
| miR-106a | 3 | Colon Pancreas Prostate |

*The list includes 21 commonly up-regulated microRNAs in 3 or more (N) types of solid cancers (p-value = $2.5 \times 10^{-3}$).

Figure 3:
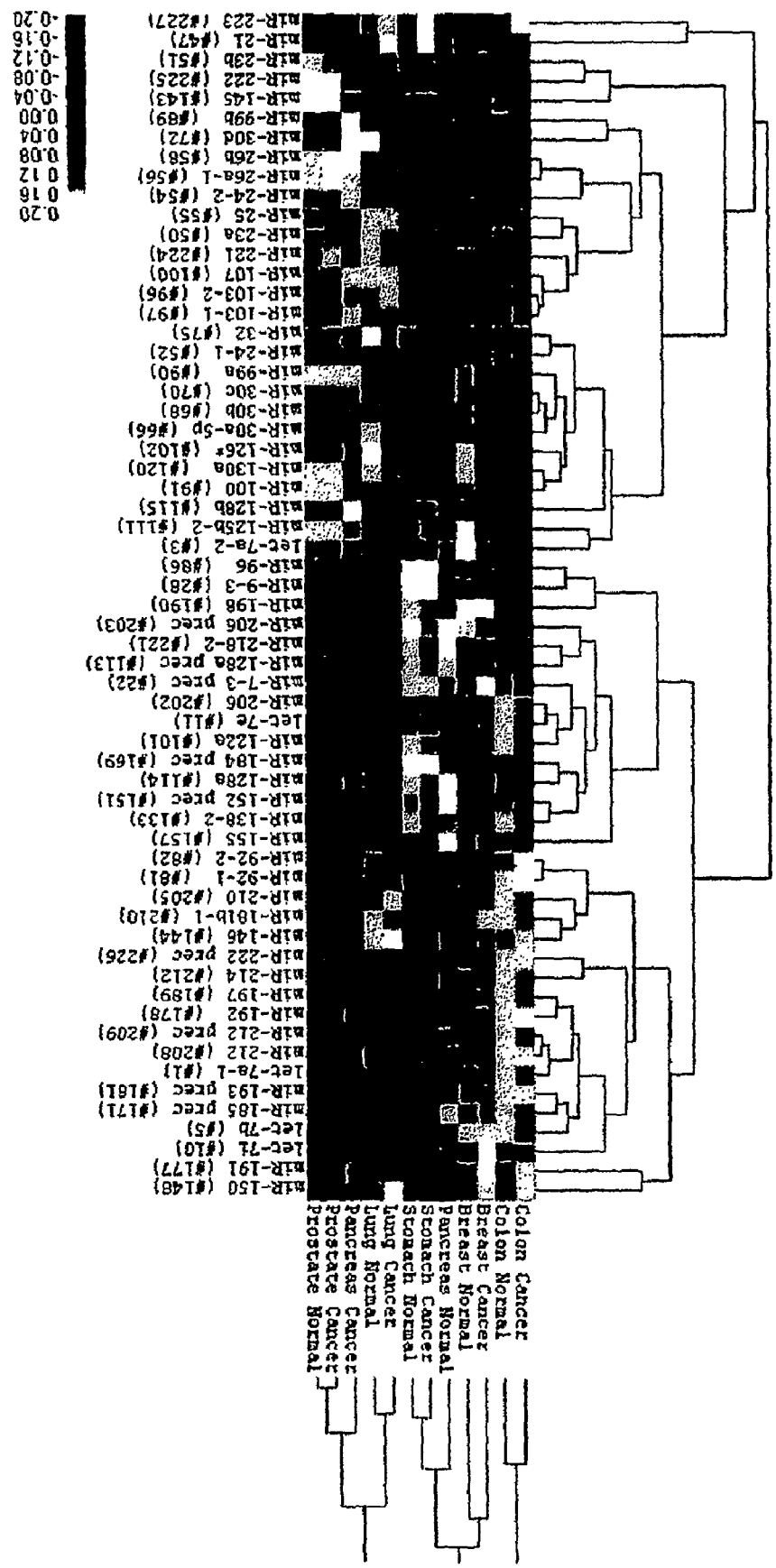
FIG. 3 depicts the expression of differentially-regulated miRNAs across solid cancers (top). Sixty-one microRNAs, which are present in at least 90% of the tissues solid cancers, are represented (right of panel). The tree displays the average absolute expression values for each of the listed microRNAs after $\log_2$ transformation. The mean was computed over all samples from the same tissue or tumor histotype. Genes were mean-centered and normalized using Gene Cluster 2.0. Average linkage clustering was performed using Euclidean distance.

To maximize concision, the mean absolute expression levels of the deregulated miRs for the 6 cancer/normal pairs were computed. Using the expression level of miRs in the comprehensive subset, the different tissues were correctly classified, irrespective of the disease status (FIG. 3).

Figure 4:
FIG. 4 depicts fold changes in the expression of miRNAs present in at least 75% of the solid tumors with at least 1 tumor absolute value higher than 2 in different cancer samples (top), relative to normal samples. The tree displays the $\log_2$ transformation of average fold changes (cancer vs. normal). The mean was computed over all samples from the same tissue or tumor histotype. Arrays were mean-centered and normalized using Gene Cluster 2.0. Average linkage clustering was performed using uncentered correlation metric.

FIG. 4 shows differential expression of the common microRNAs across the different tumor tissues, in relation to the normal tissues. The tree displays the different cancer types according to fold changes in the miRNA subset. Prostate, colon, stomach and pancreatic tissues are most similar among them, while lung and breast tissues were represented by a fairly different signature (FIG. 4). This tree clearly shows which miRNAs are associated with a particular cancer histotype.

Strikingly, miR-21, miR-191 and miR-17-5p are significantly over-expressed in all, or in 5 out of 6, of the tumor types that were considered. miR-21 was reported to be over-expressed in glioblastoma and to have anti-apoptotic properties (Chan, J. A., et al., Cancer Res. 65: 6029-6033 (2005)). Lung cancer shares a portion of its signature with breast cancer and a portion with the other solid tumors, including miR-17/20/92, all three of which are members of the microRNA cluster that actively cooperates with c-Myc to accelerate lymphomagenesis (He, L., et al., Nature 435: 828-833 (2005)). The identification of these microRNAs as being over-expressed is an excellent confirmation of our approach. A second miRNA group that is activated includes miR-210 and miR-213, together with miR-155, which was already reported to be amplified in large cell lymphomas (E is, P. S., et al., Proc. Natl. Acad. Sci. USA 102: 3627-3632 (2005)), children with Burkitt lymphoma (Metzler, M., et al., *Genes Chromosomes Cancer* 39:167-169 (2004)) and various B cell lymphomas (Kluiver, J, et al., *J. Pathol.*, e-published online, Jul. 22, 2005). These microRNAs are the only ones up-regulated in breast and lung cancer. miR-218-2 is consistently down-regulated in colon, stomach, prostate and pancreas cancers, but not in lung and breast carcinomas.

Several observations strengthen these results. First, in this study, the expression levels of both the precursor pre-miRNA and the mature miRNA were determined for the majority of genes. Of note, with the exception of miR-212 and miR-128a, in all other instances, the abnormally-expressed region was that corresponding to the active gene product. Second, as shown in FIG. 3, the expression variation of the miRNAs in the comprehensive subset was often univocal (namely, down- or up-regulation) across the different types of cancers, suggesting a common mechanism in human tumorigenesis. Third, the microarray data were validated by solution hybridization for 12 breast samples (miR-125b, miR-145 and miR-21; Iorio, M. V., et al., *Cancer Res.* 65: 7065-7070 (2005)) and 17 endocrine pancreatic and normal samples (miR-103, miR-155 and miR-204; data not shown), strongly confirming the accuracy of the microarray data.

EXAMPLE 3

Identification of Predicted Targets for MicroRNAs that are Deregulated in Solid Tumors Materials and Methods
Tumor Suppressor and Oncogene Target Predictions The most recent TargetScan predictions (April 2005) were used to identify putative microRNA targets. These include essentially the 3'UTR targets reported by Lewis et al. (Lewis, B. P., et al, *Cell* 120: 15-20 (2005)), with a few changes arising from updated gene boundary definitions from the April 2005 UCSC Genome Browser mapping of RefSeq mRNAs to the hg17 human genome assembly. Among the putative targets, known cancer genes (tumor suppressors and oncogenes) were specified according to their identification in the Cancer Gene Census, which is accessible at the internet site www.sanger.ac.uk/genetics/CGP/Census/, or as reported by OMIM at www.ncbi.nlm.nih.gov.
Target In Vitro Assays For luciferase reporter experiments, 3' UTR segments of Rb1, TGFBR2 and Plag1 that are predicted to interact with specific cancer-associated microRNAs were amplified by PCR from human genomic DNA and inserted into the pGL3 control vector (Promega) using the XbaI site immediately downstream from the stop codon of luciferase. The human megakaryocytic cell line, MEG-01, was grown in 10% FBS in RPMI medium 1640, supplemented with 1× nonessential amino acid and 1 mmol sodium pyruvate at 37° C. in a humified atmosphere of 5% $CO_2$. The cells were co-transfected in 12-well plates by using siPORT neoFX (Ambion, Austin, Tex.), according to the manufacturer's protocol, with 0.4 μg of the firefly luciferase reporter vector and 0.08 μg of the control vector containing *Renilla* luciferase, pRL-TK (Promega). For each well, microRNA oligonucleotides (Dharmacon Research, Lafayette, Colo.) and anti-sense or scrambled oligonucleotides (Ambion) were used at a concentration of 10 nM. Firefly and *Renilla* luciferase activities were measured consecutively at 24 h post transfection using dual-luciferase assays (Promega).
Western Blotting for RB1

Levels of RB1 protein were quantified using a mouse monoclonal anti-RB1 antibody (Santa Cruz, Calif.) using standard procedures for Western blotting. The normalization was performed with mouse monoclonal anti-Actin antibody (Sigma).
Results The functional significance of microRNA deregulation in cancer needs to be understood. In solid tumors, it appears that the most common microRNA event is gain of expression, while loss of expression in cancer is a more limited event, and more tissue specific. We used a three-step consequential approach in the following order: first, "in silico" prediction of targets, then luciferase assay for first validation of cancer relevant targets and finally, ex vivo tumor correlation between miRNA expression (by microarray) and target protein expression (by Western blotting) for a specific miRNA:mRNA interactor pair. Relevant targets for cancer miRNAs could be either recessive (e.g., tumor suppressors) or dominant (e.g., oncogenes) cancer genes. To test the hypothesis that microRNAs that are deregulated in solid tumors target known oncogenes or tumor suppressors, the predicted targets for these miRNAs were determined using TargetScan, a database of conserved 3' UTR microRNA targets (Lewis, B. P., et al, *Cell* 120: 15-20 (2005)). TargetScan contained 5,121 predictions for 18 miRNAs that are dysregulated in solid tumors, in the total 22,402 (26.5%) predictions. One hundred fifteen out of 263 (44%) well-known cancer genes were predicted as targets for these 18 miRNAs (Table 15). Because a high percentage of cancer genes are targeted by miRs that are deregulated in solid tumors, it is unlikely that these predictions are due to chance ($P<0.0001$ at Fisher exact-test).

Figure 6A:
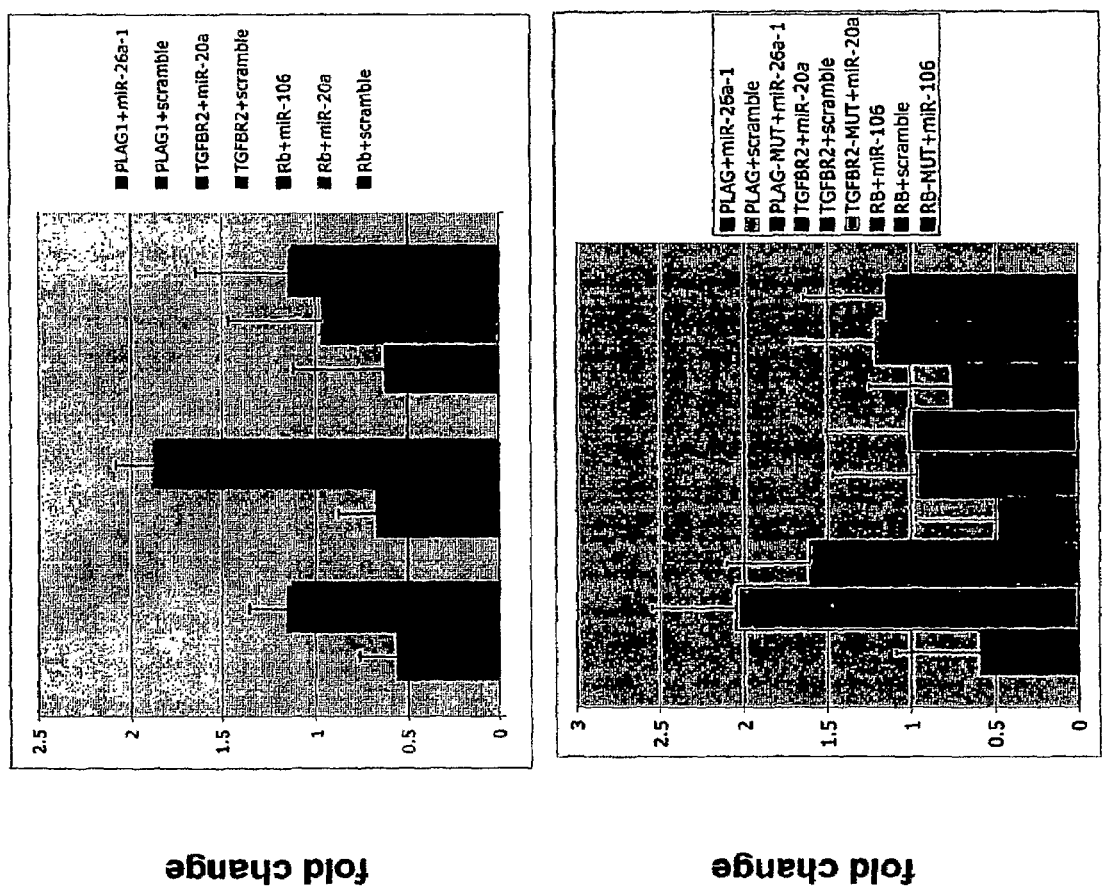
FIG. 6A depicts bar graphs indicating that the 3'UTR of different genes encoding cancer protein enables cancer regulation by microRNA. The relative repression of firefly luciferase expression (Fold Change) standardized to a renilla luciferase control. PLAG1, pleiomorphic adenoma gene 1; TGFBR2, transforming growth factor beta receptor II; Rb, retinoblastoma gene. pGL-3 (Promega) was used as the empty vector. miR-20a, miR-26a-1 and miR-106 oligoRNAs (sense and scrambled) were used for transfections. A second experiment using mutated versions of each target mRNA, which lack the 5' miRNA-end complementarity site (MUT), as controls is shown in the bottom panel. All the experiments were performed twice in triplicate (n=6).

In silico predictions for three different cancer genes, Retinoblastoma (Rb), TGF-beta-2 receptor (TGFBR2), and pleiomorphic adenoma gene 1 (PLAG1), were confirmed experimentally by in vitro assays. Using a luciferase reporter assay, three microRNAs tested (miR-106a, miR-20a and miR-26a-1) caused a significant reduction of protein translation relative to the scrambled control oligoRNAs in transfected MEG-01 cells (FIG. 6). Retinoblastoma 3'UTR, for example, was found to interact functionally with miR-106a. The biological significance of this miRNA:mRNA interaction is reinforced by previous reports showing that the Rb1 gene is normally transcribed in colon cancers, whilst various fractions of cells do not express Rb1 protein (Ali, A. A., et al., *FASEB J.* 7:931-937 (1993)). This finding suggests the existence of a post-transcriptional mechanism for regulating Rb1 that could be explained by concomitant miR-106a over-expression in colon carcinoma (FIG. 4). Furthermore, mir-20a is down-regulated in breast cancer (FIG. 4) and TFGBR2 protein is expressed in the epithelium of breast cancer cells (Buck, M. B., et al., *Clin. Cancer Res.* 10:491-498 (2004)). Conversely, the over-expression of mir-20a in colon cancer may represent a novel mechanism for down-regulating TGFBR2, in addition to mutational inactivation (Biswas, S., et al., *Cancer Res.* 64:687-692 (2004)).

Figure 5:
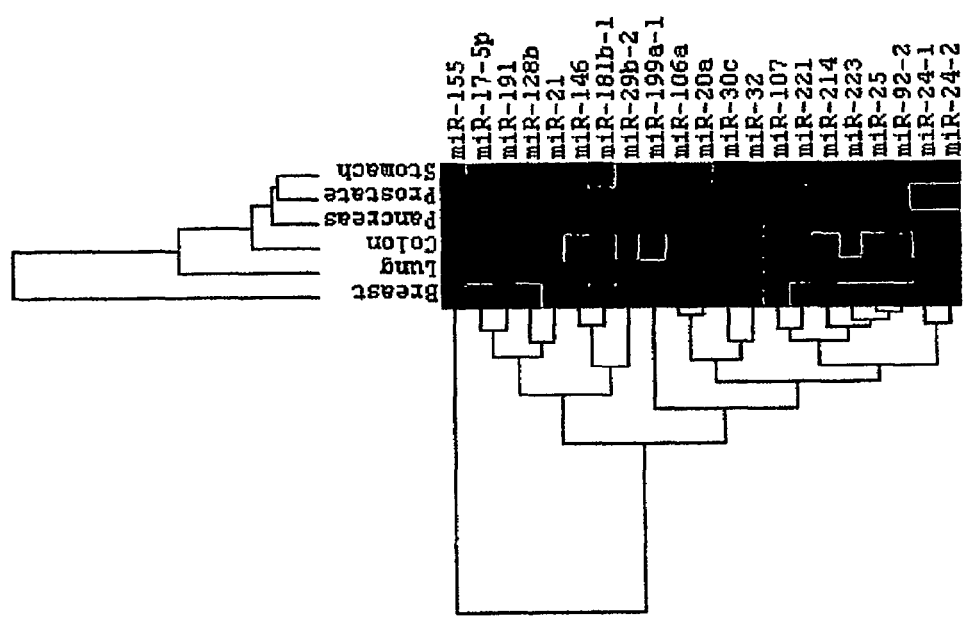
FIG. 5 depicts fold changes in the expression of miRNAs present in the signatures of at least 50% of the solid tumors in cancer vs. normal samples. The tree displays the $\log_2$ transformation of the average fold changes (cancer over normal). The mean was computed over all samples from the same tissue or tumor histotype. Arrays were mean centered and normalized using Gene Cluster 2.0. Average linkage clustering was performed using uncentered correlation metric.
Figure 6B:
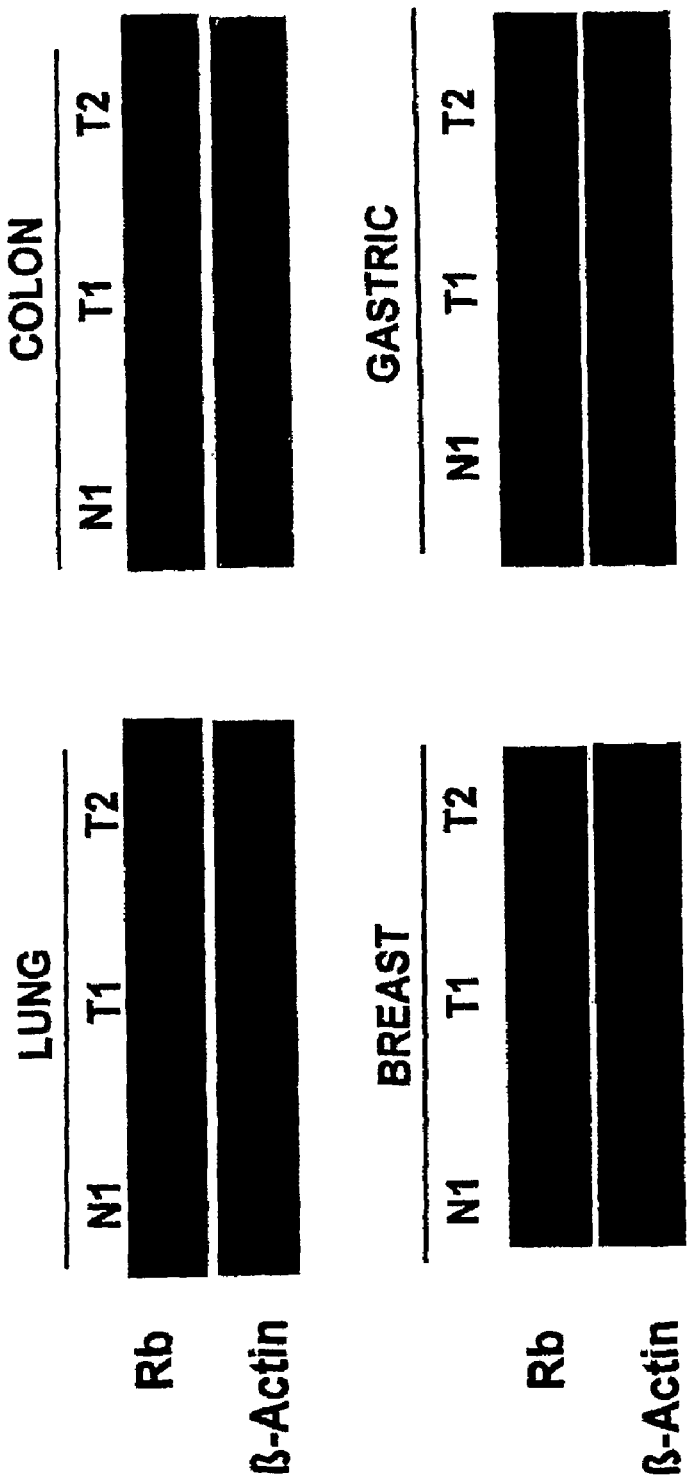
FIG. 6B depicts Western blots indicating that, in certain cancers (e.g., lung, breast, colon, gastric), the levels of RB1 (Rb) protein displays an inverse correlation with the level of miR-106a expression. β-Actin was used as a control for normalization. NI, normal sample; T1 and T2, tumor sample.
Figure 7:
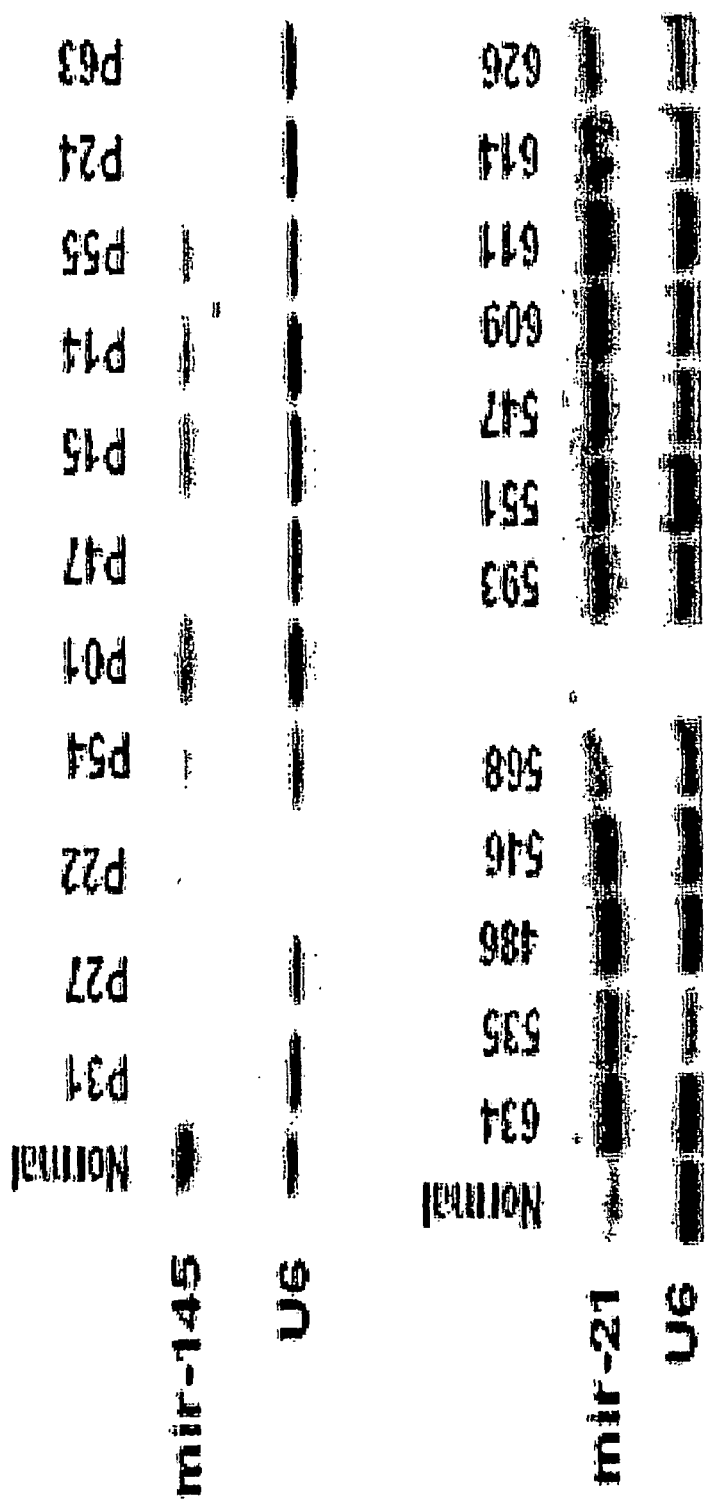
FIG. 7 depicts Northern blots showing down-regulation of miR-145 (top) and up-regulation of miR-21 (bottom) expression in breast cancer samples (P series and numbered series) relative to normal samples. Normalization was performed with a U6-specific probe.

Finally, a set of patient samples was tested to verify whether RB1 protein expression correlates with miR-106a expression (FIG. 5 and FIG. 6B). As expected, in gastric, prostate and lung tumor samples RB1 was down-regulated (in respect to the paired normal) and miR-106a was found to be over-expressed, while in breast tumor samples, where miR-106a is slightly down-regulated (FIG. 5 and FIG. 6B), RB1 is expressed at slightly higher levels then in the paired normal control.

These experimental proofs reinforce the hypothesis that key cancer genes are regulated by aberrant expression of miRs in solid cancers. These data add novel examples to the list of microRNA with important cancer gene targets, as previously shown by Johnson et al. (Johnson, S. M., et al., *Cell* 120: 635-647 (2005)) for the let-7:Ras interaction, O'Donnell et al. (O'Donnell, K. A., et al., Nature 435:839-843 (2005)) for the miR-17-5p:cMyc interaction, and Cimmino et al. (Cimmino, A., et al., Proc. Natl. Acad. Sci. USA 102:13944-13949 (2005)) for the mir-16:Bcl2 interaction. Notably, miR-17-5p and miR-16 are members of the miRNA solid cancer signature described herein.

TABLE 15

Oncogenes and tumor suppressor genes predicted by TargetScanS as targets of microRNAs from the comprehensive cancer subset.*

| miRNA gene | Gene Name | Gene description |
|---|---|---|
| miR-26a, miR-146 | ABL2 | v-abl Abelson murine leukemia viral oncogene homolog 2 (arg, Abelson-related gene) |
| miR-107 | AF5q31 | ALL1 fused gene from 5q31 |
| miR-20, miR-125b | AKT3 | v-akt murine thymoma viral oncogene homolog 3 |
| miR-26a, miR-155 miR-125b | APC | adenomatosis polyposis coli |
| miR-26a, miR-218 | ARHGEF12 | RHO guanine nucleotide exchange factor (GEF) 12 (LARG) |
| miR-107, miR-221 | ARNT | aryl hydrocarbon receptor nuclear translocator |
| miR-192 | ATF1 | activating transcription factor 1 |
| miR-26a | ATM | Ataxia telangiectasia mutated (includes complementation groups A, C and D) |
| miR-24 | AXL | AXL receptor tyrosine kinase |
| miR-26a, miR-107, miR-146, miR-155 miR-138, miR-92 | BCL11A | B-cell CLL/lymphoma 11A |
| miR-20 | BCL11B | B-cell CLL/lymphoma 11B (CTIP2) |
| miR-21 | BCL2 | B-cell CLL/lymphoma 2 |
| miR-26a, miR-26a miR-20, | BCL6 | B-cell CLL/lymphoma 6 (zinc finger protein 51) |
| miR-92 | BCL9 | B-cell CLL/lymphoma 9 |
| miR-26a, miR-223 miR-221, miR-125b | CBFB | core-binding factor, beta subunit |
| miR-218 | CCDC6 | coiled-coil domain containing 6 |
| miR-20 | CCND1 | cyclin D1 (PRAD1: parathyroid adenomatosis 1) |
| miR-26a, miR-20 | CCND2 | cyclin D2 |
| miR-26a, miR-107, miR-92 | CDK6 | cyclin-dependent kinase 6 |
| miR-20 | CDKN1A | cyclin-dependent kinase inhibitor 1A (p21, Cip1) |
| miR-221, miR-92 | CDKN1C | cyclin-dependent kinase inhibitor 1C (p57, Kip2) |
| miR-24 | CDX2 | caudal type homeo box transcription factor 2 |
| miR-92 | CEBPA | CCAAT/enhancer binding protein (C/EBP), alpha |
| miR-26a | CLTC | clathrin, heavy polypeptide (Hc) |
| miR-218 | COL1A1 | collagen, type I, alpha 1 |
| miR-26a | CREBBP | CREB binding protein (CBP) |
| miR-20 | CRK | v-crk avian sarcoma virus CT10 oncogene homolog |
| miR-20 | CSF1 | colony stimulating factor 1 (macrophage) |
| miR-221, miR-192 | DDX6 | DEAD/H (Asp-Glu-Ala-Asp/His) box polypeptide 6 (RNA helicase, 54 kD) |
| miR-138 | DEK | DEK oncogene (DNA binding) |
| miR-20 | E2F1 | E2F transcription factor 1 |
| miR-20 | ELK3 | ELK3, ETS-domain protein (SRF accessory protein 2) |
| miR-24 | ELL | ELL gene (11-19 lysine-rich leukemia gene) |
| miR-26a, miR-138 | ERBB4 | v-erb-a avian erythroblastic leukemia viral oncogene homolog-like 4 |
| miR-221, miR-155, miR-125b | ETS1 | v-ets avian erythroblastosis virus E26 oncogene homolog 1 |
| miR-20 | ETV1 | ets variant gene 1 |
| miR-125b | ETV6 | ets variant gene 6 (TEL oncogene) |
| miR-223 | FAT | FAT tumor suppressor (*Drosophila*) homolog |
| miR-223, miR-125b, miR-218 | FGFR2 | fibroblast growth factor receptor 2 |
| miR-92 | FLI1 | Friend leukemia virus integration 1 |
| miR-24, miR-20 | FLT1 | fms-related tyrosine kinase 1 (vascular endothelial growth factor/vascular permeability factor receptor) |
| miR-221 | FOS | v-fos FBJ murine osleosarcoma viral oncogene homolog |
| miR-92 | FOXG1B | forkhead box G1B |
| miR-223 | FOXO3A | forkhead box O3A |
| miR-125b | GOLGA5 | golgi autoantigen, golgin subfamily a, 5 (PTC5) |
| miR-138 | GPHN | gephyrin (GPH) |
| miR-107, miR-223, miR-20, miR-218 | HLF | hepatic leukemia factor |
| miR-26a, miR-107 | HMGA1 | high mobility group AT-hook 1 |
| miR-20 | HOXA13 | homeo box A13 |
| miR-92 | HOXA9 | homeo box A9 |
| miR-125b | IRF4 | interferon regulatory factor 4 |
| miR-146, miR-20, miR-138 | JAZF1 | juxtaposed with another zinc finger gene 1 |
| miR-92 | JUN | v-jun avian sarcoma virus 17 oncogene homolog |

TABLE 15-continued

Oncogenes and tumor suppressor genes predicted by TargetScanS as targets of microRNAs from the comprehensive cancer subset.*

| miRNA gene | Gene Name | Gene description |
|---|---|---|
| miR-155 | KRAS | v-Ki-ras2 Kirsten rat sarcoma 2 viral oncogene homolog |
| miR-218 | LASP1 | LIM and SH3 protein 1 |
| miR-218 | LHFP | lipoma HMGIC fusion partner |
| miR-125b, miR-218 | LIFR | leukemia inhibitory factor receptor |
| miR-223 | LMO2 | LIM domain only 2 (rhombotin-like 1) (RBTN2) |
| miR-223, miR-155, miR-125b, miR-92 | MAF | v-maf musculoaponeurotic fibrosarcoma (avian) oncogene homolog |
| miR-92 | MAP2K4 | mitogen-activated protein kinase kinase 4 |
| miR-146, miR-20 | MAP3K8 | mitogen-activated protein kinase kinase kinase 8 |
| miR-125b | MAX | MAX protein |
| miR-218 | MCC | mutated in colorectal cancers |
| miR-24 | MEN1 | multiple endocrine neoplasia I |
| miR-138 | MLLT6 | myeloid/lymphoid or mixed-lineage leukemia (trithorax homolog, *Drosophila*); translocated to, 6 (AF17) |
| miR-192 | MSN | moesin |
| miR-24 | MYB | v-myb avian myeloblastosis viral oncogene homolog |
| miR-107, miR-223, miR-146, miR-221, miR-155, miR-218 | MYBL1 | v-myb avian myeloblastosis viral oncogene homolog-like 1 |
| miR-107, miR-20 | MYCN | v-myc avian myelocytomatosis viral related oncogene, neuroblastoma derived |
| miR-107, miR-92 | MYH9 | myosin, heavy polypeptide 9, non-muscle |
| miR-24 | MYST4 | MYST histone acetyltransferase (monocytic leukemia) 4 (MORF) |
| miR-20 | NBL1 | neuroblastoma, suppression of tumorigenicity 1 |
| miR-125b | NIN | ninein (GSK3B interacting protein) |
| miR-26a, miR-107 | NKTR | natural killer-tumor recognition sequence |
| miR-92 | NOTCH1 | Notch homolog 1, translocation-associated (*Drosophila*) (TAN1) |
| miR-24 | NTRK3 | neurotrophic tyrosine kinase, receptor, type 3 |
| miR-125b | PCSK7 | proprotein convertase subtilisin/kexin type 7 |
| miR-24, miR-146 | PER1 | period homolog 1 (*Drosophila*) |
| miR-146, miR-125b, miR-138, | PHOX2B | paired-like homeobox 2b |
| miR-155 | PICALM | phosphatidylinositol binding clathrin assembly protein (CALM) |
| miR-24, miR-26a | PIM1 | pim-1 oncogene |
| miR24, miR-26a, miR-21, miR-107, miR-20, miR-155 | PLAG1 | pleiomorphic adenoma gene 1 |
| miR-218 | RAB8A | RAB8A, member RAS oncogene family |
| miR-24, miR-221 | RALA | v-ral simian leukemia viral oncogene homolog A (ras related) |
| miR-138 | RARA | retinoic acid receptor, alpha |
| miR-20, miR-192 | RB1 | retinoblastoma 1 (including osteosarcoma) |
| miR-20, | RBL1 | retinoblastoma-like 1 (p107) |
| miR-20 | RBL2 | retinoblastoma-like 2 (p130) |
| miR-155, miR-138 | REL | v-rel avian reticuloendotheliosis viral oncogene homolog |
| miR-20, miR-138 | RHOC | ras homolog gene family, member C |
| miR-20, miR-192 | RUNX1 | runt-related transcription factor 1 (AML1) |
| miR-107, miR-223 | SEPT6 | septin 6 |
| miR-146, miR-20, miR-125b | SET | SET translocation |
| miR-21, miR-20, miR-155, miR-218 | SKI | v-ski avian sarcoma viral oncogene homolog |
| miR-26a, miR-146 | SMAD4 | SMAD, mothers against DPP homolog 4 (*Drosophila*) |
| miR-155 | SPI1 | spleen focus forming virus (SFFV) proviral integration oncogene spi1 |
| miR-125b | SS18 | synovial sarcoma translocation, chromosome 18 |
| miR-107, miR-155 | SUFU | suppressor of fused homolog (*Drosophila*) |
| miR-92 | TAF15 | TAF15 RNA polymerase II, TATA box binding protein (TBP)-associated factor, 68 kDa |
| miR-26a, miR-221, miR-138 | TCF12 | transcription factor 12 (HTF4, helix-loop-helix transcription factors 4) |
| miR-21, miR-20 | TGFBR2 | transforming growth factor, beta receptor II (70-80 kD) |
| miR-24, miR-26a, miR-92 | TOP1 | topoisomerase (DNA) I |
| miR-138 | TPM4 | tropomyosin 4 |
| miR-20 | TRIP11 | thyroid hormone receptor interactor 11 |
| miR-92 | TSC1 | Tuberous sclerosis 1 |
| miR-20 | TSG101 | Tumor susceptibility gene 101 |
| miR-20 | TUSC2 | Tumor suppressor candidate 2 |
| miR-24 | VAV1 | vav 1 oncogene |
| miR-125b | VAV2 | vav 2 oncogene |

TABLE 15-continued

Oncogenes and tumor suppressor genes predicted by TargetScanS as targets of microRNAs from the comprehensive cancer subset.*

| miRNA gene | Gene Name | Gene description |
| --- | --- | --- |
| miR-107 | WHSC1 | Wolf-Hirschhorn syndrome candidate 1(MMSET) |
| miR-138 | WHSC1L1 | Wolf-Hirschhorn syndrome candidate 1-like 1 (NSD3) |
| miR-26a | WNT5A | wingless-type MMTV integration site family, member 5A |
| miR-26a, miR-20, miR-125b | YES1 | v-yes-1 Yamaguchi sarcoma viral oncogene homolog 1 |
| miR-107, miR-221 | ZNF198 | zinc finger protein 198 |
| miR-218 | ZNFN1A1 | zinc finger protein, subfamily 1A, 1 (Ikaros) |

*Known cancer genes (e.g., tumor suppressors, oncogenes) comprise those identified in the Cancer Gene Census at www.sanger.ac.uk/genetics/CGP/Census/or reported by OMIM at www.ncbi.nlm.nih.gov.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing whether a subject has a solid cancer, comprising measuring in a test sample from the subject a level of miR-21 gene product and miR-191 gene product, comparing the level of the miR-21 gene product and miR-191 gene product in the test sample to a control level of miR-21 gene product and miR-191 gene product; and diagnosing whether a subject has a solid cancer selected from the group consisting of colon, lung, pancreas, prostate, and stomach cancer, wherein an increase in the level of miR-21 gene product and miR-191 gene product in the test sample, relative to the control level of miR-21 gene product and miR-191 gene product, is indicative of the subject having a solid cancer selected from the group consisting of colon, lung, pancreas, prostate, and stomach cancer.

2. A method of claim 1, comprising:

(1) reverse transcribing miR-21 RNA and miR-191 RNA from a test sample obtained from the subject to provide miR-21 and miR-191 RNA target oligodeoxynucleotide;

(2) hybridizing the miR-21 and miR-191 RNA target oligodeoxynucleotide to a microarray comprising miRNA-specific probe oligonucleotides that include miR-21 RNA and miR-191 RNA specific probe oligonucleotide to provide a hybridization profile for the test sample; and (3) comparing the test sample hybridization profile to a control hybridization profile, wherein, if a signal of miR-21 RNA and miR-191 RNA in the test sample hybridization profile is greater than the signal of the miR-21 RNA and miR-191 RNA in the control hybridization profile, then the subject has a solid cancer selected from the group consisting of colon, lung, pancreas, prostate, and stomach cancer.

3. A method of claim 1, which further comprises measuring at least one miR in addition to measuring miR-21 and miR-191.

* * * * *